US012791551B2

(12) United States Patent
Lee et al.

(10) Patent No.: US 12,791,551 B2
(45) Date of Patent: Nov. 10, 2026

(54) METHOD FOR EVALUATING EFFICACY OF ANTICANCER DRUG OR SCREENING ANTICANCER DRUG

(71) Applicant: ORGANOIDSCIENCES LTD., Daejeon (KR)

(72) Inventors: Bo Eun Lee, Seongnam-si (KR); Sarang Kim, Seongnam-si (KR); Yoori Shin, Seongnam-si (KR); Eun Jeong Kim, Seongnam-si (KR); Heera Lee, Seongnam-si (KR); Dong Hyeon Kim, Seongnam-si (KR); Jihyo Kim, Seongnam-si (KR)

(73) Assignee: ORGANOIDSCIENCES LTD., Daejeon (KR)

( * ) Notice: Subject to any disclaimer, the term of this patent is extended or adjusted under 35 U.S.C. 154(b) by 0 days.

(21) Appl. No.: 17/928,829

(22) PCT Filed: Sep. 16, 2022

(86) PCT No.: PCT/KR2022/013919
§ 371 (c)(1),
(2) Date: Nov. 30, 2022

(87) PCT Pub. No.: WO2023/043278
PCT Pub. Date: Mar. 23, 2023

(65) Prior Publication Data

US 2024/0219373 A1 Jul. 4, 2024

(30) Foreign Application Priority Data

Sep. 17, 2021 (KR) ........................ 10-2021-0124736
Jul. 26, 2022 (KR) ........................ 10-2022-0092787
Jul. 29, 2022 (KR) ........................ 10-2022-0095105
Aug. 2, 2022 (KR) ........................ 10-2022-0096407
Aug. 9, 2022 (KR) ........................ 10-2022-0099498

(51) Int. Cl.
*G01N 33/50* (2006.01)

(52) U.S. Cl.
CPC ..... *G01N 33/5047* (2013.01); *G01N 33/5011* (2013.01); *G01N 33/505* (2013.01); *G01N 33/5055* (2013.01); *G01N 33/5088* (2013.01)

(58) Field of Classification Search
CPC ............. G01N 33/5011; G01N 33/505; G01N 33/5055; G01N 33/5088; G01N 33/5047
See application file for complete search history.

(56) References Cited

U.S. PATENT DOCUMENTS

2023/0042929 A1* 2/2023 Appleton ............... C12M 35/08
2025/0189513 A1* 6/2025 Lee .................... G01N 33/5011

OTHER PUBLICATIONS

Li et al. Co-culture of tumor organoids with immune cells for immune-oncology drug development. Mol Cancer Ther 18 (12 Supplement): B142 (2019).*
Cattaneo et al. Tumor organoid-T-cell coculture systems. Nature Protocols 15: 15-39 (Jan. 2020).*

* cited by examiner

*Primary Examiner* — Gailene Gabel
(74) *Attorney, Agent, or Firm* — Sughrue Mion, PLLC

(57) ABSTRACT

A method for evaluating an efficacy of an anticancer drug or an anticancer drug candidate includes treating a mixture of cancer organoids and immune cells with the anticancer drug or the anticancer drug candidate. The method further includes an anticancer drug efficacy evaluation system or anticancer drug screening system comprising cancer organoids and immune cells. The mixture of cancer organoids and immune cells is mixed in a specific ratio and can reproduce a tumor microenvironment in which cancer cells exist in the body, thereby enabling accurate prediction of the efficacy of the drug when administered to a subject.

7 Claims, 44 Drawing Sheets

METHOD FOR EVALUATING EFFICACY OF ANTICANCER DRUG OR SCREENING ANTICANCER DRUG

CROSS REFERENCE TO RELATED APPLICATIONS

This application is a National Stage of International Application No. PCT/KR2022/013919 filed Sep. 16, 2022, claiming priority based on Korean Patent Application No. 10-2021-0124736 filed Sep. 17, 2021, Korean Patent Application No. 10- 2022-0092787 filed Jul. 26, 2022, Korean Patent Application No. 10-2022-0095105 filed Jul. 29, 2022, Korean Patent Application No. 10-2022-0096407 filed Aug. 2, 2022 and Korean Patent Application No. 10-2022-0099498 filed Aug. 9, 2022, the entire disclosures of which are incorporated herein by reference.

TECHNICAL FIELD

The present invention relates to a method for evaluating an efficacy of an anticancer drug or an anticancer drug candidate, comprising the step of treating a mixture of cancer organoids and immune cells with the anticancer drug or the anticancer drug candidate. In addition, it relates to the anticancer drug efficacy evaluation system or anticancer drug screening system comprising cancer organoids and immune cells.

BACKGROUND ART

An organoid is an organ analogue prepared by three-dimensional culture of cells derived from tissues or organs. It has advantages of long-term culture, cryopreservation, and easy manipulation and observation. At the same time, it is used as an experimental model that can study physiological phenomena at a level higher than that of cells by reproducing the hierarchical and histological structures of cells which can be observed in the body, as well as maintaining the original characteristics of the cells without immortalization. Due to these characteristics, the organoid can evaluate drugs with high accuracy compared to immortalized cell lines with changed intrinsic characteristics thereof and animal models with different structures from the human body. In particular, there are advantages in that it is possible to check the efficacy as well as the safety of the drug prior to clinical trials on humans because patient-derived tissues are used. However, cancer organoids previously developed as drug evaluation models have a limitation in not reflecting the tumor microenvironment, and thus there is a need to develop organoids with various tumor microenvironments and use them as drug evaluation models.

The tumor microenvironment is a cellular environment in which cancer cells are surrounded by blood vessels, immune cells, fibroblasts, lymphocytes, signaling molecules and extracellular matrix (ECM). In the tumor microenvironment, cancer cells influence the microenvironment by inducing extracellular signal release, promotion of cancer cell neovascularization, peripheral tolerance, etc. Therefore, cancer cells change the microenvironment, or the microenvironment affects the growth or metastasis of cancer cells. In particular, the tumor microenvironment related to lymphocytes is highly associated not only to the occurrence and metastasis of cancer, but also to the immune system evasion of cancer, which affects the treatment response by anticancer agents and is a major target for anticancer immunotherapy.

For example, cells such as cytotoxic T cells (CD8+ T cells), regulatory T cells (Tregs), Myeloid-Derived Suppressor Cells (MDSCs), and Dendritic cells (DCs), Tumor-Associated Macrophages (TAMs), Tumor-Infiltrating Lymphocytes (TILs) and Cancer-Associated Fibroblasts (CAFs) present in the tumor microenvironment are known to affect the efficacy of cancer immunotherapy. These cells suppress the therapeutic effect of cancer immunotherapy by limiting infiltration of T cells into cancer tissues as well as reducing the proliferation and survival of tumor-infiltrating lymphocytes.

TECHNICAL PROBLEM

The inventors have developed cancer organoids with the tumor microenvironment, and conducted various studies to use them as a platform for drug evaluation. As a result, a system co-culturing cancer organoids and immune cells among various cells comprised in the tumor microenvironment at a specific ratio was established. In addition, the present invention has been completed by experimentally demonstrating that the efficacy of the drug can be accurately confirmed as cancer organoids grow properly in the system.

TECHNICAL SOLUTION

Each description and embodiment disclosed in the present invention may also apply to other descriptions and embodiments. That is, all combinations of the various elements disclosed herein fall within the scope of the present invention. In addition, it cannot be considered that the scope of the present invention is limited by the specific descriptions described below.

In addition, it should be understood that terms not specifically defined in this specification have meanings commonly used in the technical field to which the present invention pertains. Also, unless otherwise defined by context, the singular includes the plural and the plural includes the singular.

One aspect of the present invention provides a method for evaluating an efficacy of an anticancer drug candidate, comprising the following steps:

(a) mixing cancer organoids and immune cells in a ratio of 1:0.5 to 5 and co-culturing the mixture;

(b) treating the mixture of step (a) with an anticancer drug candidate; and (c) determining that the efficacy of the anticancer drug candidate is excellent when a growth inhibition or death of cancer organoid is increased in the group treated with the anticancer drug candidate of step (b) compared to a positive control group or a group not treated with the anticancer drug candidate.

Anticancer drugs, especially immune anticancer drugs, use the patient's immune cells to kill a tumor, and thus the evaluation platform for evaluating its efficacy should mimic the immune environment in the body. In the present invention, the evaluation platform capable of co-culturing cancer organoids and various immune cells was constructed in order to mimic the immune environment in vitro. All types of immune cells should be co-cultured in order to completely mimic the immune environment of the patient, but the ratio of immune cells is different for each patient, which results in limiting to mimic it in vitro. In particular, if the ratio of immune cells included in the drug evaluation platform changes, the efficacy of the drug also changes, which makes it difficult to predict the efficacy. Therefore, each platform was constructed depending on the types of immune cells for the purpose of accurately evaluating the efficacy of drugs. In addition, the platform was constructed using various immune cells so that an appropriate efficacy evaluation platform can be chosen in consideration of the immune cells targeted by the drug.

Specifically, the step (a) is mixing cancer organoids and immune cells and co-culturing the mixture, and which reproduces the in vivo tumor microenvironment in vitro.

In the present invention, the immune cells may be at least one selected from the group consisting of cytotoxic T cells, M1 macrophages, M2 macrophages, TILs, regulatory T cells and dendritic cells.

As used herein, the term "organoid" refers to clumps of cells having a three-dimensional structure, and it refers to an organ analogue prepared by 3D culture of cells isolated from an organ or tissue. Organoids can reproduce the particular function and shape of the human tissue or organ because it comprises specific cell populations constituting tissues or organs and is structurally organized in a form similar to actual tissues or organs of human body.

As used herein, the term "cancer organoid" refers to organoids derived from cells isolated from tumors.

As used herein, the term "cytotoxic T cells (CD8+ T cells)" refers to lymphocytes that perform antigen-specific adaptive immunity or acquired immunity. Cytotoxic T cells kill cells infected with pathogens such as bacteria, viruses and cancer cells, and produce cytokines such as TNF-α and IFN-γ. The cytotoxic T cells according to the present invention may be those infiltrated into or isolated from the tumor tissue. In the present specification, the cytotoxic T cells may also be used interchangeably with "differentiated T cells", "post-differentiation T cells", "activated T cells" and "CD8+ T cells".

As used herein, the term "M1 macrophage (classically activated macrophage, M1)" is a type of Tumor-Associated Macrophage (TAM), and it refers to macrophages activated by cytokines such as LPS, IFN-γ, IL-1β, TNF-α, TLR engagement, etc. M1 secretes pro-inflammatory cytokines or chemokines such as IL-6, IL-12 or TNF-α, and induces pathogen death or cancer cell death by activating T cells through functioning as an antigen-presenting cell (APC) or by activating Tumor Infiltrating Lymphocytes (TIL) or NK cells, or directly kill tumor cells through phagocytosis. In the present specification, the M1 macrophage may also be used interchangeably with "M1".

As used herein, the term "M2 macrophage (alternatively activated macrophage, M2)" is a type of Tumor-Associated Macrophage (TAM), and it refers to macrophages activated by cytokines such as IL-4, IL-13, IL-10, etc. The M2 secretes enzymes such as MMP or COX-2, or anti-inflammatory cytokines such as IL-10 or TGF-β, and accordingly carries out immune responses related to inflammation reduction, wound healing or tissue repair. However, the enzyme secreted by M2 may promote the proliferation and metastasis of tumor cells by destroying the tissue surrounding the tumor, or involve in the initiation and maintenance of angiogenesis to induce tumor growth. In the present specification, the M2 macrophage may also be used interchangeably with "M2".

As used herein, the term "TIL" refers to lymphocytes present in the vicinity of or infiltrating tumor tissue, also called "tumor-infiltrating lymphocyte". In addition, TIL may be a population of lymphocytes composed of various types of immune cells. The TIL according to the present invention may be that expressing a CD8 protein on a cell surface, preferably CD8+ T cells, but is not limited thereto.

As used herein, the term "regulatory T cell (Treg)" refers to lymphocytes that plays an important role in maintaining homeostasis and immune tolerance by suppressing the immune response, and preventing autoimmunity by suppressing T cell proliferation and cytokine production. The regulatory T cells according to the present invention may be that infiltrated into or isolated from the tumor tissue. In the present specification, the regulatory T cells may also be used interchangeably with "Treg cells" or "Treg".

As used herein, the term "Dendritic Cell (DC)" refers to a lymphocyte that serves as an antigen-presenting cell, which treats an antigen and presents it to T cells. Specifically, dendritic cells activates helper T cells (CD4+ T cells) and cytotoxic T cells (CD8+ T cells) that can suppress tumor growth to promote their functions, and accordingly may play a role in regulating tumor progression. The dendritic cells according to the present invention may be isolated from blood. In the present specification, the dendritic cells may also be used interchangeably with "DC cells" or "DC".

In the present invention, the immune cells may be cytotoxic T cells and M1 macrophages, and the co-culture of step (a) may be performed by mixing cancer organoids, cytotoxic T cells and M1 macrophages in a cell number ratio of 1:0.5:0.5 to 3. The tumor microenvironment in the body can be mimicked only when the cancer organoids, cytotoxic T cells and M1 macrophages are mixed in the above ratio and co-cultured. When co-cultured at a ratio other than the above ratio, the cancer organoid does not grow even before treating with a drug, resulting in not evaluating the anticancer effect of the drug, or M1 macrophages spontaneously die, resulting in not reproducing the tumor microenvironment. In addition, there is a problem that the efficacy of drugs acting by different mechanisms does not appear evenly when co-cultured at a ratio other than the above ratio. Thus, it is important to mix cancer organoids, cytotoxic T cells and M1 macrophages in the cell number ratio described above.

In the present invention, the immune cells may be M1 macrophages and M2 macrophages, and the co-culture of step (a) may be performed by mixing cancer organoids, M1 macrophages and M2 macrophages in a cell number ratio of 1:1 to 3:0.5 to 5. The tumor microenvironment in the body can be mimicked only when the cancer organoids, M1 macrophages and M2 macrophages are mixed in the above ratio and co-cultured. M1 macrophages exhibit tumor cell death promoting properties, and M2 macrophages exhibit tumor cell growth promoting properties. When co-cultured at a ratio other than the above ratio, the cancer organoid does not grow or otherwise grow excessively even before drug treatment, and accordingly there is a problem that the anticancer effect of the drug cannot be accurately evaluated. Thus, it is important to mix cancer organoids, M1 macrophages and M2 macrophages in the cell number ratio as described above.

In the present invention, the immune cells may be TILs, and the co-culture of step (a) may be performed by mixing cancer organoids and TILs in a cell number ratio of 1:1 to 2, particularly 1:1.5. The tumor microenvironment in the body can be mimicked only when the cancer organoids and TILs are mixed in the above ratio and co-cultured. When co-cultured at a ratio other than the above ratio, the growth of cancer organoids remarkably increases, resulting in not responding to the drug, or cancer organoids do not grow, resulting in not evaluating the anticancer effect of the drug. In addition, there is a problem that the efficacy of drugs acting by different mechanisms does not appear evenly when co-cultured at a ratio other than the above ratio. Thus, it is important to mix cancer organoids and TILs in the cell number ratio described above.

In the present invention, the immune cells may be cytotoxic T cells and regulatory T cells, and the co-culture of step (a) may be performed by mixing cancer organoids, cytotoxic T cells and regulatory T cells in a cell number ratio of 1:3:0.5 to 3, particularly 1:3:1 to 3, more particularly 1:3:3. The tumor microenvironment in the body can be mimicked only when the cancer organoids, cytotoxic T cells and regulatory T cells are mixed in the above ratio and co-cultured. When co-cultured at a ratio other than the above ratio, the death rate of cancer organoids by the drug is remarkably low, resulting in a problem that the anticancer effect of the drug cannot be evaluated. In addition, there is a problem that the efficacy of drugs acting by different mechanisms does not appear evenly when co-cultured at a ratio other than the above ratio. Thus, it is important to mix cancer organoids, cytotoxic T cells and regulatory T cells in the cell number ratio described above.

In the present invention, the immune cells may be cytotoxic T cells and dendritic cells, and the co-culture of step (a) may be performed by mixing cancer organoids, cytotoxic T cells and dendritic cells in a cell number ratio of 1:3:0.5 to 5, particularly 1:3:0.5 to 1. The tumor microenvironment in the body can be mimicked only when the cancer organoids, cytotoxic T cells and dendritic cells are mixed in the above ratio and co-cultured. When co-cultured at a ratio other than the above ratio, the cancer organoids do not grow properly, or the death rate of the cancer organoids by the drug is remarkably low, resulting in a problem that the anticancer effect of the drug cannot be evaluated. In addition, there is a problem that the efficacy of drugs acting by different mechanisms does not appear evenly when co-cultured at a ratio other than the above ratio. Thus, it is important to mix cancer organoids, cytotoxic T cells and dendritic cells in the cell number ratio described above.

In the method for evaluating the efficacy of an anticancer drug candidate according to the present invention, the mixture of cancer organoids and immune cells in the above ratio is treated with an anticancer drug candidate. That is, the efficacy of the anticancer drug candidate is evaluated through a system that similarly reproduces the tumor microenvironment in which cancer cells exist in the body. Therefore, it is possible to accurately predict the efficacy of the anticancer drug candidate when administered to the subject.

In the method for evaluating the efficacy of an anticancer drug candidate according to the present invention, the step (b) is a step of treating an anticancer drug candidate to the mixture in which cancer organoids and immune cells are co-cultured according to the step (a).

As used herein, the term "anticancer drug" refers to a substance that has a preventive or therapeutic effect on cancer, specifically, a substance capable of killing cancer cells, cancer organoids or tumors, or inhibiting the growth thereof.

As used herein, the term "anticancer drug candidate" refers to a substance that is expected to have a preventive or therapeutic effect on cancer, specifically, a substance that is expected to kill cancer cells, cancer organoids or tumors, or inhibit the growth thereof.

In the present specification, the 'anticancer drug' may be used interchangeably with 'drug', and the 'treatment' may be used interchangeably with 'addition' or 'administration'.

Specifically, the anticancer drug or the anticancer drug candidate may target cancer organoids and/or immune cells. For example, the anticancer drug or the anticancer drug candidate may target only cancer organoids, only immune cells, or both cancer organoids and immune cells simultaneously. For example, the anticancer drug targeting immune cells may be atezolizumab, pembrolizumab, anti-TIGIT antibody or anti-CD47 antibody. The "anti-CD47 antibody" may increase phagocytosis of cancer cells by macrophages by directly blocking the binding between CD47 expressed on cancer cells and SIRPα expressed on macrophages.

In the present invention, the anticancer drug or anticancer drug candidate includes, but not limited to, a compound, a protein, a fusion protein, a compound-protein conjugate, a drug-protein conjugate, an antibody, a compound-antibody conjugate, a drug-antibody conjugate, an amino acid, a peptide, a virus, a carbohydrate, a lipid, a nucleic acid, an extract, a fraction, etc.

For example, it may include a compound, a peptide, a peptide mimetic, a fusion protein, an antibody, an aptamer, an antibody-drug conjugate (ADC), etc., but is not limited thereto. Preferably, it may be an antibody or an immuno-oncology drug.

As used herein, the term "antibody" includes a monoclonal antibody, a polyclonal antibody, a bispecific antibody, a multispecific antibody, a chimeric antibody, a humanized antibody, and a human antibody, and also includes antibodies already known in the art or commercially available in addition to novel antibodies. It includes a functional fragment of antibody molecules as well as full-length forms comprising two heavy chains and two light chains. The functional fragment of the antibody molecule refers to a fragment having at least an antigen-binding function, which may include, but not limited to, Fab, F(ab'), $F(ab')_2$, Fv, etc.

As used herein, the term "peptide mimetic" refers to a peptide or a modified peptide that biologically mimics the active ligand of a hormone, a cytokine, an enzyme substrate, a virus or other biological molecule. As used herein, the term "aptamer" refers to a single-stranded nucleic acid (such as DNA, RNA or modified nucleic acid) having a stable tertiary structure and having a high affinity and specificity to bind to a target molecule.

As another example, the anticancer drug may include, but not limited to, an antisense nucleic acid, a siRNA, a shRNA, a miRNA and a ribozyme that binds in a complementary manner to a DNA or a mRNA.

As used herein, the term "antisense nucleic acid" refers to DNA, RNA or fragments or derivatives thereof containing a nucleic acid sequence complementary to a particular mRNA sequence, and acts to inhibit the translation of mRNA into protein by binding or hybridizing complementary to the mRNA sequence. As used herein, the term "siRNA (small interfering RNA)" refers to a short double-stranded RNA capable of inducing RNA interference (RNAi) through cleavage of a particular mRNA. The siRNA comprises a sense RNA strand having a sequence homologous to the mRNA of a target gene and an antisense RNA strand having a complementary sequence thereto. Since siRNA can inhibit the expression of a target gene, it is used in a gene knock-down method or a gene therapy method. As used herein, the term "shRNA (short hairpin RNA)", as a single-stranded RNA, refers to an RNA consisting of a stem portion forming a double-stranded portion by hydrogen bonding and a loop portion having a ring shape. It can be processed by a protein such as Dicer and converted into siRNA, and perform the same function as siRNA. As used herein, the term "miRNA (microRNA)" refers to a non-coding RNA of 21 to 23 nt that regulates gene expression after transcription by promoting degradation of target RNA or inhibiting translation thereof. As used herein, the term "ribozyme" refers to an RNA molecule having an enzyme-like function that recognizes a particular nucleotide sequence and cuts it by itself. The ribozyme consists of a region that binds specifically by a complementary nucleotide sequence of a target messenger RNA strand and a region that cuts the target RNA.

The anticancer drug or anticancer drug candidate whose efficacy is evaluated or screened according to the method of the present invention may be, for example, preventing or treating biliary tract cancer, stomach cancer, lung cancer, liver cancer, colorectal cancer, colon cancer, small intestine cancer, pancreatic cancer, brain cancer, osteosarcoma, melanoma, breast cancer, sclerosing adenosis, uterine cancer, cervical cancer, head and neck cancer, esophageal cancer, thyroid cancer, parathyroid cancer, renal cancer, sarcoma, prostate cancer, urethral cancer, bladder cancer, hematologic malignancy, leukemia, lymphoma and fibroadenoma, but is not limited thereto.

In the method for evaluating the efficacy of an anticancer drug candidate according to the present invention, the step (c) is a step of determining that the efficacy of the anticancer drug candidate is excellent when a growth inhibition or death of cancer organoid is increased in the group treated with the anticancer drug candidate of step (b) compared to a positive control group or a group not treated with the anticancer drug candidate.

As used herein, the term “positive control group” refers to a group treated with a substance used as an anticancer drug in the art.

Specifically, the growth inhibition or death of cancer organoids may be confirmed by the increase or decrease of the area of the cancer organoids. When the area of the cancer organoid is decreased, it may be determined that growth inhibition or death of the cancer organoid is increased. In addition, the increase or decrease in the area of the cancer organoid can be confirmed by a method known in the art, for example, an analysis method such as HCS (High-Content Screening) or Flow-cytometer, but is not limited thereto.

Another aspect of the present invention provides an anticancer drug efficacy evaluation system for using the method for evaluating the efficacy of the anticancer drug candidate, comprising cancer organoids and immune cells.

In the anticancer drug efficacy evaluation system according to the present invention, each term has the same meaning as described above, unless otherwise specified.

The anticancer drug efficacy evaluation system of the present invention mimics the tumor microenvironment, and comprises cancer organoids as tumors constituting the tumor microenvironment in the body, and one or more selected from the group consisting of cytotoxic T cells, M1 macrophages, M2 macrophages, TILs, regulatory T cells and dendritic cells as immune cells.

Specifically, in case that the immune cells are cytotoxic T cells and M1 macrophages, the anticancer drug efficacy evaluation system may comprise cancer organoids, cytotoxic T cells and M1 macrophages in a cell number ratio of 1:0.5:0.5 to 3. The tumor microenvironment in the body can be mimicked only when the cancer organoids, cytotoxic T cells and M1 macrophages are mixed in the above ratio and co-cultured. When co-cultured at a ratio other than the above ratio, the cancer organoid does not grow even before drug treatment, resulting in not evaluating the anticancer effect of the drug, or M1 macrophages spontaneously die, resulting in not reproducing the tumor microenvironment. In addition, there is a problem that the efficacy of drugs acting by different mechanisms does not appear evenly when co-cultured at a ratio other than the above ratio. Thus, it is important to mix cancer organoids, cytotoxic T cells and M1 macrophages in the cell number ratio described above.

In addition, in case that the immune cells are M1 macrophages and M2 macrophages, the anticancer drug efficacy evaluation system may comprise cancer organoids, M1 macrophages and M2 macrophages in a cell number ratio of 1:1 to 3:0.5 to 5. The tumor microenvironment in the body can be mimicked only when the cancer organoids, M1 macrophages and M2 macrophages are mixed in the above ratio and co-cultured. As M1 macrophages exhibit tumor cell death promoting properties and M2 macrophages exhibit tumor cell growth promoting properties, the cancer organoid does not grow or grow excessively even before drug treatment when co-cultured at a ratio other than the above ratio. Accordingly, the anticancer effect of the drug cannot be accurately evaluated. Thus, it is important to mix cancer organoids, M1 macrophages and M2 macrophages in the cell number ratio described above.

In addition, in case that the immune cells are TILs, the anticancer drug efficacy evaluation system may comprise cancer organoids and TILs in a cell number ratio of 1:1 to 2, particularly 1:1.5. The tumor microenvironment in the body can be mimicked only when the cancer organoids and TILs are mixed in the above ratio and co-cultured. When co-cultured at a ratio other than the above ratio, the growth of cancer organoids remarkably increases before drug treatment so that it does not respond to the drug, or otherwise cancer organoids do not grow so that the anticancer effect of the drug cannot be evaluated. In addition, there is a problem that the efficacy of drugs acting by different mechanisms does not appear evenly when co-cultured at a ratio other than the above ratio. Thus, it is important to mix cancer organoids and TILs in the cell number ratio described above.

In addition, in case that the immune cells are cytotoxic T cells and regulatory T cells, the anticancer drug efficacy evaluation system may comprise cancer organoids, cytotoxic T cells and regulatory T cells in a cell number ratio of 1:3:0.5 to 3, particularly 1:3:1 to 3, more particularly 1:3:3. The tumor microenvironment in the body can be mimicked only when the cancer organoids, cytotoxic T cells and regulatory T cells are mixed in the above ratio and co-cultured. When co-cultured at a ratio other than the above ratio, the death rate of cancer organoids by the drug is remarkably low, resulting in a problem that the anticancer effect of the drug cannot be evaluated. In addition, there is a problem that the efficacy of drugs acting by different mechanisms does not appear evenly when co-cultured at a ratio other than the above ratio. Thus, it is important to mix cancer organoids, cytotoxic T cells and regulatory T cells in the cell number ratio described above.

In addition, in case that the immune cells are cytotoxic T cells and dendritic cells, the anticancer drug efficacy evaluation system may comprise cancer organoids, cytotoxic T cells and dendritic cells in a cell number ratio of 1:3:0.5 to 5, particularly 1:3:0.5 to 1. The tumor microenvironment in the body can be mimicked only when the cancer organoids, cytotoxic T cells and dendritic cells are mixed in the above ratio and co-cultured. When co-cultured at a ratio other than the above ratio, the cancer organoids do not grow properly, or the death rate of the cancer organoids by the drug is remarkably low, resulting in a problem that the anticancer effect of the drug cannot be evaluated. In addition, there is a problem that the efficacy of drugs acting by different mechanisms does not appear evenly when co-cultured at a ratio other than the above ratio. Thus, it is important to mix cancer organoids, cytotoxic T cells and dendritic cells in the cell number ratio described above.

The anticancer drug efficacy evaluation system according to the present invention comprising the mixture of cancer organoids and immune cells in the above ratio can similarly reproduce the tumor microenvironment in which cancer cells exist in the body. Therefore, it is possible to accurately predict the efficacy of anticancer drugs when administered to a subject, and thus it can be usefully utilized for evaluating the efficacy of anticancer drugs.

Another aspect of the present invention provides an anticancer drug screening system comprising cancer organoids and immune cells, using the method for evaluating the efficacy of the anticancer drug candidate.

In the anticancer drug screening system according to the present invention, each term has the same meaning as described above, unless otherwise specified.

Specifically, in case that the immune cells are cytotoxic T cells and M1 macrophages, the anticancer drug screening system may comprise cancer organoids, cytotoxic T cells and M1 macrophages in a cell number ratio of 1:0.5:0.5 to 3. The tumor microenvironment in the body can be mimicked only when the cancer organoids, cytotoxic T cells and M1 macrophages are mixed in the above ratio and co-cultured. When co-cultured at a ratio other than the above ratio, the cancer organoid does not grow even before drug treatment, resulting in not evaluating the anticancer effect of the drug, or M1 macrophages spontaneously die, resulting in not reproducing the tumor microenvironment. In addition, as there is a problem that the efficacy of drugs acting by different mechanisms does not appear evenly when co-cultured at a ratio other than the above ratio, it is important to mix cancer organoids, cytotoxic T cells and M1 macrophages in the cell number ratio described above.

In addition, in case that the immune cells are M1 macrophages and M2 macrophages, the anticancer drug screening system may comprise cancer organoids, M1 macrophages and M2 macrophages in a cell number ratio of 1:1 to 3:0.5 to 5. The tumor microenvironment in the body can be mimicked only when the cancer organoids, M1 macrophages and M2 macrophages are mixed in the above ratio and co-cultured. As M1 macrophages exhibit tumor cell death promoting properties and M2 macrophages exhibit tumor cell growth promoting properties, the cancer organoid does not grow or grow excessively even before drug treatment when co-cultured at a ratio other than the above ratio. Accordingly, there is a problem that the anticancer effect of the drug cannot be accurately evaluated. Thus, it is important to mix cancer organoids, M1 macrophages and M2 macrophages in the cell number ratio described above.

In addition, in case that the immune cells are TILs, the anticancer drug screening system may comprise cancer organoids and TILs in a cell number ratio of 1:1 to 2, particularly 1:1.5. The tumor microenvironment in the body can be mimicked only when the cancer organoids and TILs are mixed in the above ratio and co-cultured. When co-cultured at a ratio other than the above ratio, the growth of cancer organoids remarkably increases before drug treatment so that it does not respond to the drug, or otherwise cancer organoids do not grow so that the anticancer effect of the drug cannot be evaluated. In addition, as there is a problem that the efficacy of drugs acting by different mechanisms does not appear evenly when co-cultured at a ratio other than the above ratio, it is important to mix cancer organoids and TILs in the cell number ratio described above.

In addition, in case that the immune cells are cytotoxic T cells and regulatory T cells, the anticancer drug screening system may comprise cancer organoids, cytotoxic T cells and regulatory T cells in a cell number ratio of 1:3:0.5 to 3, particularly 1:3:1 to 3, more particularly 1:3:3. The tumor microenvironment in the body can be mimicked only when the cancer organoids, cytotoxic T cells and regulatory T cells are mixed in the above ratio and co-cultured. When co-cultured at a ratio other than the above ratio, the death rate of cancer organoids by the drug is remarkably low, resulting in a problem that the anticancer effect of the drug cannot be evaluated. In addition, as there is a problem that the efficacy of drugs acting by different mechanisms does not appear evenly when co-cultured at a ratio other than the above ratio, it is important to mix cancer organoids, cytotoxic T cells and regulatory T cells in the cell number ratio described above.

In addition, in case that the immune cells are cytotoxic T cells and dendritic cells, the anticancer drug screening system may comprise cancer organoids, cytotoxic T cells and dendritic cells in a cell number ratio of 1:3:0.5 to 5, particularly 1:3:0.5 to 1. The tumor microenvironment in the body can be mimicked only when the cancer organoids, cytotoxic T cells and dendritic cells are mixed in the above ratio and co-cultured. When co-cultured at a ratio other than the above ratio, the cancer organoids do not grow properly, or the death rate of the cancer organoids by the drug is remarkably low, resulting in a problem that the anticancer effect of the drug cannot be evaluated. In addition, as there is a problem that the efficacy of drugs acting by different mechanisms does not appear evenly when co-cultured at a ratio other than the above ratio, it is important to mix cancer organoids, cytotoxic T cells and dendritic cells in the cell number ratio described above.

The anticancer drug screening system of the present invention mimics the tumor microenvironment, and comprises cancer organoids as tumors constituting the tumor microenvironment in the body, and cytotoxic T cells, M1 macrophages, M2 macrophages, TILs, regulatory T cells and dendritic cells as immune cells.

The mixture of cancer organoids and immune cells according to the present invention is mixed in a specific ratio, and accordingly can similarly reproduce a tumor microenvironment in which cancer cells exist in the body. Therefore, it can make it possible to accurately predict the efficacy of the drug when administered to a subject.

The death rate was analyzed based on the results of measuring the growth rate after 72 hours (72 h) of drug treatment.

Figure 27:
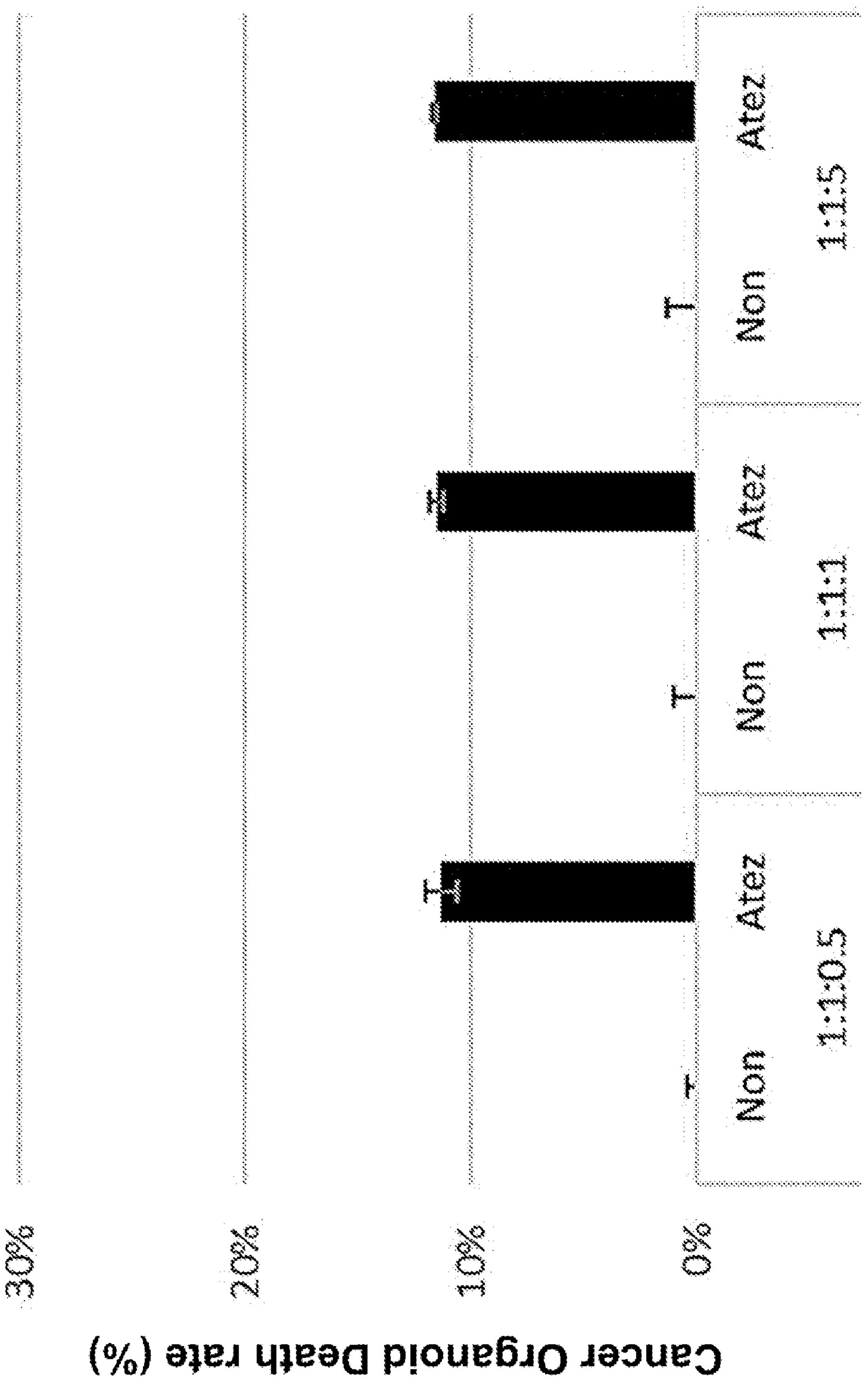

FIG. 27 is a graph showing the death rate of colorectal cancer organoids according to each co-culture ratio of colorectal cancer organoids, CD8+ T cells and DCs, and it relates to the result of co-culture in the mixed condition in which colorectal cancer organoids and CD8+ T cells were fixed in the cell number ratio of 1:1. 'Non' refers to a drug-untreated group, and 'Atez' refers to a drug-treated group treated with an atezolizumab as an exemplary drug. The death rate was analyzed based on the results of measuring the growth rate after 72 hours (72 h) of drug treatment.

Figure 28:
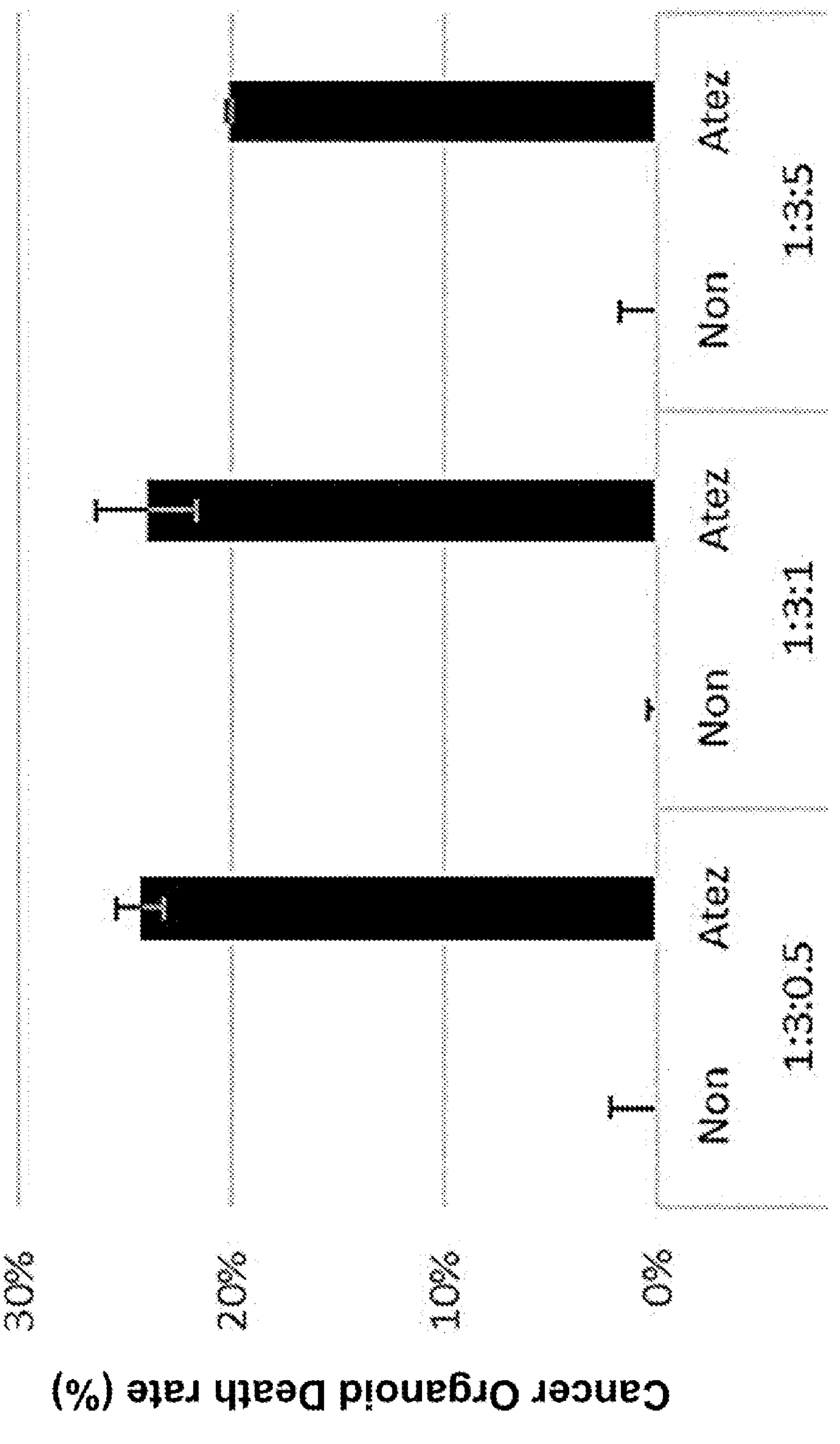

FIG. 28 is a graph showing the death rate of colorectal cancer organoids according to each co-culture ratio of colorectal cancer organoids, CD8+ T cells and DCs, and it relates to the result of co-culture in the mixed condition in which colorectal cancer organoids and CD8+ T cells were fixed in the cell number ratio of 1:3. 'Non' refers to a drug-untreated group, and 'Atez' refers to a drug-treated group treated with an atezolizumab as an exemplary drug. The death rate was analyzed based on the results of measuring the growth rate after 72 hours (72 h) of drug treatment.

Figure 29:
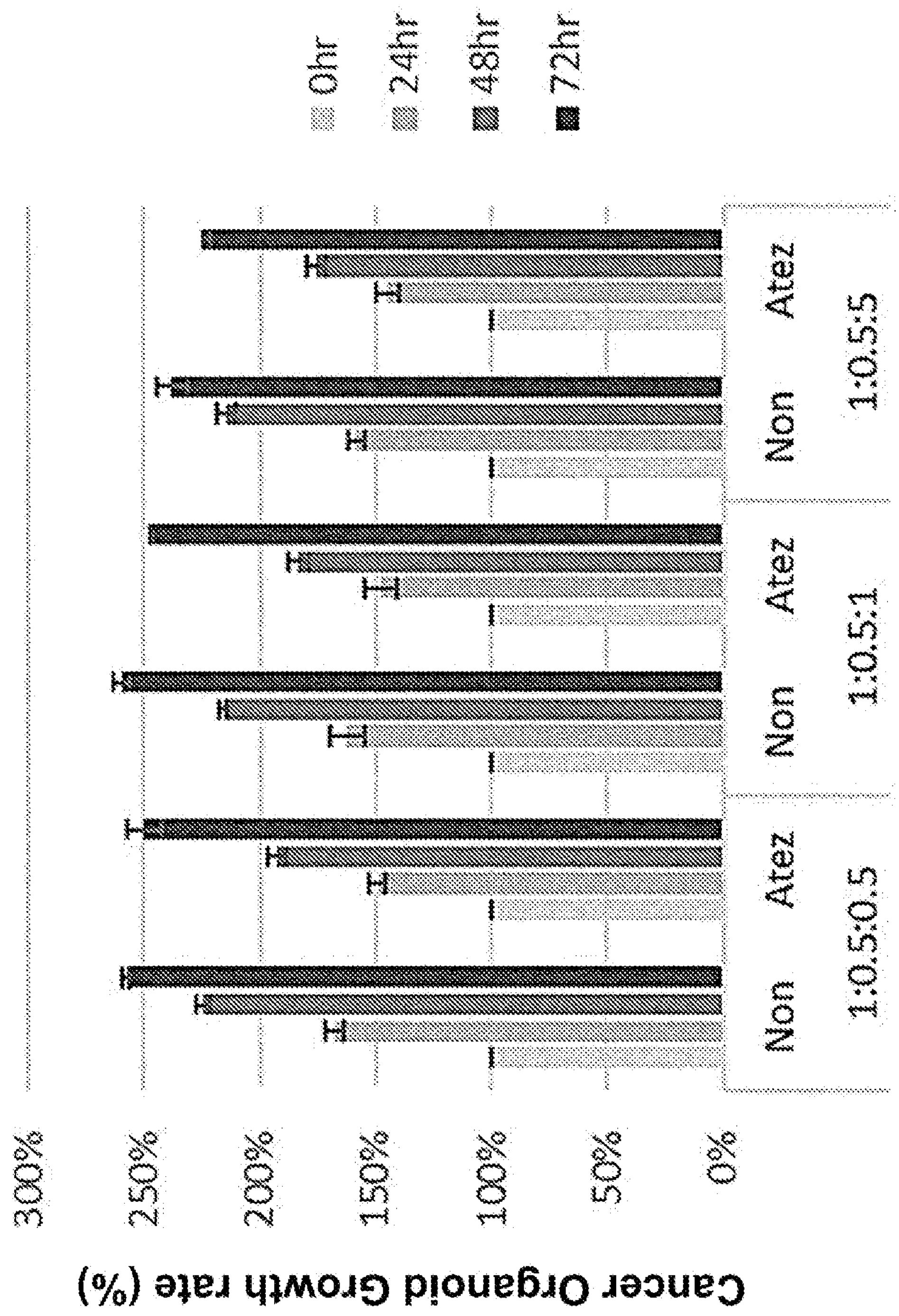

FIG. 29 is a graph showing the growth rate of lung cancer organoids according to each co-culture ratio of lung cancer organoids, CD8+ T cells and DCs, and it relates to the result of co-culture in the mixed condition in which lung cancer organoids and CD8+ T cells were fixed in the cell number ratio of 1:0.5. As a representative example, "1:0.5:0.5" described in the figure means that lung cancer organoids, CD8+ T cells and DCs are mixed in a cell number ratio of 1:0.5:0.5. The growth rate was analyzed immediately after the start of the co-culture (0 h), after 24 hours (24 h), after 48 hours (48 h), and after 72 hours (72 h), respectively. 'Non' refers to a drug-untreated group, and 'Atez' refers to a drug-treated group treated with an atezolizumab as an exemplary drug.

Figure 30:
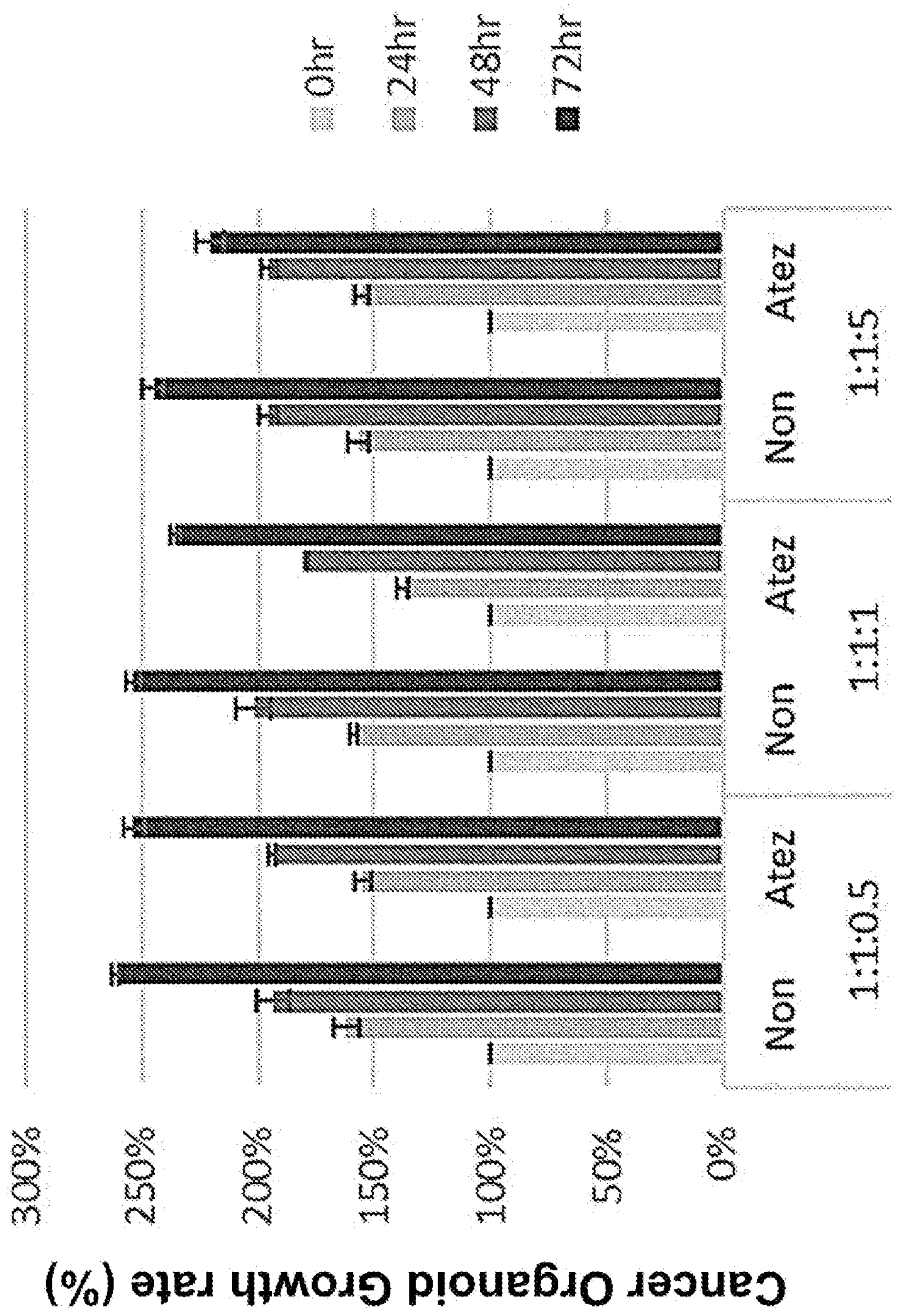

FIG. 30 is a graph showing the growth rate of lung cancer organoids according to each co-culture ratio of lung cancer organoids, CD8+ T cells and DCs, and it relates to the result of co-culture in the mixed condition in which lung cancer organoids and CD8+ T cells were fixed in the cell number ratio of 1:1. As a representative example, "1:1:0.5" described in the figure means that lung cancer organoids, CD8+ T cells and DCs are mixed in a cell number ratio of 1:1:0.5. The growth rate was analyzed immediately after the start of the co-culture (0 h), after 24 hours (24 h), after 48 hours (48 h), and after 72 hours (72 h), respectively. 'Non' refers to a drug-untreated group, and 'Atez' refers to a drug-treated group treated with an atezolizumab as an exemplary drug.

Figure 31:
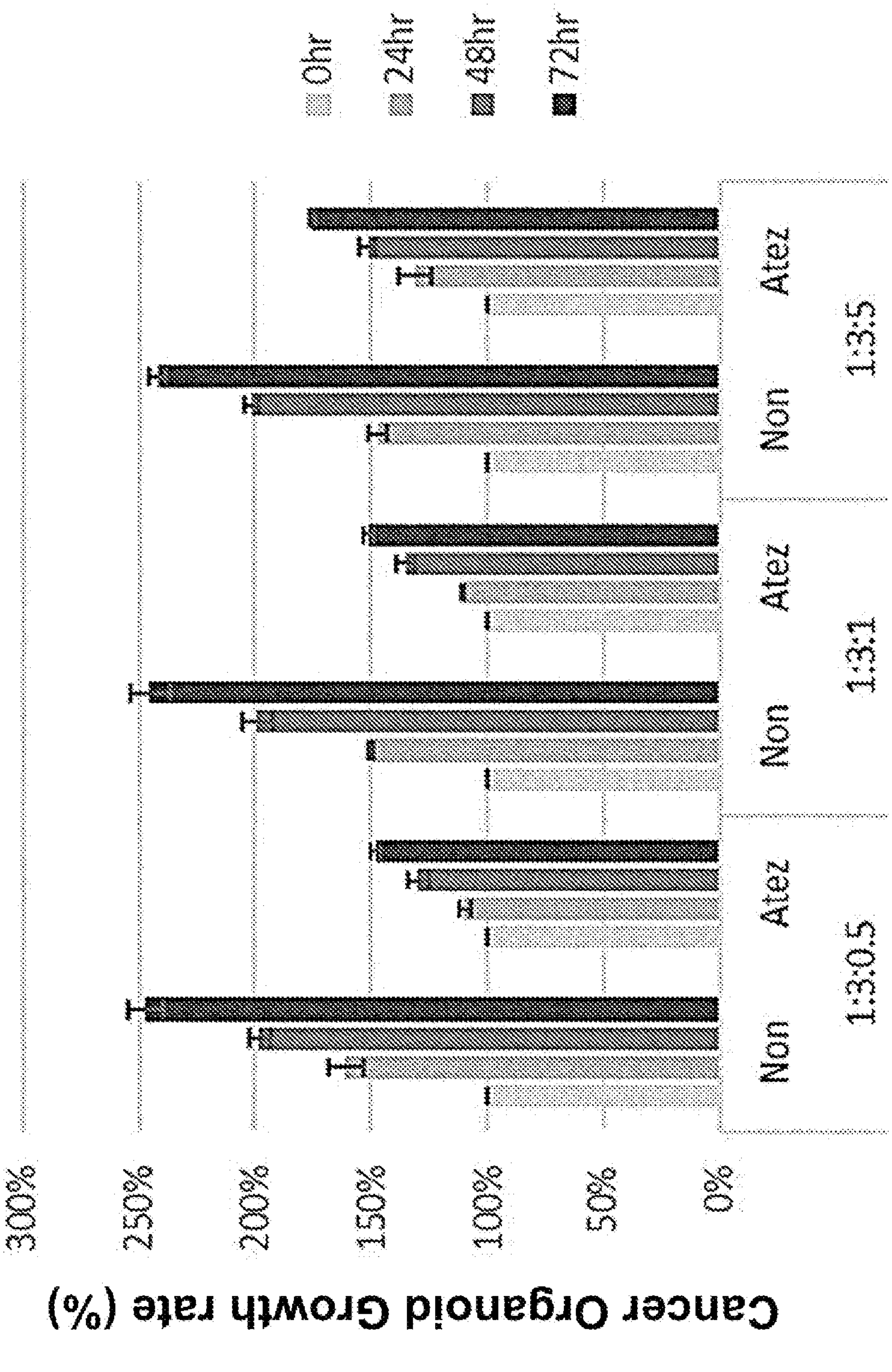

FIG. 31 is a graph showing the growth rate of lung cancer organoids according to each co-culture ratio of lung cancer organoids, CD8+ T cells and DCs, and it relates to the result of co-culture in the mixed condition in which lung cancer organoids and CD8+ T cells were fixed in the cell number ratio of 1:3. As a representative example, "1:3:0.5" described in the figure means that lung cancer organoids, CD8+ T cells and DCs are mixed in a cell number ratio of 1:3:0.5. The growth rate was analyzed immediately after the start of the co-culture (0 h), after 24 hours (24 h), after 48 hours (48 h), and after 72 hours (72 h), respectively. 'Non' refers to a drug-untreated group, and 'Atez' refers to a drug-treated group treated with an atezolizumab as an exemplary drug.

Figure 32:
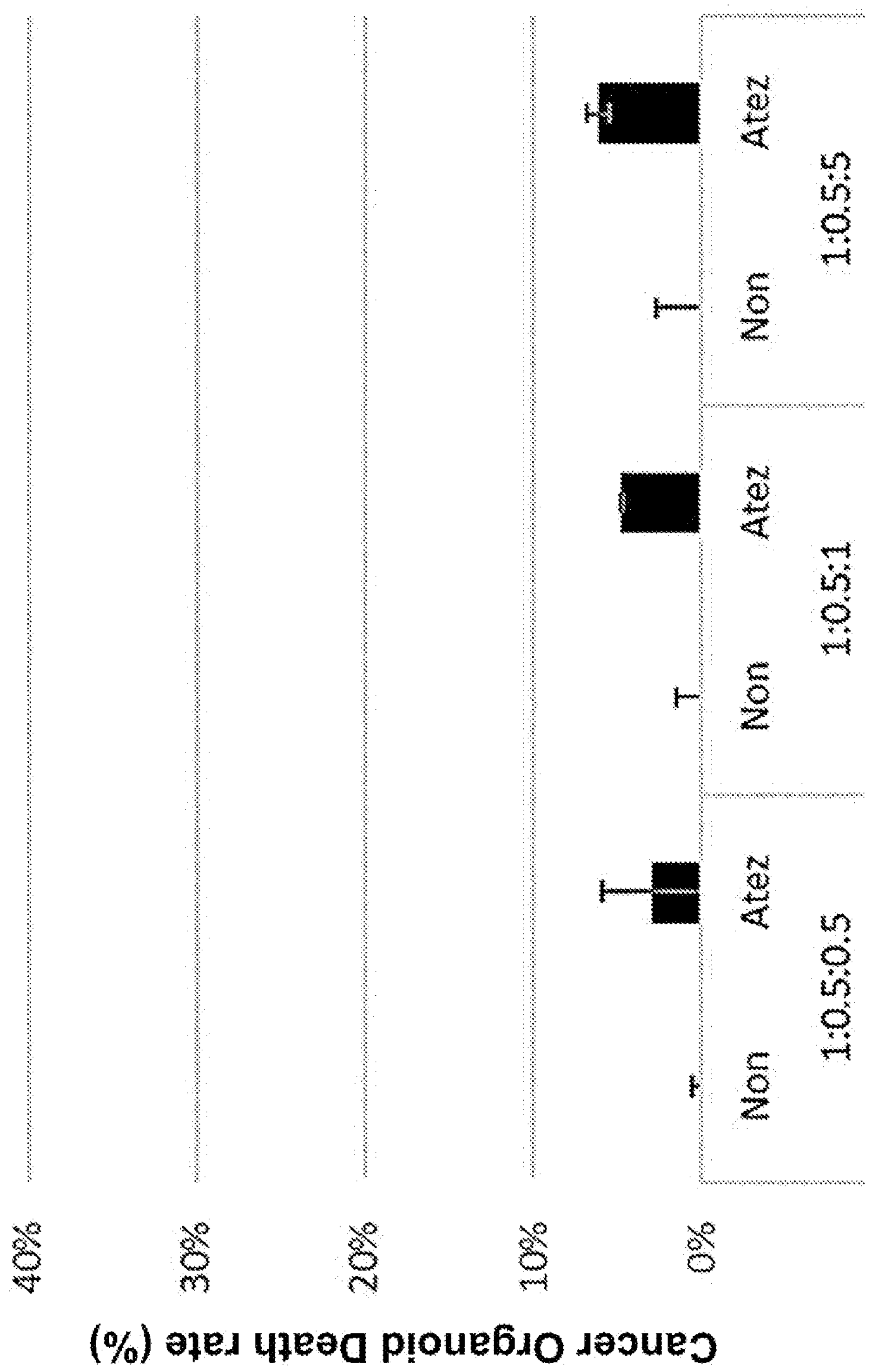

FIG. 32 is a graph showing the death rate of lung cancer organoids according to each co-culture ratio of lung cancer organoids, CD8+ T cells and DCs, and it relates to the result of co-culture in the mixed condition in which lung cancer organoids and CD8+ T cells were fixed in the cell number ratio of 1:0.5. 'Non' refers to a drug-untreated group, and 'Atez' refers to a drug-treated group treated with an atezolizumab as an exemplary drug. The death rate was analyzed based on the results of measuring the growth rate after 72 hours (72 h) of drug treatment.

Figure 33:
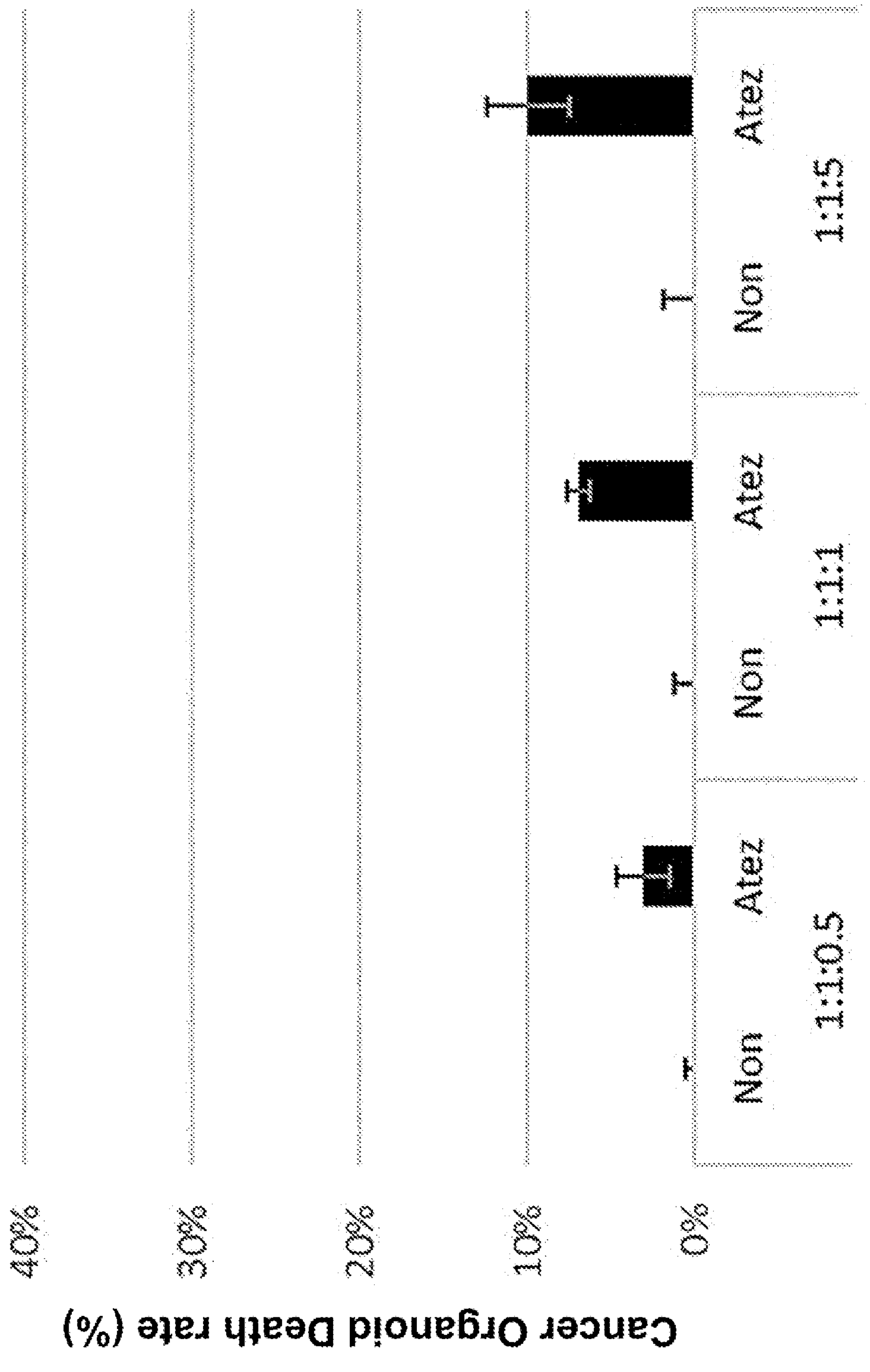

FIG. 33 is a graph showing the death rate of lung cancer organoids according to each co-culture ratio of lung cancer organoids, CD8+ T cells and DCs, and it relates to the result of co-culture in the mixed condition in which lung cancer organoids and CD8+ T cells were fixed in the cell number ratio of 1:1. 'Non' refers to a drug-untreated group, and 'Atez' refers to a drug-treated group treated with an atezolizumab as an exemplary drug. The death rate was analyzed based on the results of measuring the growth rate after 72 hours (72 h) of drug treatment.

Figure 34:
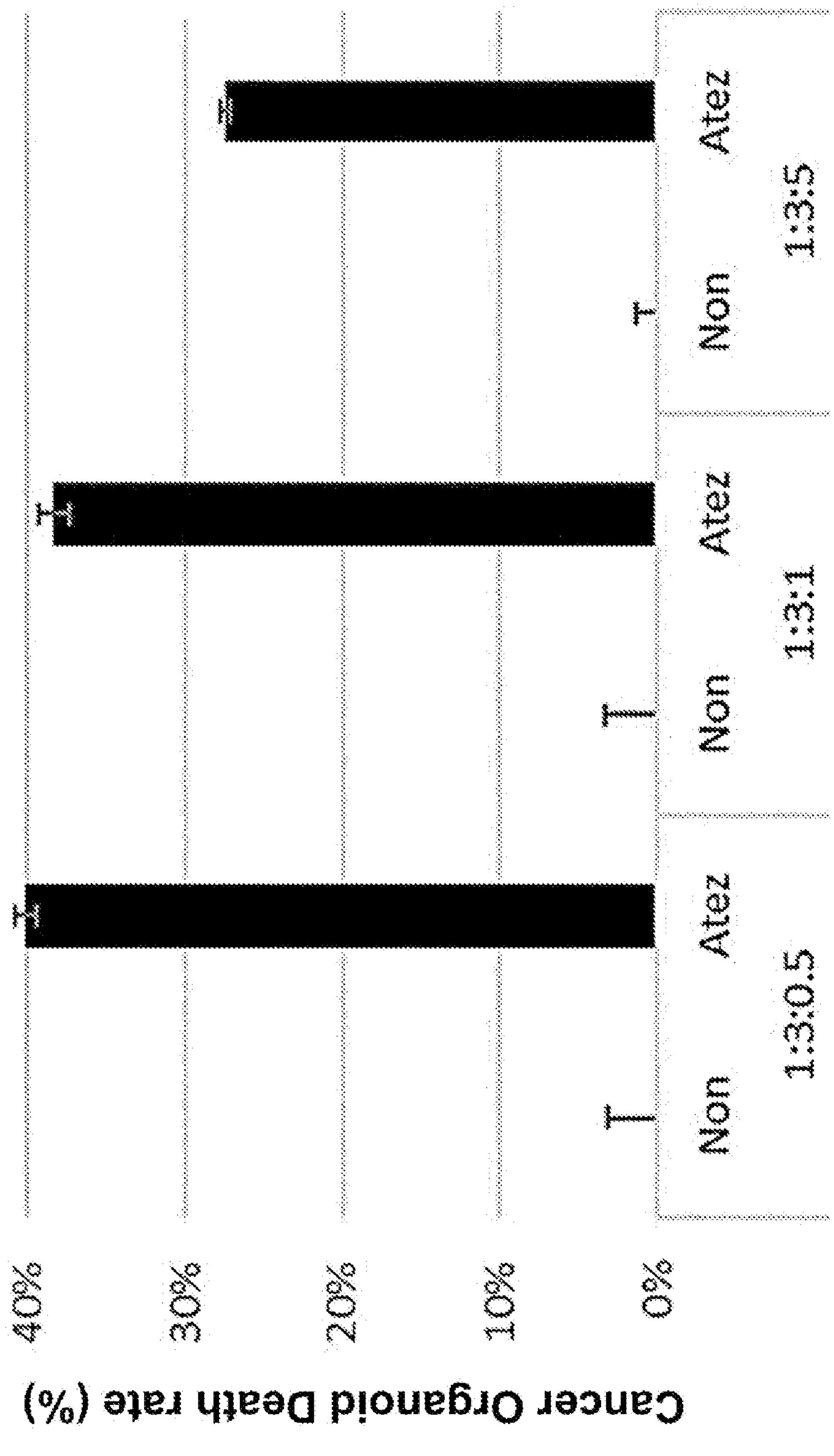

FIG. 34 is a graph showing the death rate of lung cancer organoids according to each co-culture ratio of lung cancer organoids, CD8+ T cells and DCs, and it relates to the result of co-culture in the mixed condition in which lung cancer organoids and CD8+ T cells were fixed in the cell number ratio of 1:3. 'Non' refers to a drug-untreated group, and 'Atez' refers to a drug-treated group treated with an atezolizumab as an exemplary drug. The death rate was analyzed based on the results of measuring the growth rate after 72 hours (72 h) of drug treatment.

EXAMPLES

Specific examples will be described to help the understanding of the present invention. However, the following examples should not be construed as limiting the present invention.

Example 1. Anticancer Drug Efficacy Evaluation and Screening System Comprising Cancer Organoids, Cytotoxic T Cells and M1 Macrophages The inventors have established an in vitro screening system that can accurately predict the efficacy of a drug when administered to a subject, by similarly reproducing the environment in which cancer exists in the body.

Specifically, a co-culture system in which cancer organoids, cytotoxic T cells (hereinafter referred to as 'CD8+ T cells') and M1 macrophages (classically activated macrophages, hereinafter referred to as 'M1') coexist was used, and the ratio of organoid or cell that satisfies the following three conditions during the co-culture was confirmed, respectively:

(1) A condition under which death rate of cancer organoids and M1 is low (the efficacy of the drug cannot be accurately analyzed if death of the cancer organoids or M1 is observed to be high in the drug-untreated group when co-culturing the organoids, CD8+ T cells and M1)

(2) A condition under which phagocytosis is activated (3) A condition under which the efficacy of drugs can be evaluated even though the MoA (mode of action) thereof is different from each other In addition, when the number of organoids or cells in the ratio of cancer organoids, CD8+ T cells and M1 was set to 1 for $5.0\times10^3$, the specific number of organoids or cells according to the ratio is as follows:

0.2=1.0×$10^3$ of organoids or cells
0.5=2.5×$10^3$ organoids or cells
1=5.0×$10^3$ organoids or cells
3=15.0×$10^3$ organoids or cells
5=25.0×$10^3$ organoids or cells
10=50.0×$10^3$ organoids or cells The ratio of cancer organoids, CD8+ T cells and M1 satisfying all of the conditions described above was confirmed in Examples 1.1 to 1.3 below.

Example 1.1. Establishment of Conditions in which Cancer Organoids, Cytotoxic T Cells and M1 Macrophages Coexist When co-culturing cancer organoids, CD8+ T cells and M1, it is difficult to accurately evaluate the efficacy of the drug if anyone among them dies. Therefore, in this Example 1.1, the inventors tried to establish conditions in which all of them survive when cancer organoids, CD8+ T cells, and M1 are co-cultured in the absence of drug treatment.

Specifically, cancer organoids, CD8+ T cells and M1 derived from colorectal cancer patients were used. As shown in Table 1 below, the ratio for cancer organoids was fixed to 1, and the ratio for CD8+ T cells was set to 0.1 to 10 and the ratio for M1 was set to 0.1 to 5. Then, they were co-cultured for 2 hours, and the death rate of cancer organoids or cells was analyzed at each ratio. The analysis was performed by flow-cytometer, and CFSE (+) was used as a cancer organoid marker and CD11B (+) was used as an M1 macrophage marker.

TABLE 1

| Group | Cancer Organoid | T cell | Macrophage |
|---|---|---|---|
| G1 | 1 | 0.2 | 0.5 |
| G2 | 1 | 0.2 | 1 |
| G3 | 1 | 0.2 | 3 |
| G4 | 1 | 0.5 | 0.5 |
| G5 | 1 | 0.5 | 1 |
| G6 | 1 | 0.5 | 3 |
| G7 | 1 | 3 | 0.5 |
| G8 | 1 | 3 | 1 |
| G9 | 1 | 3 | 3 |

Figure 1A:
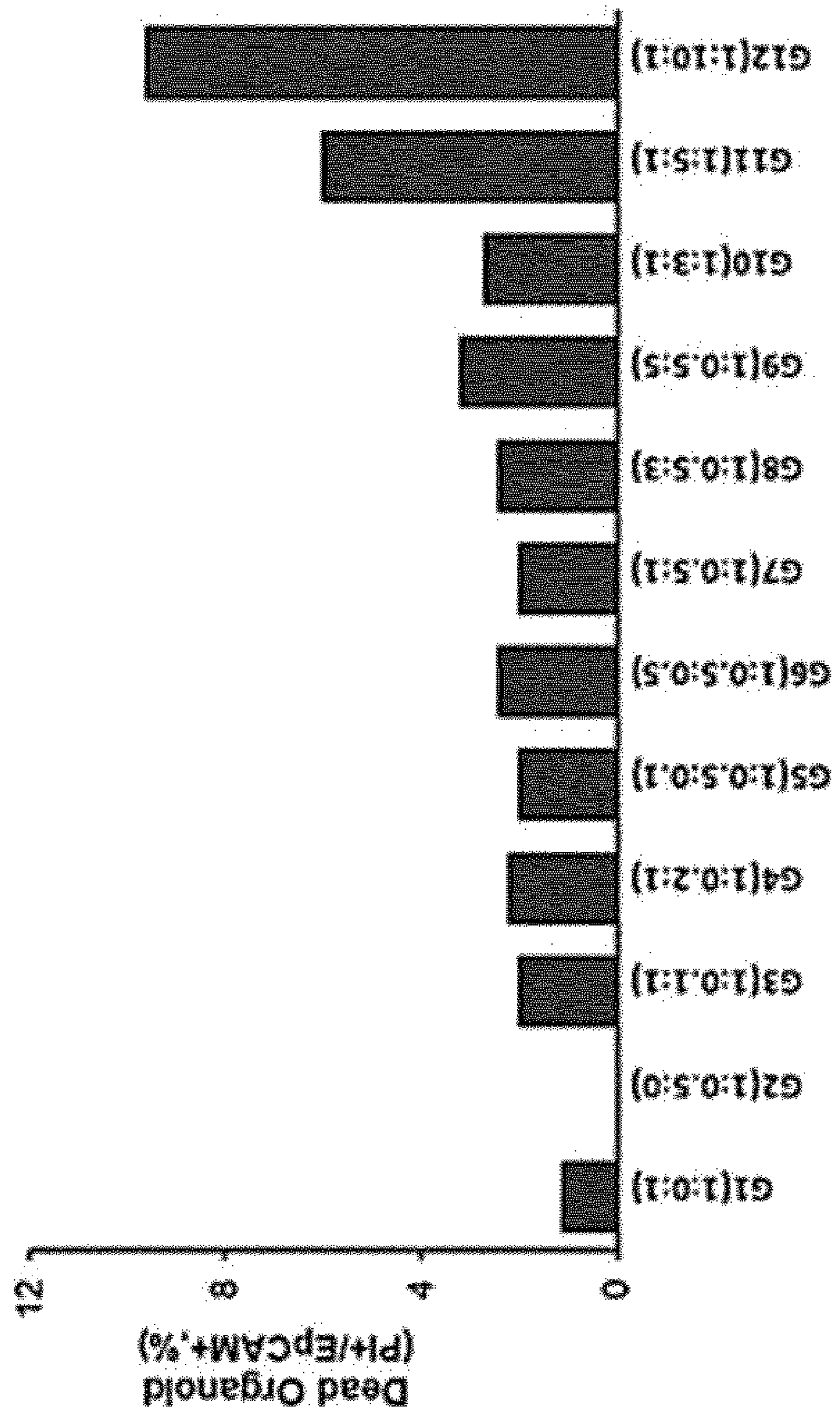
FIG. 1*a* is a graph showing the degree of death of cancer organoids according to the ratio of cytotoxic T cells (hereinafter referred to as 'CD8+ T cells') and M1 macrophages (classically activated macrophage, M1, hereinafter referred to as 'M1').
Figure 1B:
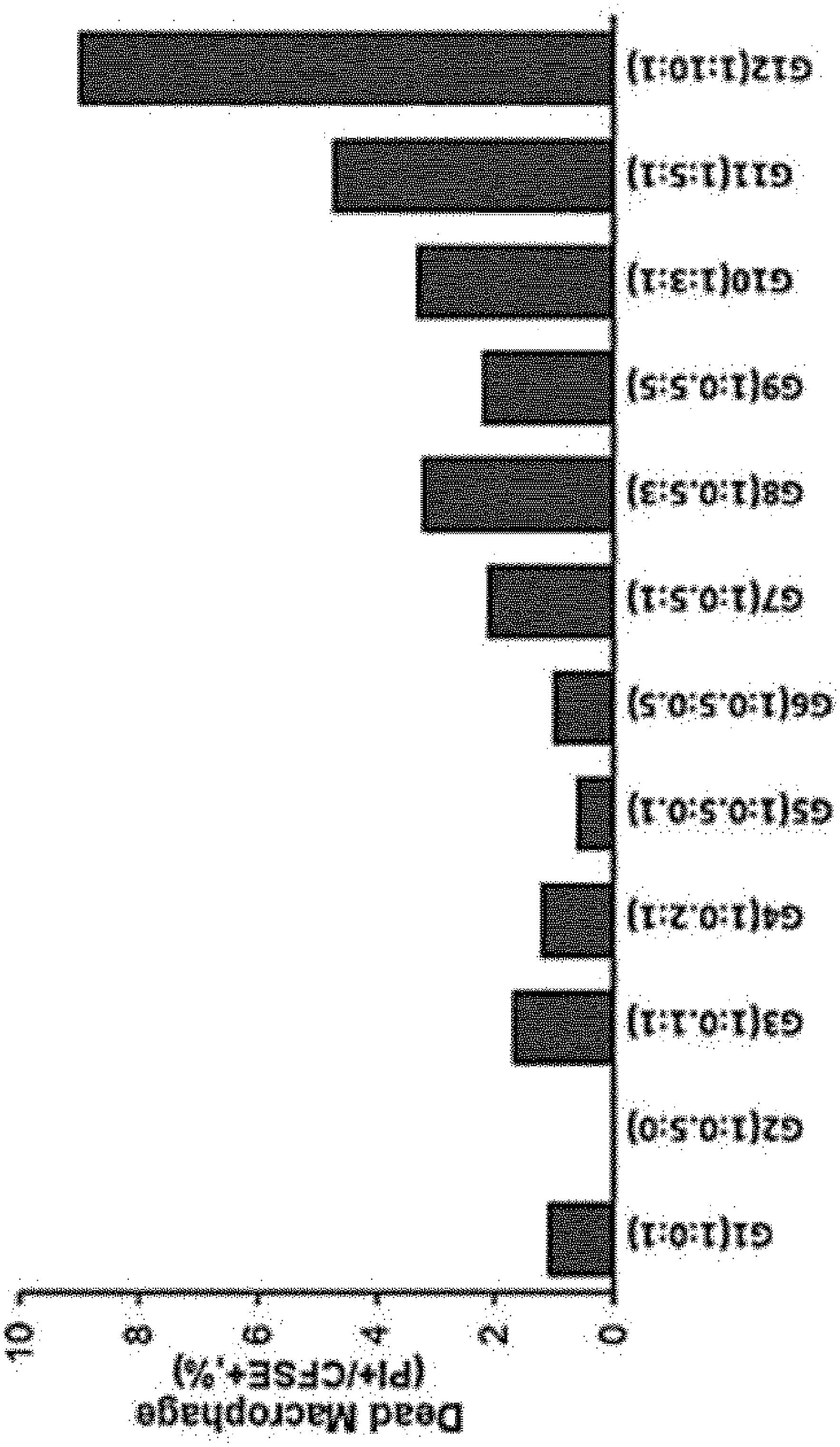
FIG. 1*b* is a graph showing the degree of death of M1 according to the ratio of cytotoxic T cells and M1 macrophages.

As a result, as shown in FIG. 1*a*, a high death rate of cancer organoids was observed in Groups 11 and 12 with a high CD8+ T cell ratio (5 or more) and in Group 9 with a high M1 ratio (5 or more). In addition, as shown in FIG. 1*b*, it was confirmed that a high death rate of M1 macrophages occurred under conditions in which the ratio of CD8+ T cells was high (5 or more) in Groups 11 and 12.

Taken together, it was confirmed that the conditions of Groups 3, 4, 5, 6, 7, 8 and 10 allowed cancer organoids, CD8+ T cells and M1 to survive in balance without the drug treatment.

Therefore, it was found that when the ratio of cancer organoids is 1, setting the ratio of CD8+ T cells to 3 or less and the ratio of M1 to 3 or less was the most optimal ratio for the anticancer drug screening system.

Example 1.2. Confirmation of Growth Inhibition and Death of Cancer Organoid Depending on Co-Culture Time In the screening system composed of cancer organoids, CD8+ T cells and M1 as confirmed in Example 1.1, the inventors confirmed the ratio of cells in which growth inhibition and death of cancer organoids were not observed. For this, after setting different co-culture times (24 hours, 48 hours and 72 hours), the degree of cancer organoid growth was analyzed.

Specifically, as shown in Table 2 below, the ratio for cancer organoids was fixed to 1, and the ratio for CD8+ T cells was set to 0.2 to 3 and the ratio for M1 was set to 0.1 to 3. Then, they were co-cultured, and phagocytosis was analyzed at each ratio. Herein, the ratio of the CD8+ T cells and M1 was tested in a narrower range than the ratio applied in Example 1.1, and the analysis was performed by HCS (High-Content Screening). The area of the initial organoid was set to 100%, and the change in area depending on the reaction time was expressed as %.

TABLE 2

| Group | Cancer Organoid | T cell | Macrophage |
|---|---|---|---|
| G1 | 1 | 0 | 1 |
| G2 | 1 | 0.5 | 0 |
| G3 | 1 | 0.1 | 1 |
| G4 | 1 | 0.2 | 1 |
| G5 | 1 | 0.5 | 0.1 |
| G6 | 1 | 0.5 | 0.5 |
| G7 | 1 | 0.5 | 1 |
| G8 | 1 | 0.5 | 3 |
| G9 | 1 | 0.5 | 5 |
| G10 | 1 | 3 | 1 |
| G11 | 1 | 5 | 1 |
| G12 | 1 | 10 | 1 |

Figure 2:
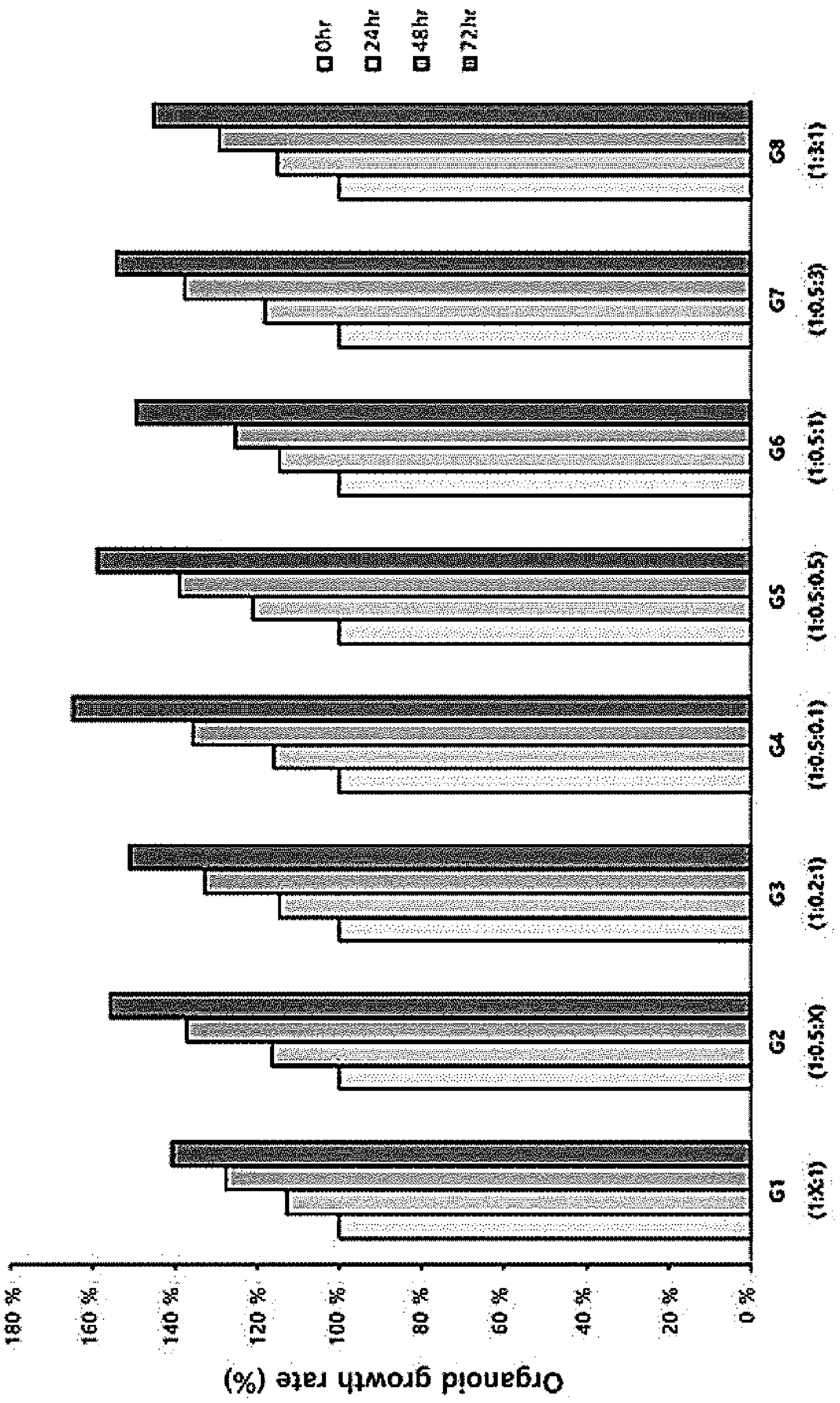
FIG. 2 is a graph showing the degree of growth inhibition of cancer organoids according to the CD8+ T cells and M1 ratio, and relates to the results of co-culture for 0 hours, 24 hours, 48 hours and 72 hours.

As a result, as shown in FIG. 2, although the degree of growth varies depending on the cell ratio, it was confirmed that the growth of cancer organoids was not inhibited even when co-cultured for 72 hours or more at the above ratio. Through the above results, it was found that setting the ratio of cancer organoids, CD8+ T cells and M1 to 1:0.2 to 3:0.1 to 3 is the most optimal ratio for an anticancer drug screening system.

Example 1.3. Establishment of Conditions in which Phagocytosis is Activated

In order to confirm whether the screening system composed of cancer organoids, CD8+ T cells and M1 as confirmed in Example 1.1 can be used to evaluate the efficacy of a drug targeting M1, the inventors treated the system with anti-CD47 antibody, and then observed the death rate of cancer organoids according to phagocytosis.

Specifically, cancer organoids and CD8+ T cells derived from colorectal cancer patients were used, and CHA15 cell line was used as M1.

In addition, as shown in Table 2 above, the ratio for cancer organoids was fixed to 1, and the ratio for CD8+ T cells was set to 0.2 to 3 and the ratio for M1 was set to 0.1 to 3. Then, they were co-cultured, and phagocytosis was analyzed at each ratio. Herein, the ratio of the CD8+ T cells and M1 was tested in a narrower range than the ratio applied in Example 1.1, and the analysis was performed by flow-cytometer. EpCAM(+) was used as a cancer organoid marker, and CD11B (+) was used as an M1 marker. Phagocytosis was confirmed by the double positive ratio of cancer organoid marker and M1 marker.

Figure 3:
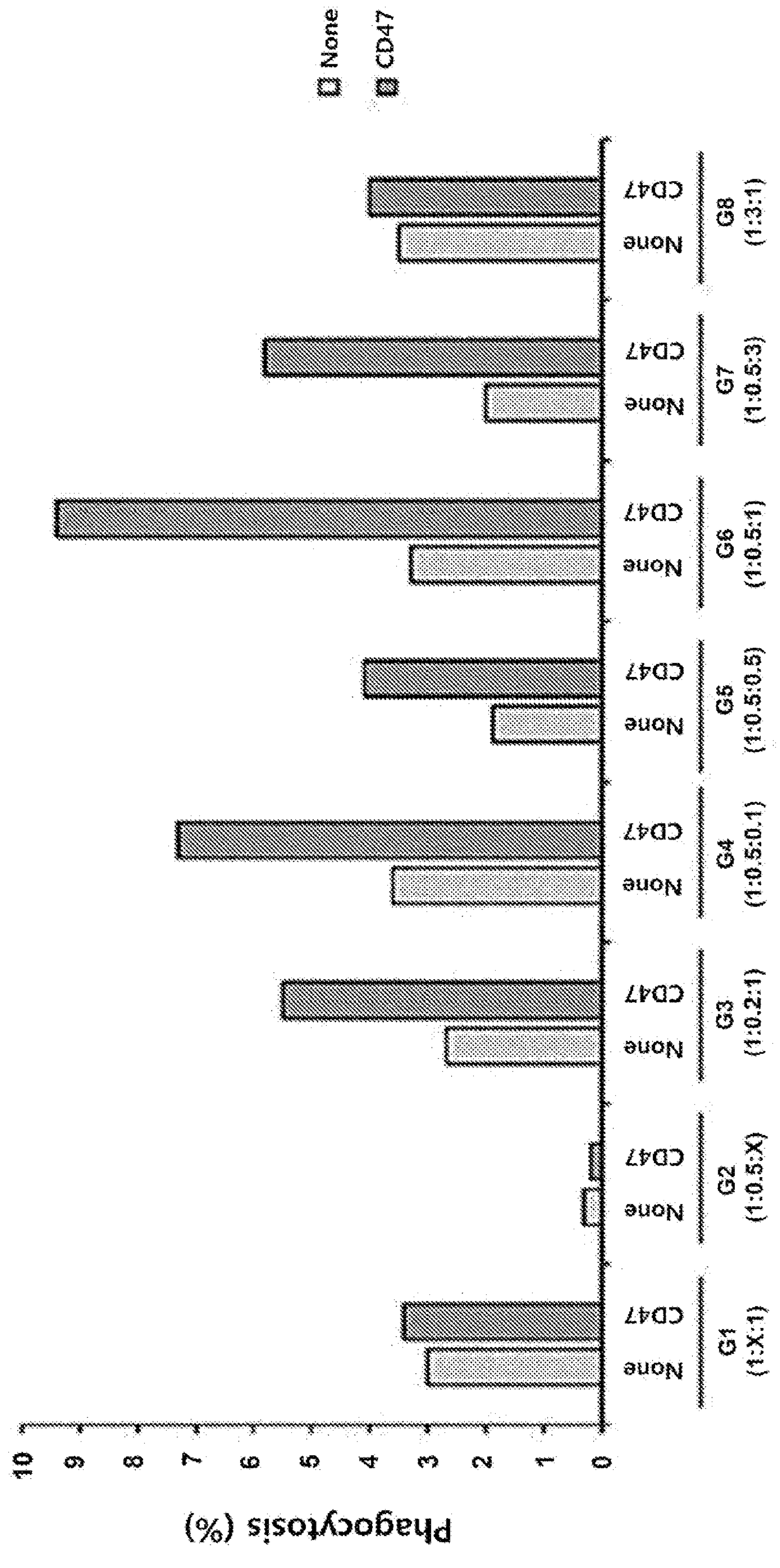
FIG. 3 is a graph showing the degree of phagocytosis activation by anti-CD47 antibody treatment.

As a result, as shown in FIG. 3, phagocytosis was observed in all conditions except for Group 2 in which M1 did not exist. In particular, when treating with the anti-CD47 antibody binding to M1 in Groups 3, 4, 6 and 7, it was confirmed that phagocytosis was activated compared to the untreated group.

Through the above results, it was found that setting the ratio of cancer organoids, CD8+ T cells and M1 to 1:0.2 to 0.5:0.1 to 3 is the most optimal ratio for an anticancer drug screening system.

Example 1.4. Establishment of Conditions to Evaluate the Efficacy of Drugs with Different MoA (Mode of Action)

In order to confirm whether the screening system composed of cancer organoids, CD8+ T cells and M1 as confirmed in Example 1.1 can be used to evaluate the efficacy of a drug, the death rate of cancer organoids by phagocytosis was observed after treating the system with an anti-PD-L1 antibody atezolizumab previously used as an immuno-anticancer drug, anti-CD47 antibody and a combination thereof.

Atezolizumab activates CD8+ T cells by binding to PD-L1 on cancer cells and blocking the PD-1/PD-L1 mechanism, and anti-CD47 antibody activates macrophages by binding to CD47 of M1 and blocking the SIRP-a/CD47 mechanism. Thus, the inventors confirmed whether the screening system of the present invention can evaluate the efficacy of all types of drugs acting in different mechanisms.

Specifically, cancer organoids and CD8+ T cells derived from colorectal cancer patients were used, and CHA15 cell line was used as M1.

In addition, as shown in Table 2 above, the ratio for cancer organoids was fixed to 1, and the ratio for CD8+ T cells was set to 0 to 3 and the ratio for M1 was set to 0 to 3. Then, they were co-cultured, and treated with 10 nM of Atezolizumab (Selleck, #A2004) which is anti-PD-L1 antibody and/or 10 nM of anti-CD47 antibody. After that, the death rate of cancer organoids or M1 was analyzed at each ratio. Herein, the ratio of the CD8+ T cells and M1 was tested in a narrower range than the ratio applied in Example 1.1, and the changes in organoid area for 72 hours after drug treatment was analyzed by HCS (High-Content Screening). After 72 hours from drug treatment, the overall efficacy was evaluated by calculating the change in the organoid area of the drug-treated group compared to the organoid area of the non-treated group.

Figure 4:
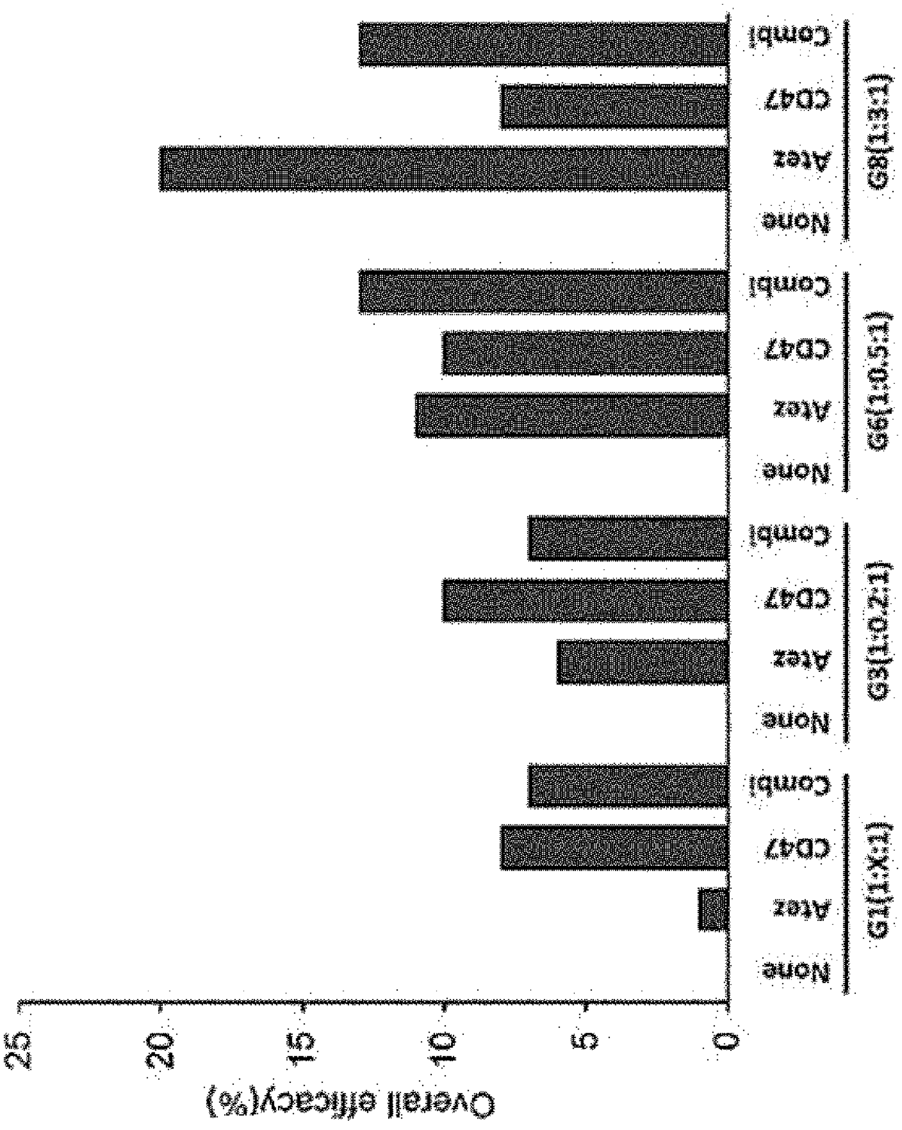
FIG. 4 is a graph showing overall efficacy of drugs for death of cancer organoids according to an increase in the ratio of CD8+ T cells.

As a result, FIG. 4 shows that the overall efficacy increased as the ratio of CD8+ T cells increased in Groups 1, 3, 6 and 8 wherein the ratios of cancer organoids and M1 are fixed to 1 and 1 respectively, and the ratio of CD8+ T cells changes. In particular, it was confirmed that the growth inhibition and death of cancer organoids appeared to be high in the atezolizumab-treated group.

Figure 5:
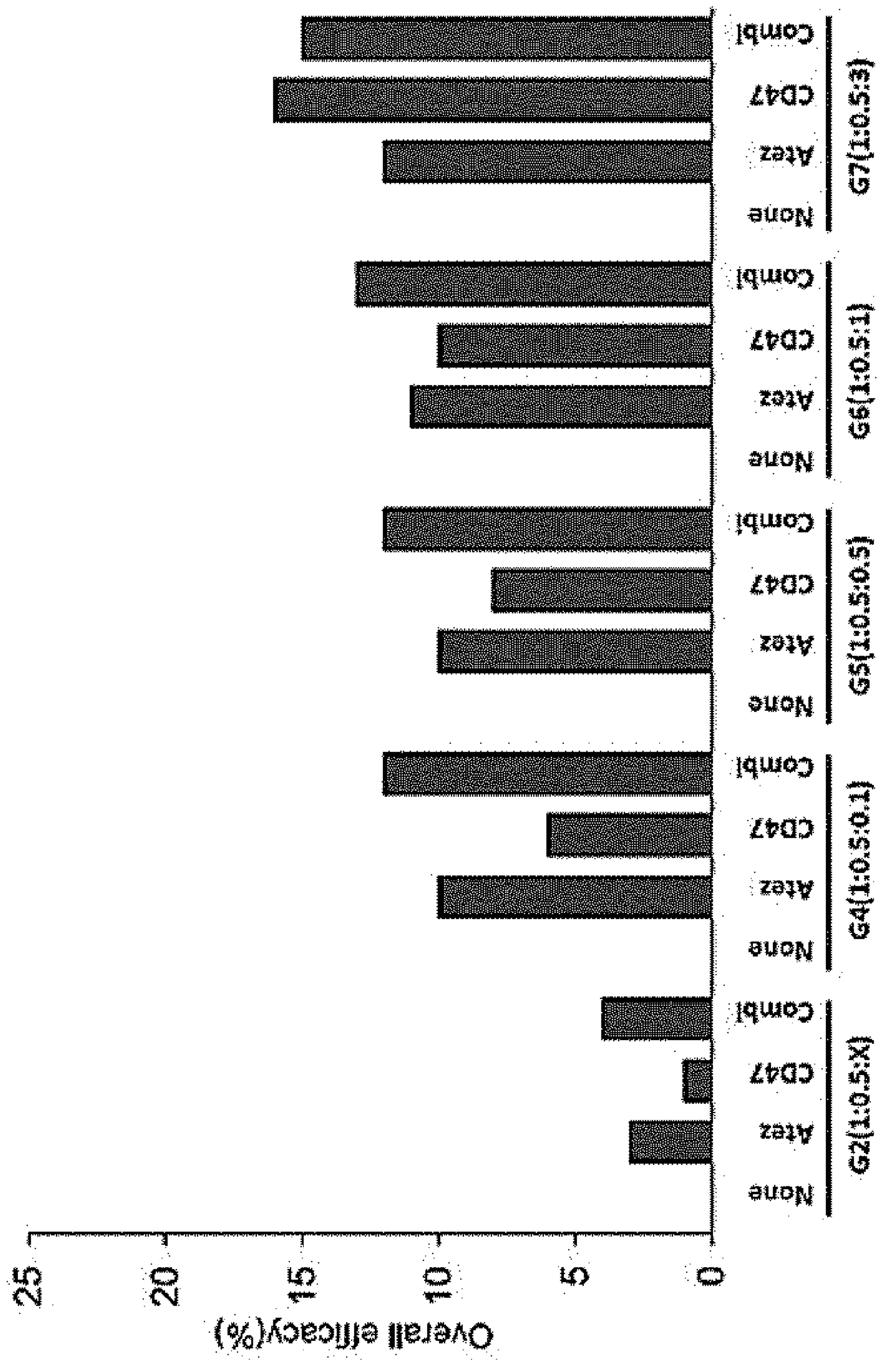
FIG. 5 is a graph showing the overall efficacy of drugs for death of cancer organoids according to an increase in the M1 ratio.

Also, FIG. 5 shows that the overall efficacy increased as the ratio of M1 increased in Groups 2, 4, 5, 6 and 7 wherein the ratios of cancer organoids and CD8+ T cells are fixed to 1 and 0.5 respectively, and the ratio of M1 changes. In particular, it was confirmed that the growth inhibition and death of cancer organoids appeared to be high in the anti-CD47 antibody-treated group.

Figure 6:
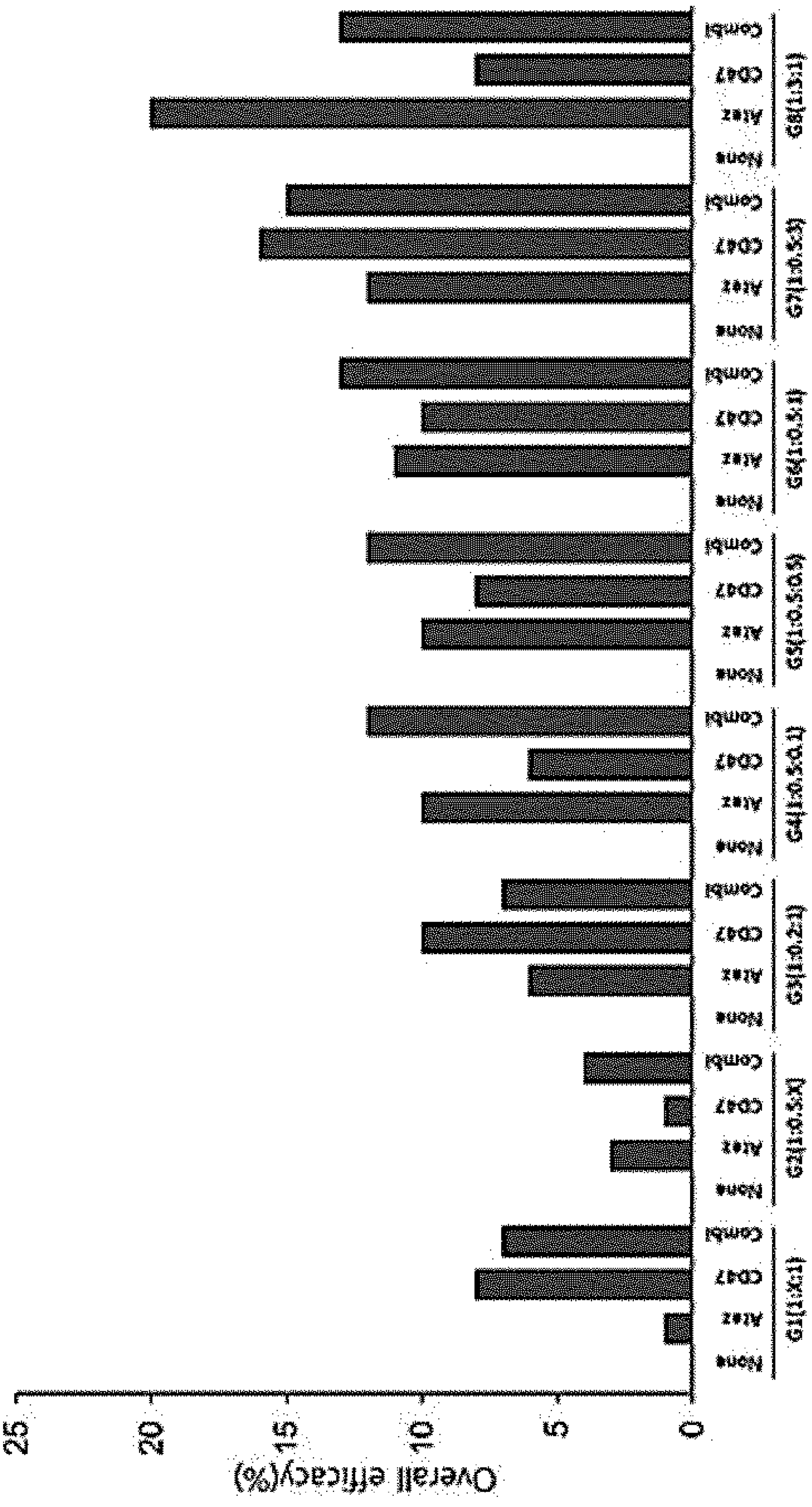
FIG. 6 is a graph showing the overall efficacy of the drugs for death of cancer organoids

As shown in FIG. 6, it was confirmed that Groups 5, 6 and 7 exhibited similar and high killing effects of cancer organoids by the use of atezolizumab alone, anti-CD47 antibody alone and combination thereof.

Taking the results of Examples 1.1 to 1.3 together, it was confirmed that the ratio for co-culture of cancer organoids, CD8+ T cells and M1 under which the growth of cancer organoids is not suppressed, the death of cancer organoids and M1 is not caused, and the treatment with different mechanism of drugs alone or in combination exhibits similarly overall efficacy is 1:0.5:0.5 in Group 5, 1:0.5:1 in Group 6, and 1:0.5:3 in Group 7.

Example 2. Anticancer Drug Efficacy Evaluation and Screening System Comprising Cancer Organoids, M1 Macrophages and M2 Macrophages The inventors have established an in vitro efficacy evaluation and screening system that can accurately predict the efficacy of a drug when administered to a subject, by similarly reproducing the environment in which cancer exists in the body.

Specifically, in order to establish a co-culture system in which cancer organoids, M1 macrophages (classically activated macrophages, hereinafter referred to as 'M1') and M2 macrophages (alternatively activated macrophages, hereinafter referred to as 'M2') coexist, the inventors set a mixing ratio satisfying co-culture conditions under which (1) cancer organoids grow properly and (2) drug efficacy is well observed.

As shown in Table 3 below, the ratio for cancer organoids was fixed to 1, and the ratio for M1 was set to 0.5 to 3 and the ratio for M2 was set to 0.5 to 5. Herein, the number of organoids or cells was set to 1 for $5.0\times10^3$.

TABLE 3

| Group | Cancer Organoid | M1 | M2 |
|---|---|---|---|
| 1 | 1 | 3 | 0 |
| 2 | | 0 | 5 |
| 3 | | 0.5 | 0.5 |
| 4 | | | 1 |
| 5 | | | 3 |
| 6 | | | 5 |
| 7 | | 1 | 0.5 |
| 8 | | | 1 |
| 9 | | | 3 |
| 10 | | | 5 |
| 11 | | 3 | 0.5 |
| 12 | | | 1 |
| 13 | | | 3 |
| 14 | | | 5 |

Cancer organoids were prepared to have a 3D structure by isolating lung cancer tissues obtained from patients into single cells and culturing them together with ECM (extracellular matrix). The formed cancer organoids were confirmed to be tumors through pathological analysis, and used after being isolated into single cells using Tryp-LE. M1 and M2 differentiated from iPSCs were used, and M1 or M2 was differentiated from H9 cell line using a general method known in the art.

Example 2.1. Conditions for Proper Growth of Cancer Organoids

The inventors confirmed a mixing ratio of cancer organoids, M1 and M2, which allows cancer organoids to grow properly even when co-cultured with immune cells.

Specifically, after co-culturing at the mixing ratio according to Table 3 above, the area of cancer organoids was measured immediately after the start of the co-culture (0 h), after 24 hours (24 h), after 48 hours (48 h) and after 72 hours (72 h), respectively, and the growth rate was analyzed by the following formula.

$$*\text{Cancer organoid growth rate (\%)} = \left(\text{area after cancer organoids after 24, 48, or 72 hours of co-culture}\right) / \left(\text{area of cancer organoids immediately after the start of the co-culture}\right) \times 100$$

Figure 7A:
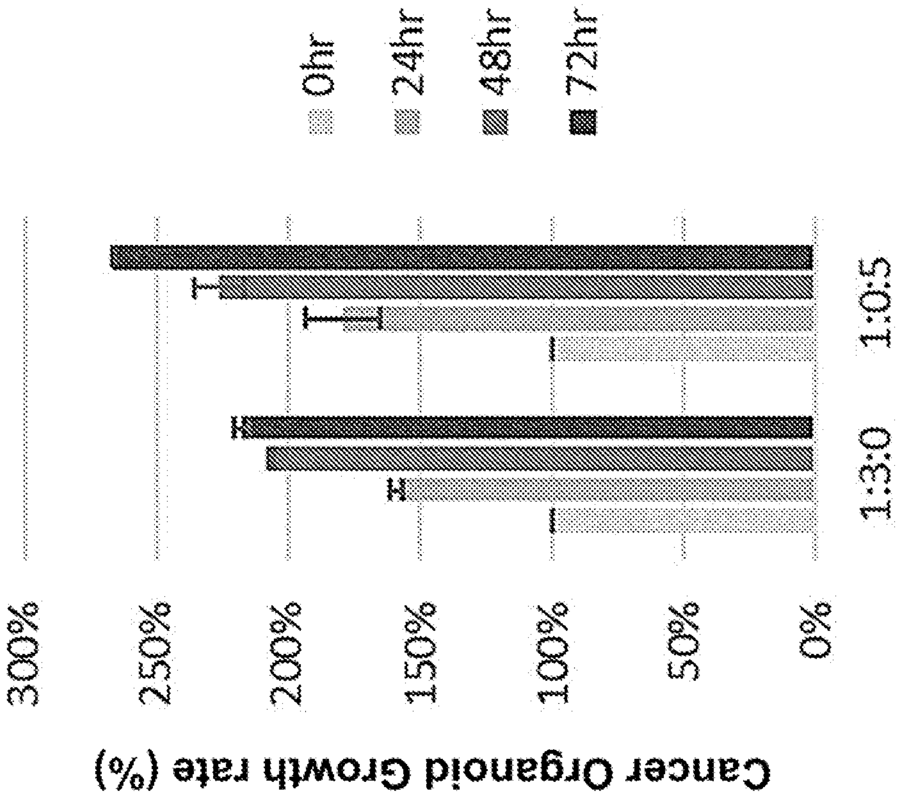
FIG. 7*a* is a graph showing the growth rate of cancer organoids according to the co-culture ratio of cancer organoids, M1 and M2 macrophages (classically activated macrophage, M2, hereinafter referred to as 'M2'), and it relates to the result of co-culture under the conditions without M1 ("1:3:0") or without M2 ("1:0:5").
Figure 7B:
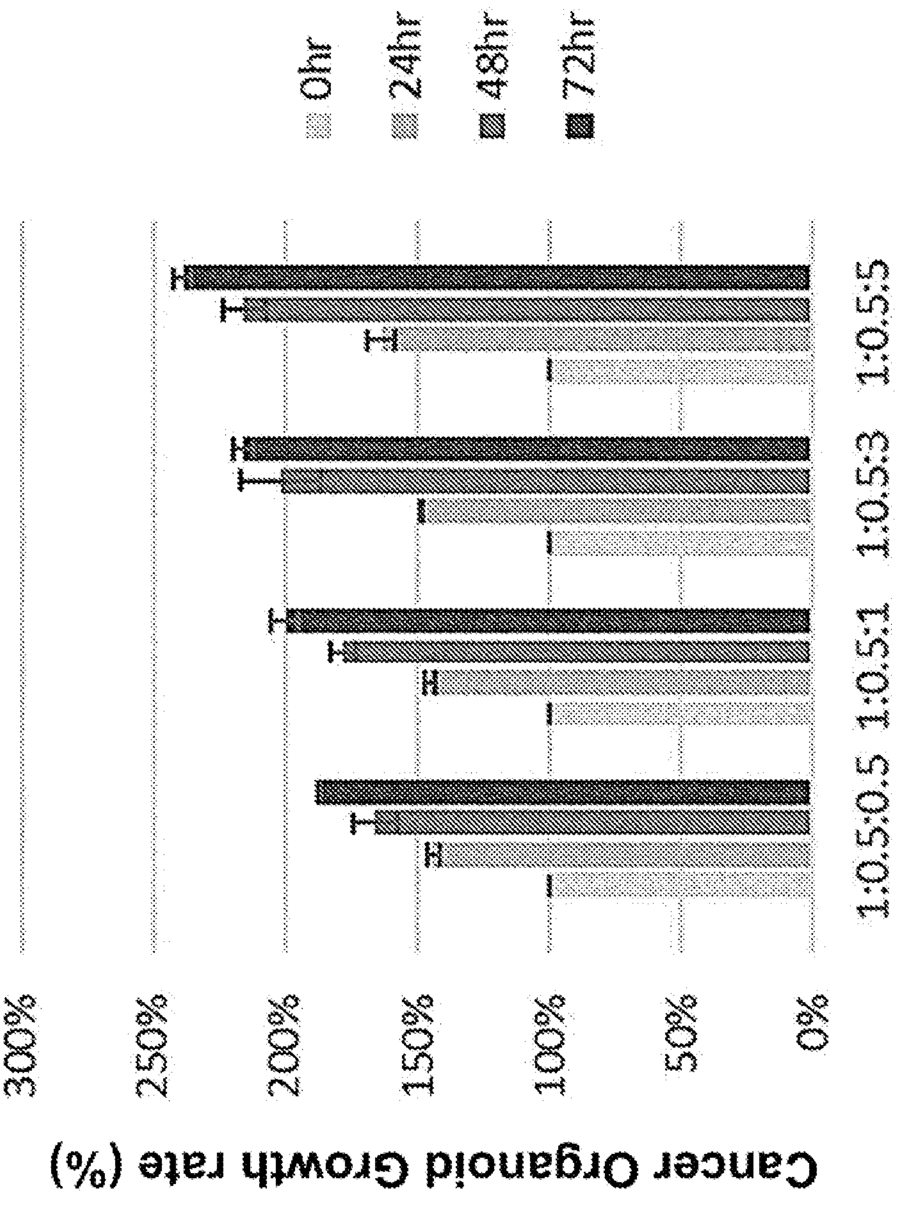
FIG. 7*b* is a graph showing the growth rate of cancer organoids according to the co-culture ratio of cancer organoids, M1 and M2, and it relates to the result of co-culture in the mixed condition in which cancer organoids and M1 were fixed in the cell number ratio of 1:0.5.
Figure 7C:
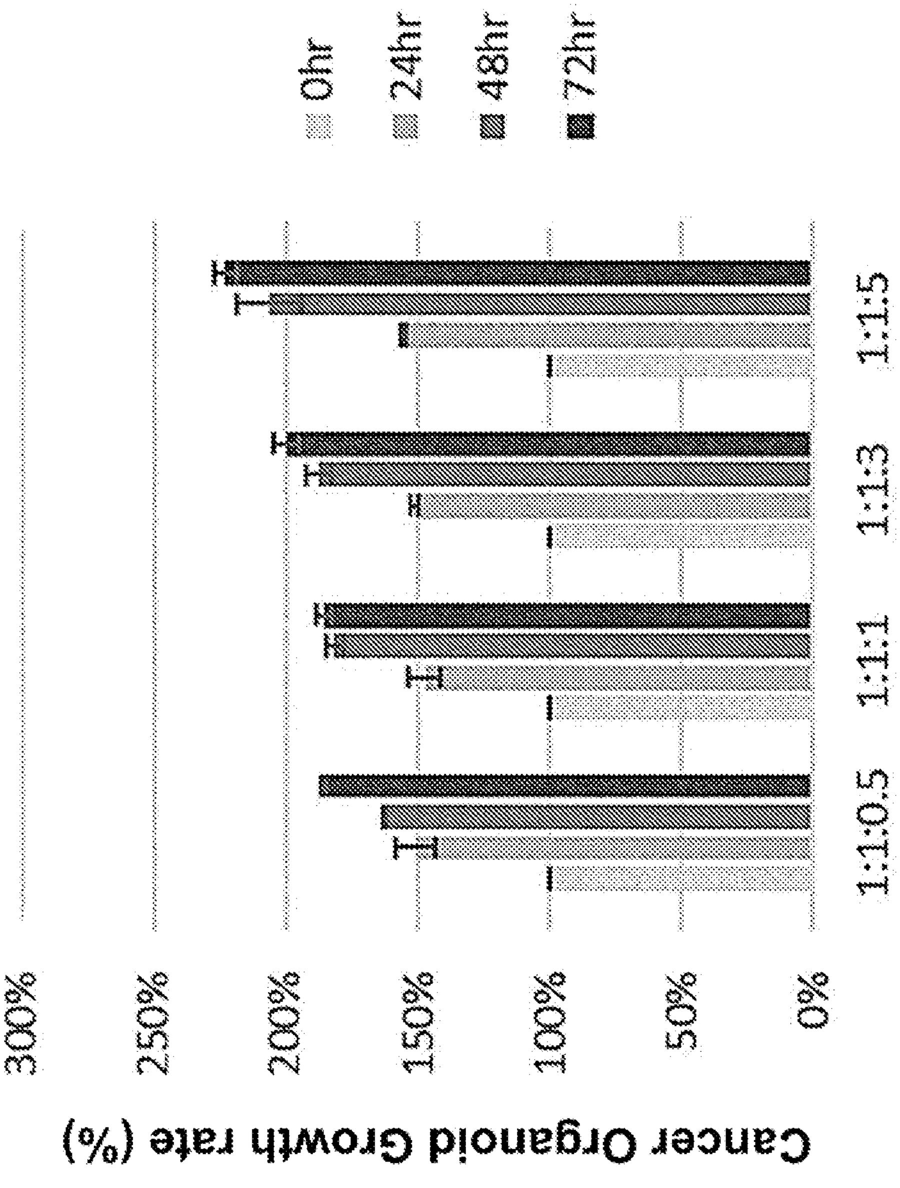
FIG. 7*c* is a graph showing the growth rate of cancer organoids according to the co-culture ratio of cancer organoids, M1 and M2, and it relates to the result of co-culture in the mixed condition in which cancer organoids and M1 were fixed in the cell number ratio of 1:1.
Figure 7D:
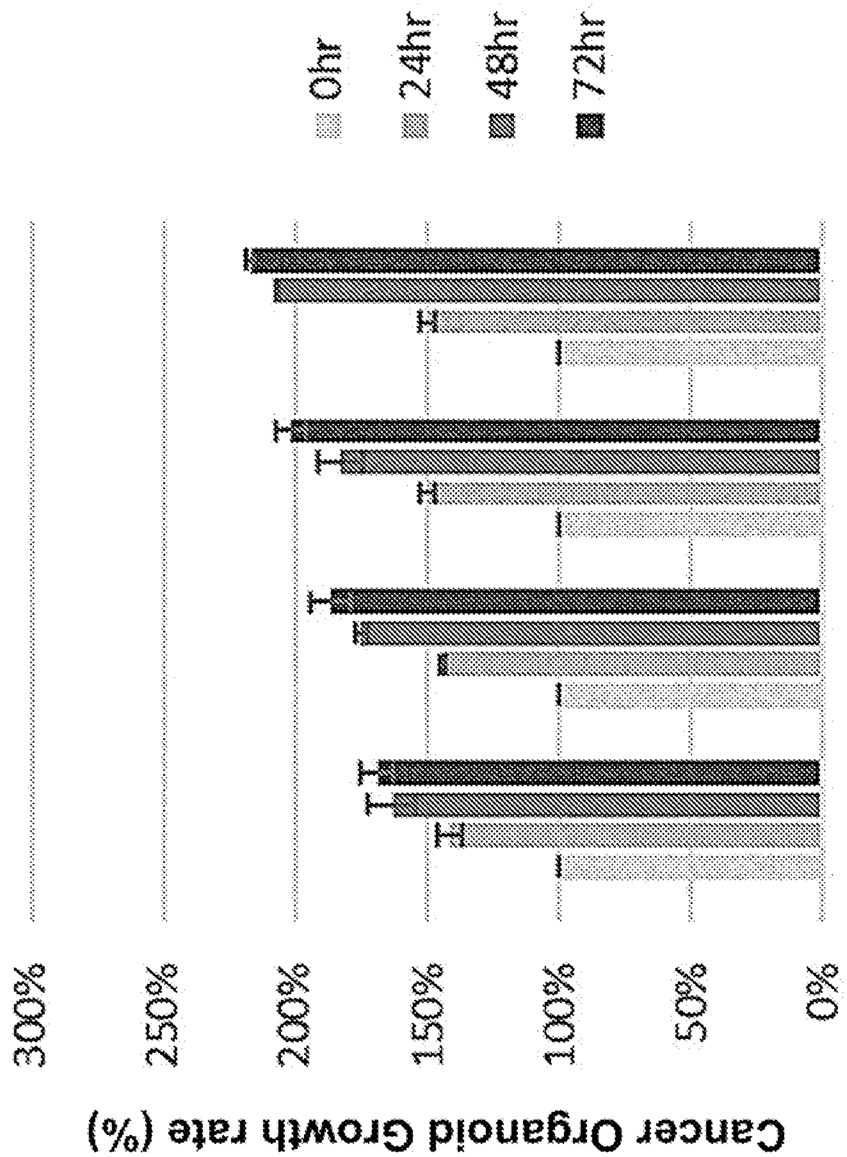
FIG. 7*d* is a graph showing the growth rate of cancer organoids according to the co-culture ratio of cancer organoids, M1 and M2, and it relates to the result of co-culture in the mixed condition in which cancer organoids and M1 were fixed in the cell number ratio of 1:3.

As a result, FIGS. 7*a* to 7*c* show that the growth of cancer organoids was not inhibited at all mixing ratios, and the growth rate of cancer organoids tended to increase as the ratio of M2 increased.

Example 2.2. Conditions in which Drug Efficacy is High

The inventors confirmed a mixing ratio of cancer organoids, M1 and M2, which makes the efficacy of the anticancer drug high.

Specifically, for the co-cultures of cancer organoids, M1 and M2 according to the mixing ratio in Table 3 above, those not treated with the drug were set as the control group (hereinafter referred to as 'drug-untreated group'), and those treated with an anti-CD47 antibody targeting M1 as an exemplary drug were set as the experimental group (hereinafter referred to as 'drug-treated group'). After co-culturing them for 72 hours, the growth rate was measured after 72 hours of drug treatment (72 h), and the death rate was analyzed by the following method through the measured growth rate.

Cancer organoid death rate (%) = [1 − (growth rate of cancer organoids in the drug-treated group*)/(growth rate of cancer organoids in the drug-untreated group**)] × 100

Growth rate of cancer organoids in the drug-treated group (%) = (cancer organoid area after 72 hours of drug treatment)/(cancer organoid area immediately after the start of the co-culture (0 h) × 100

Growth rate of cancer organoids in the drug-untreated group (%) = (cancer organoid area after 72 hours without drug treatment)/(cancer organoid area immediately after the start of the co-culture (0 h) × 100

Figure 8A:
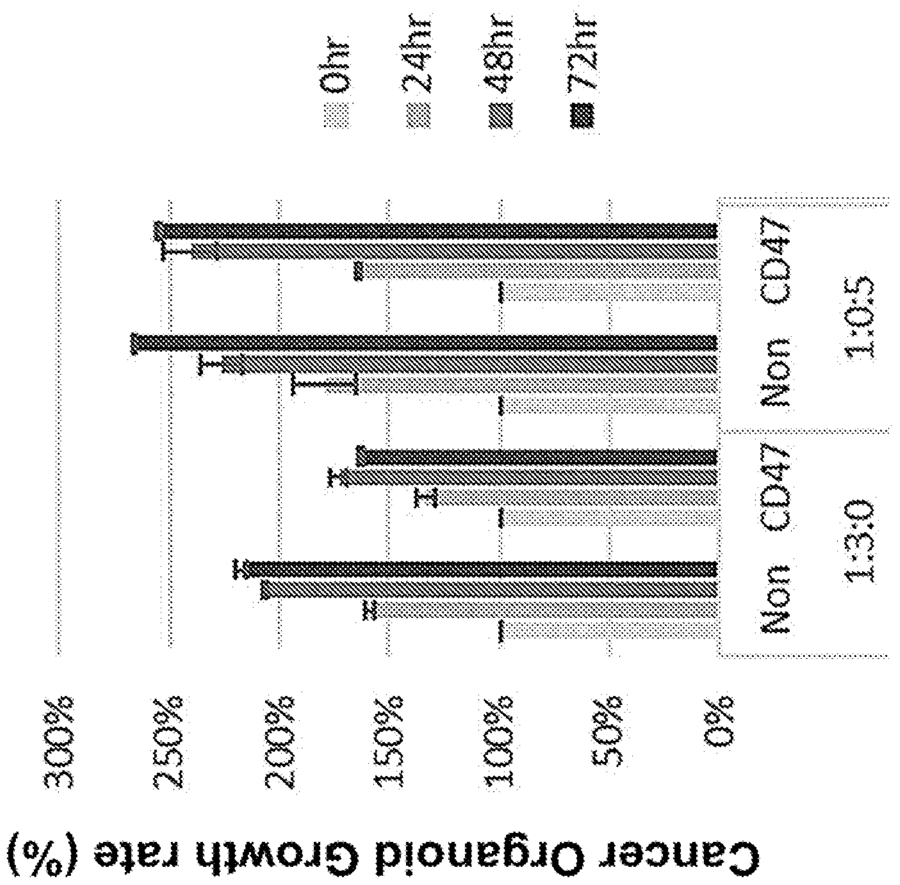
FIG. 8*a* is a graph showing the growth rate of cancer organoids according to the co-culture ratio of cancer organoids, M1 and M2 macrophages (classically activated macrophage, M2, hereinafter referred to as 'M2'), and it relates to the result of co-culture under the conditions without M1 ("1:3:0") or without M2 ("1:0:5"). 'Non' refers to a drug-untreated group, and 'CD47' refers to a drug-treated group treated with an anti-CD47 antibody as an exemplary drug.
Figure 8B:
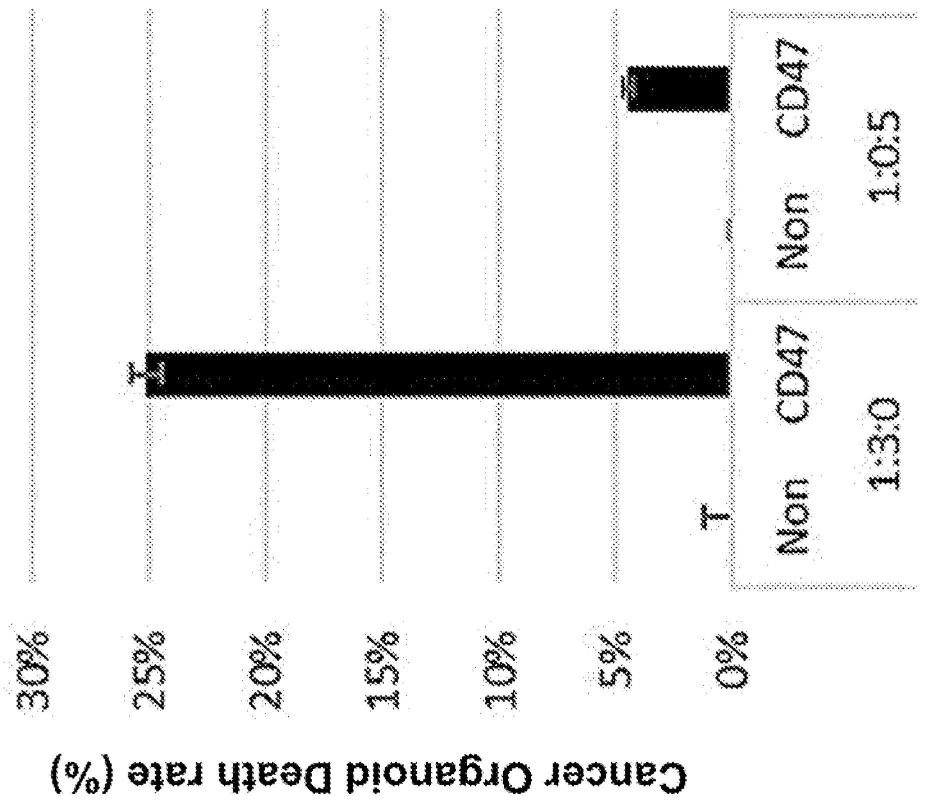
FIG. 8*b* is a graph showing the death rate of cancer organoids according to the co-culture ratio of cancer organoids, M1 and M2, and it relates to the result of co-culture under the conditions without M1 ("1:3:0") or without M2 ("1:0:5"). 'Non' refers to a drug-untreated group, and 'CD47' refers to a drug-treated group treated with an anti-CD47 antibody as an exemplary drug. The death rate was analyzed based on the results of measuring the growth rate after 72 hours (72 h) of drug treatment.

As a result, as shown in FIGS. 8*a* and 8*b*, the death rate of cancer organoids by an anti-CD47 antibody was as high as about 25% when only the cancer organoids and M1 were co-cultured at a mixing ratio of 1:3, except for M2 among the cancer organoids, M1 and M2. On the other hand, the death rate of cancer organoids by an anti-CD47 antibody was remarkably low as about 5% when only the cancer organoids and M2 were co-cultured at a mixing ratio of 1:5, except for M1 among the cancer organoids, M1 and M2.

Figure 9A:
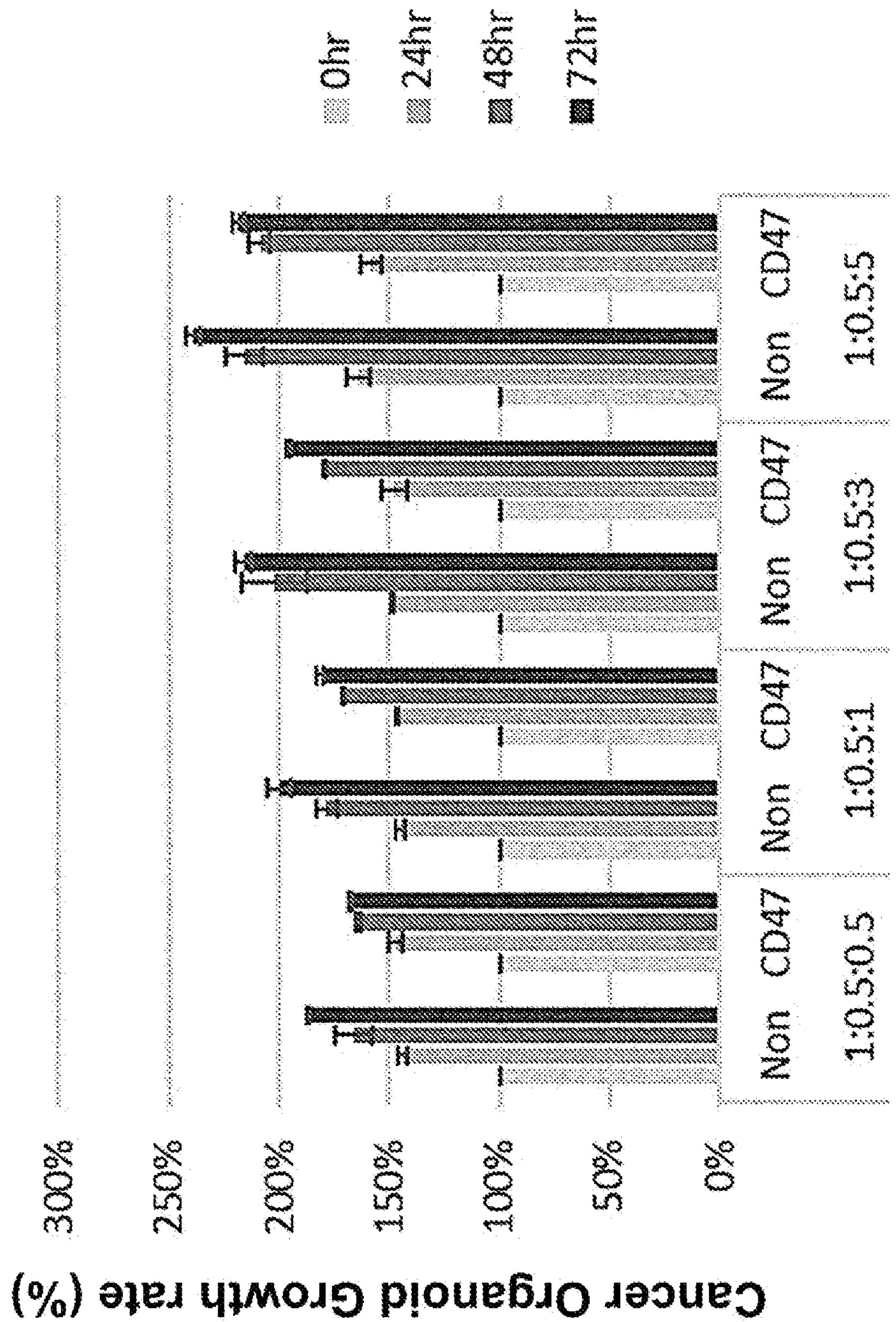
FIG. 9*a* is a graph showing the growth rate of cancer organoids according to the co-culture ratio of cancer organoids, M1 and M2, and it relates to the result of co-culture in the mixed condition in which cancer organoids and M1 were fixed in the cell number ratio of 1:0.5. 'Non' refers to a drug-untreated group, and 'CD47' refers to a drug-treated group treated with an anti-CD47 antibody as an exemplary drug.
Figure 9B:
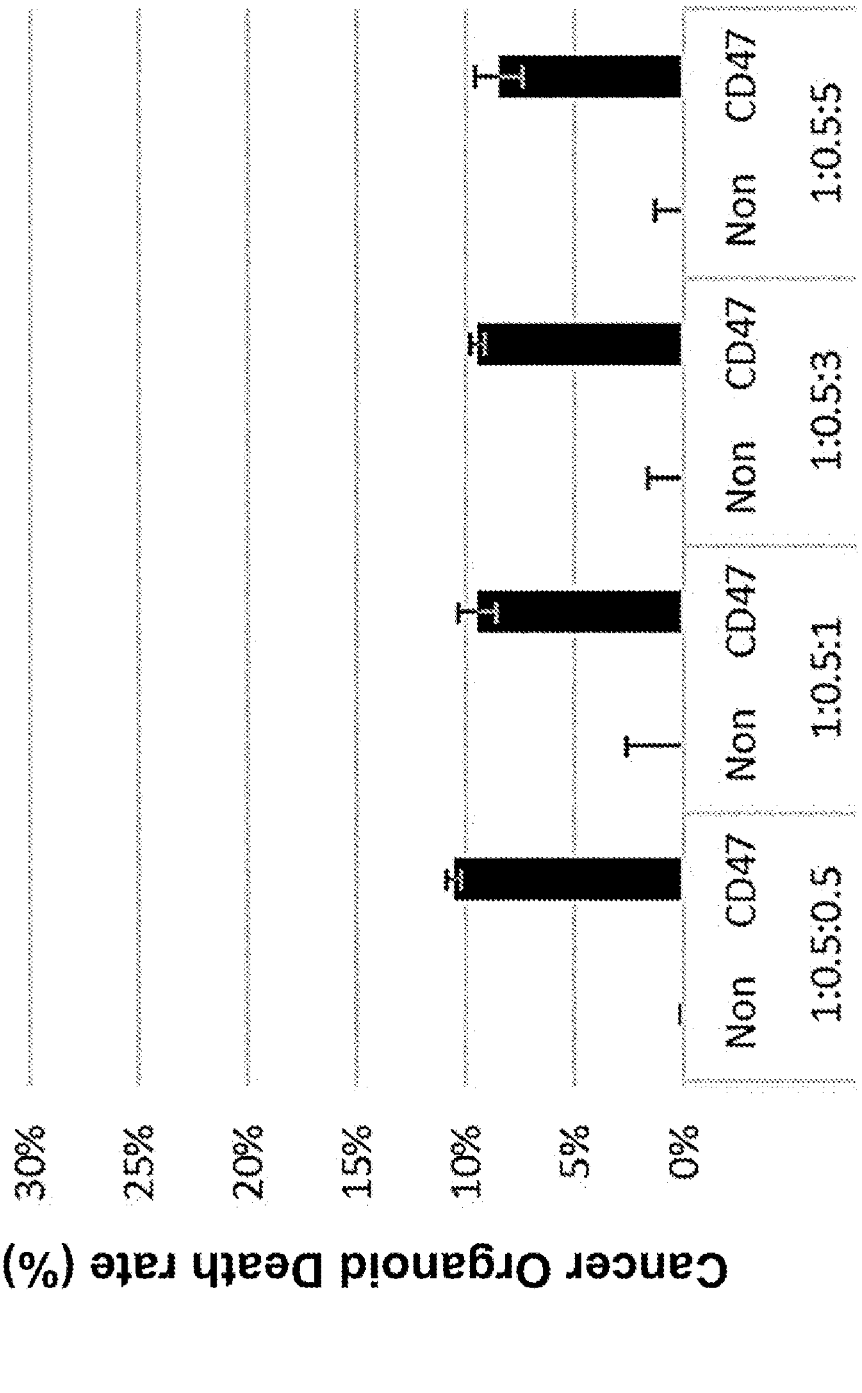
FIG. 9*b* is a graph showing the death rate of cancer organoids according to the co-culture ratio of cancer organoids, M1 and M2, and it relates to the result of co-culture in the mixed condition in which cancer organoids and M1 were fixed in the cell number ratio of 1:0.5. 'Non' refers to a drug-untreated group, and 'CD47' refers to a drug-treated group treated with an anti-CD47 antibody as an exemplary drug. The death rate was analyzed based on the results of measuring the growth rate after 72 hours (72 h) of drug treatment.

On the other hand, as shown in FIGS. 9*a* and 9*b*, the death rate of cancer organoids according to the increase in the ratio of M2 did not show a significant difference depending on the mixing ratios when cancer organoids and M1 were co-cultured at a ratio of 1:0.5. The death rate of cancer organoids was about 10% at maximum in all of the drug-treated groups treated with the anti-CD47 antibody, confirming that the efficacy of the drug was not high.

Figure 10A:
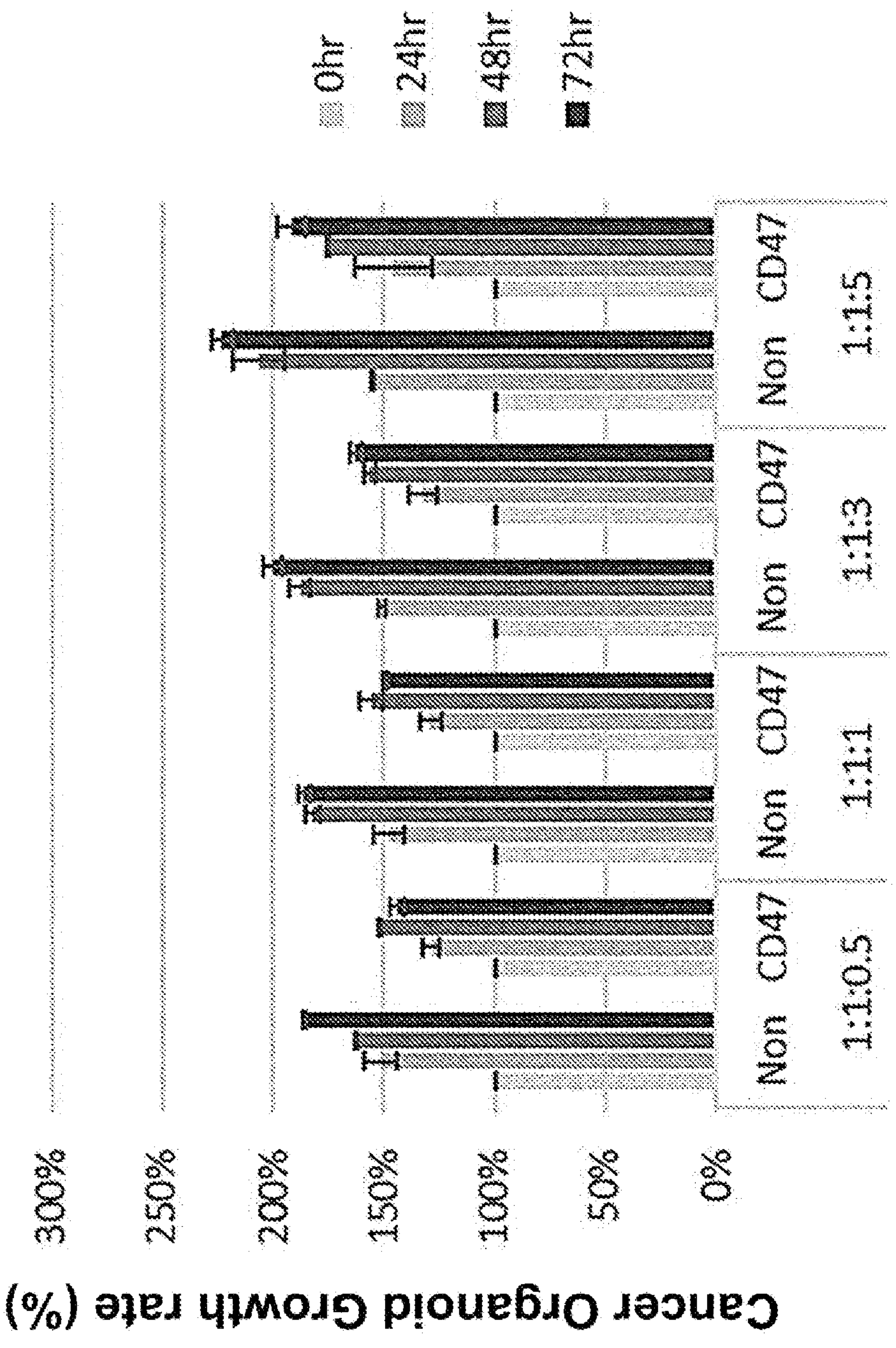
FIG. 10*a* is a graph showing the growth rate of cancer organoids according to the co-culture ratio of cancer organoids, M1 and M2, and it relates to the result of co-culture in the mixed condition in which cancer organoids and M1 were fixed in the cell number ratio of 1:1. 'Non' refers to a drug-untreated group, and 'CD47' refers to a drug-treated group treated with an anti-CD47 antibody as an exemplary drug.
Figure 10B:
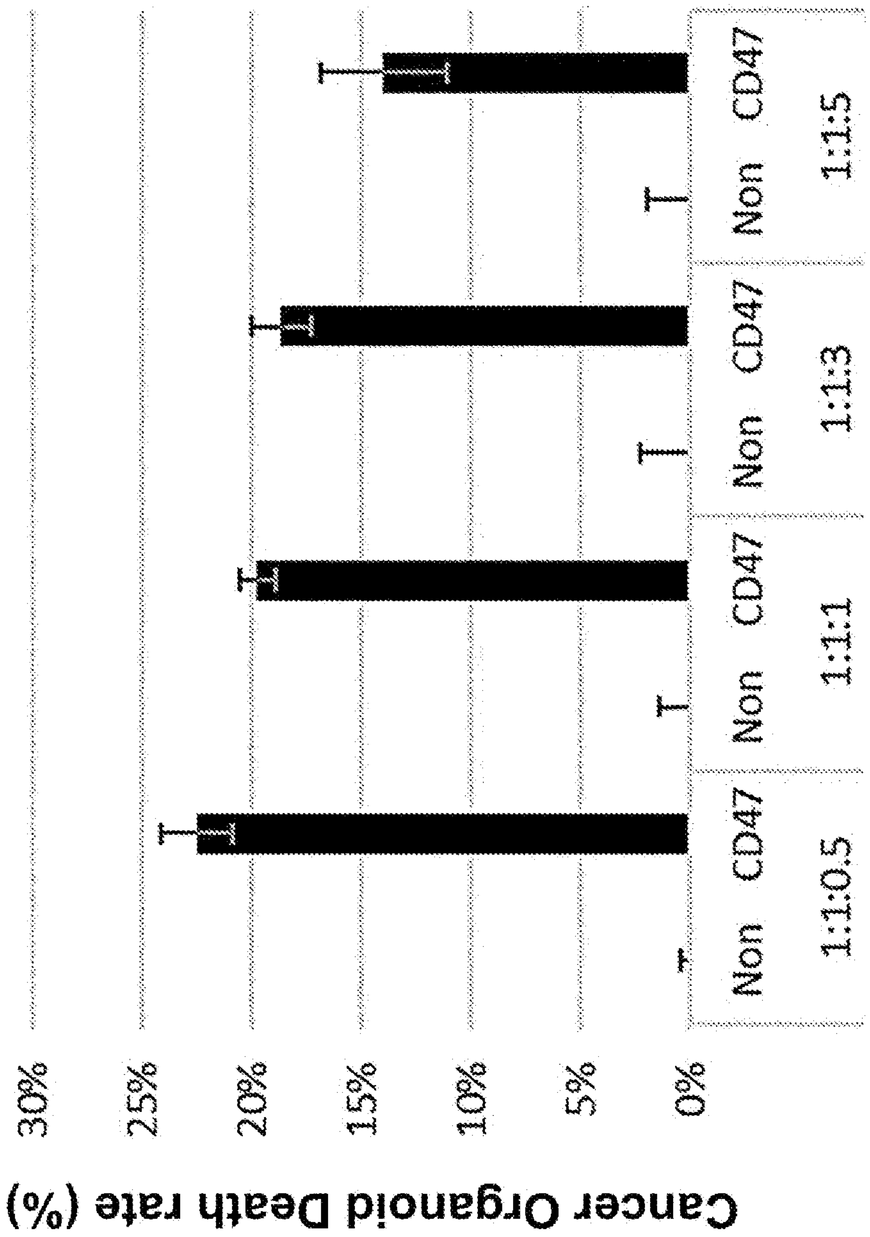
FIG. 10*b* is a graph showing the death rate of cancer organoids according to the co-culture ratio of cancer organoids, M1 and M2, and it relates to the result of co-culture in the mixed condition in which cancer organoids and M1 were fixed in the cell number ratio of 1:1. 'Non' refers to a drug-untreated group, and 'CD47' refers to a drug-treated group treated with an anti-CD47 antibody as an exemplary drug. The death rate was analyzed based on the results of measuring the growth rate after 72 hours (72 h) of drug treatment.

As shown in FIGS. 10*a* and 10*b*, when cancer organoids and M1 were co-cultured at a ratio of 1:1, it was confirmed that the death rate of cancer organoids by the drug increased to a high level up to about 23% at maximum in all groups mixing M2 at a ratio of 0.5 to 5.

Figure 11A:
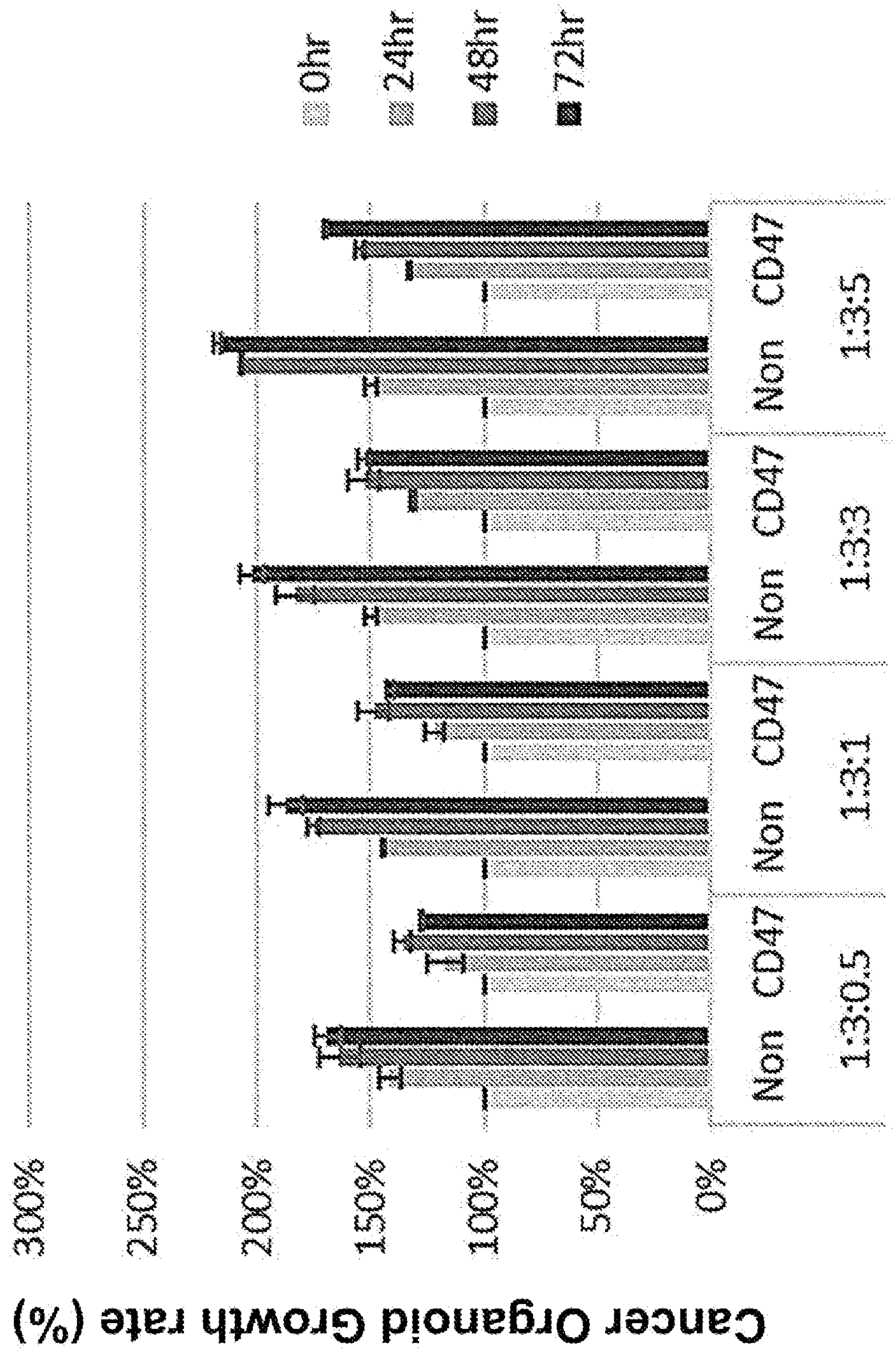
FIG. 11*a* is a graph showing the growth rate of cancer organoids according to the co-culture ratio of cancer organoids, M1 and M2, and it relates to the result of co-culture in the mixed condition in which cancer organoids and M1 were fixed in the cell number ratio of 1:3."). 'Non' refers to a drug-untreated group, and 'CD47' refers to a drug-treated group treated with an anti-CD47 antibody as an exemplary drug.
Figure 11B:
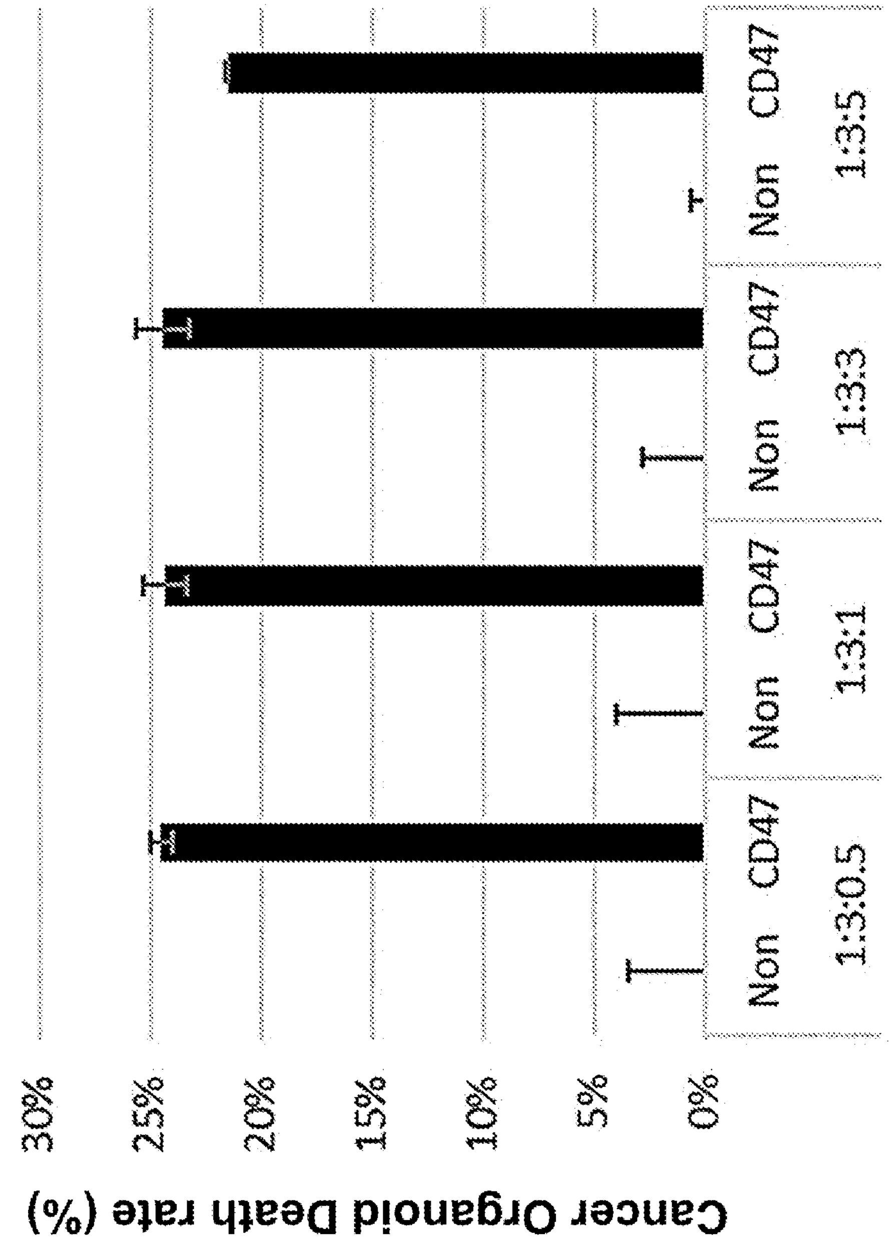
FIG. 11*b* is a graph showing the death rate of cancer organoids according to the co-culture ratio of cancer organoids, M1 and M2, and it relates to the result of co-culture in the mixed condition in which cancer organoids and M1 were fixed in the cell number ratio of 1:3. 'Non' refers to a drug-untreated group, and 'CD47' refers to a drug-treated group treated with an anti-CD47 antibody as an exemplary drug. The death rate was analyzed based on the results of measuring the growth rate after 72 hours (72 h) of drug treatment.

In addition, as shown in FIGS. 11*a* and 11*b*, when cancer organoids and M1 were co-cultured at a ratio of 1:3, it was confirmed that the death rate of cancer organoids by the drug increased to a high level up to about 25% at maximum in all groups mixing M2 at a ratio of 0.5 to 5.

The above results show that the most optimal co-culture ratio of cancer organoids, M1 and M2 for an anticancer drug efficacy evaluation or screening system is 1:1 to 3:0.5 to 5, and suggests that this system is suitable for evaluating or screening the efficacy of anticancer drugs in which macrophages are involved in drug action.

Example 3. Anticancer Drug Efficacy Evaluation and Screening System Comprising Cancer Organoids and TILs The inventors have established an in vitro efficacy evaluation and screening system that can accurately predict the efficacy of a drug when administered to a subject, by similarly reproducing the environment in which cancer exists in the body.

Specifically, a co-culture system in which cancer organoids and Tumor-infiltrating lymphocytes (hereinafter referred to as 'TIL') coexist was used.

Example 3.1. Obtaining TILs

TILs are cells that infiltrate or surround tumor tissue, and play a role in recognizing and killing cancer cells. TILs includes various types of immune cells, and most of them is CD8+ T cells capable of attacking tumors. In addition, since TILs are isolated from tumor tissue, the CD8+ T cells included therein are already activated and are in a state capable of recognizing and attacking cancer cells.

That is, in the anticancer drug efficacy evaluation and screening system according to the present invention, the activation process of CD8+ T cells was omitted by using TIL isolated from tissues. In addition, a condition in which activated CD8+ T cells are maintained longer was drawn, and was applied to this system.

Specifically, TILs were obtained by cutting the tumor tissue into small pieces, collecting the separated immune cells and tissues, and culturing them in a CD8+ T cell culture medium to grow only immune cells. Thereafter, TIL was cultured alone or co-cultured by mixing TIL and cancer organoid in a cell number ratio of 20:1 (TIL:cancer organoid=$1\times10^5$:$5.0\times10^3$), and TILs were analyzed by FACS. Herein, CD56 was used as markers to analyze total immune cells present in TILs, and CD8 was used as markers to analyze CD8+ T cells among total immune cells present in TILs. If the ratio of CD8+ is 20% or more in this FACS analysis result, such immune cells are considered to be usable for drug efficacy evaluation. Table 4 below shows the ratio of CD8+ T cells present in total TILs.

TABLE 4

| Condition | Group 1 (Single culture) | Group 2 (Co-culture) |
|---|---|---|
| Culture Day 1 | 50.7% | 50.7% |
| Culture Day 7 | 90.3% | 91.4% |
| Culture Day 14 | 29.9% | 97.1% |
| Culture Day 21 | 21.1% | 37.9% |

Figure 12:
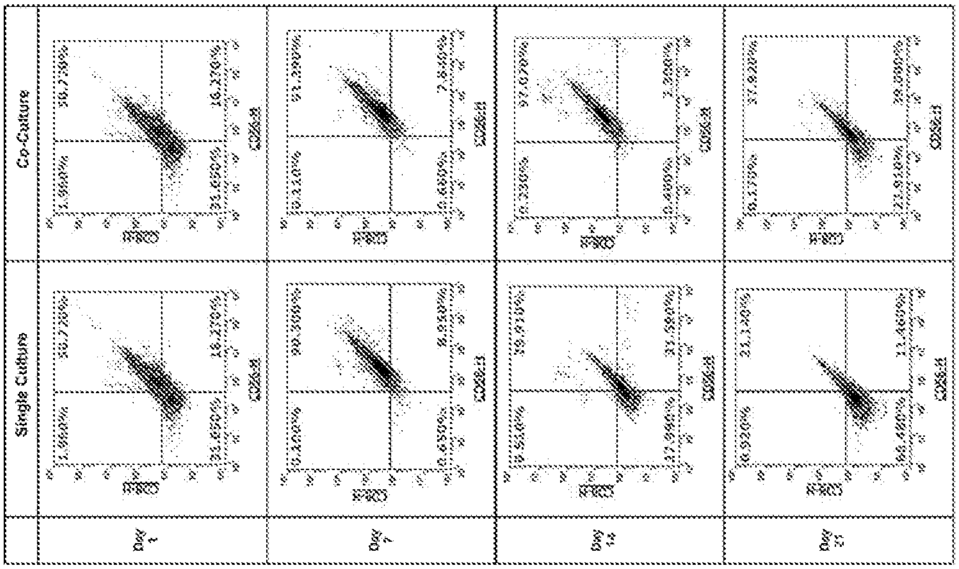
FIG. 12 is the results of FACS analysis on TILs prepared through monoculture of Tumor-infiltrating lymphocyte (hereinafter referred to as 'TIL'); or co-culture of TILs and cancer organoids, and shows the ratio of TILs expressing CD8 protein on the cell surface to total TILs.

As a result, as shown in FIG. 12 and Table 4, there was no significant difference in the results of single culture and co-culture from Culture Day 1 to Culture Day 7. However, a significant difference was shown from Culture Day 14. In the single culture, the ratio of CD8+ T cells was about 23.9%, which was remarkably reduced compared to Culture Day 7 (about 90.3%), whereas in the co-culture, the ratio of CD8+ T cell was about 97.1% of the total cell, and rather increased compared to Culture Day 7 (about 91.4%).

Even in the co-culture after Culture Day 21, the ratio of CD8+ T cells was about 37.9%, which reduced compared to Culture Day 14 (about 97.1%).

The above results show that since TILs obtained through co-culture with cancer organoids maintain activated CD8+ T cells for a long period of time, it is possible to establish an anticancer drug efficacy evaluation and screening system with higher quality and reproducibility and improved accuracy when using it.

Example 3.2. Co-Culture Ratio of Cancer Organoids and TILs

In order to establish a drug efficacy evaluation and screening system utilizing a co-culture system of cancer organoids and TILs, an mixing ratio of cancer organoids and TILs was drawn.

Specifically, the inventors set a mixing ratio satisfying co-culture conditions under which (1) cancer organoids grow properly and (2) drug efficacy is well observed. Cancer organoids were prepared using cancer cells isolated from tumor tissues of lung cancer or colorectal cancer patients, and TILs obtained by co-culture with cancer organoids for 14 days according to Example 1.1 were used.

As shown in Table 5 below, the ratio for cancer organoids was fixed to 1, and the ratio for TILs was set to 0.5 to 3. Herein, the number of organoids or TILs was set to 1 for $5.0\times10^3$.

TABLE 5

| Group | Cancer Organoid | TIL |
|---|---|---|
| 1 | 1 | 0.5 |
| 2 | 1 | 1.5 |
| 3 | 1 | 3 |

In addition, for the co-cultures of cancer organoids and TILs according to the ratio above, those not treated with the drug were set as the control group (hereinafter referred to as 'drug-untreated group'), and those treated with atezolizumab, which is currently marketed and used for a cancer treatment, as an exemplary drug were set as the experimental group (hereinafter referred to as 'drug-treated group'). After co-culturing for 72 hours, the growth rate was measured immediately after the start of the co-culture (0 h), after 24 hours (24 h), after 48 hours (48 h) and after 72 hours (72 h), respectively, and the death rate was analyzed by the following method through the measured growth rate: Cancer organoid death rate (%)=[1−(growth rate of cancer organoids in the drug-treated group*)/(growth rate of cancer organoids in the drug-untreated group**)]×100

Growth rate of cancer organoids in the drug−treated group (%) = (cancer organoid area after 24, 48 or 72 hours of drug treatment)/(cancer organoid area immediately after the start of the co−culture (0 h) × 100

Growth rate of cancer organoids in the drug−untreated group (%) = (cancer organoid area after 24, 48 or 72 hours without drug treatment)/(cancer organoid area immediately after the start of the co−culture (0 h) × 100

Figure 13A:
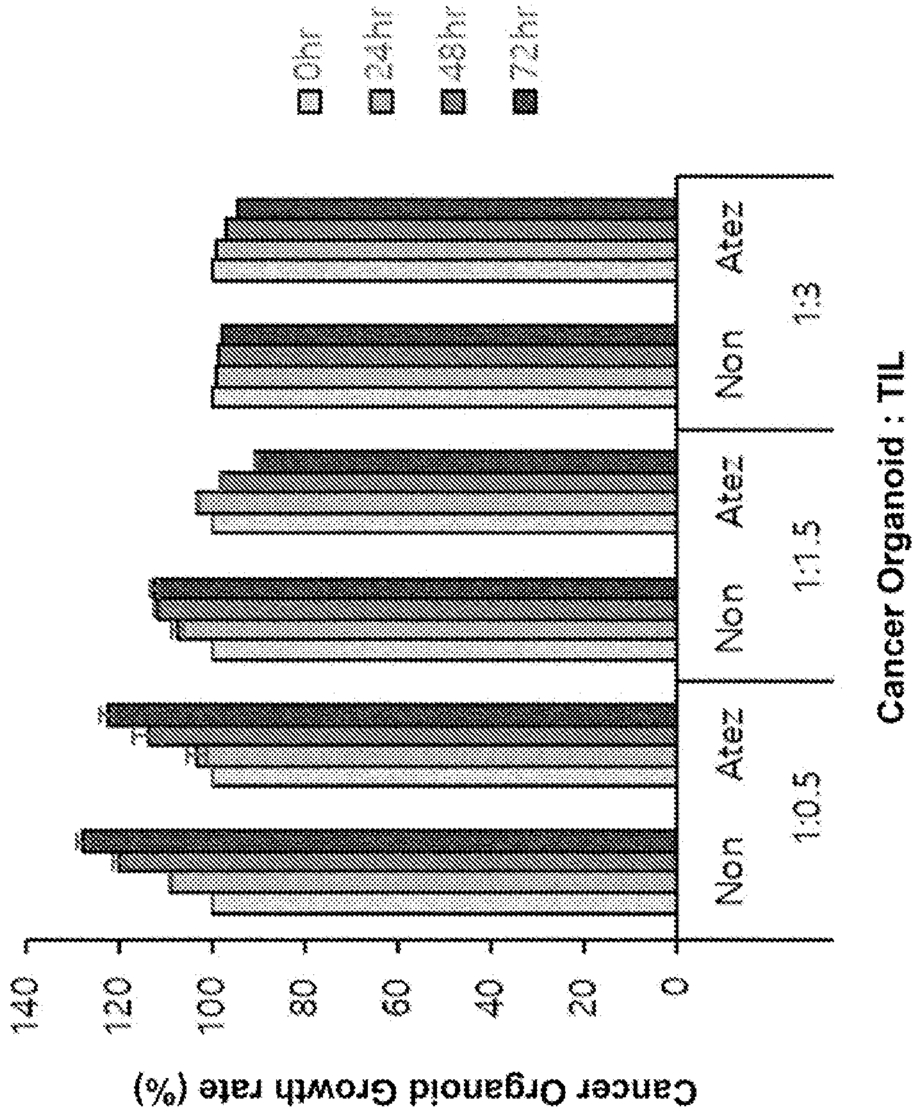
FIG. 13*a* is a graph showing the growth rate of lung cancer organoids according to the co-culture ratio of lung cancer organoids and TILs. 'Non' refers to a drug-untreated group, and 'Atez' refers to a drug-treated group treated with an atezolizumab as an exemplary drug. Growth rates were measured immediately after drug treatment (0 h), after 24 hours (24 h), after 48 hours (48 h), and after 72 hours (72 h), respectively.
Figure 13B:
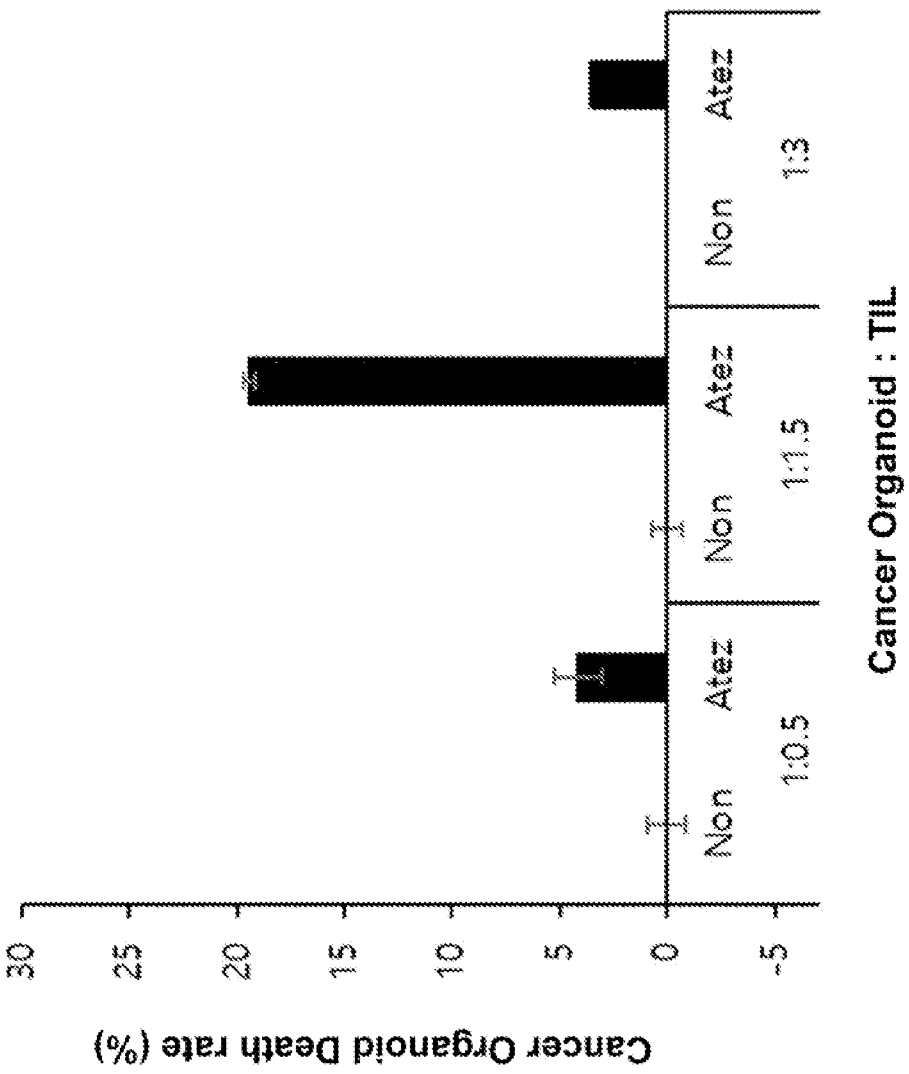
FIG. 13*b* is a graph showing the death rate of lung cancer organoids according to the co-culture ratio of lung cancer organoids and TILs. 'Non' refers to a drug-untreated group, and 'Atez' refers to a drug-treated group treated with an atezolizumab as an exemplary drug. The death rate was analyzed based on the results of measuring the growth rate immediately after drug treatment (0 h), 24 hours later (24 h), 48 hours later (48 h), and 72 hours later (72 h).

As a result, as shown in FIGS. 13*a* and 13*b*, when lung cancer organoids and TILs were co-cultured at a ratio of 1:0.5, the lung cancer organoids did not respond to the drug, and accordingly the growth rate and death rate of lung cancer organoids were similar in the control group and the experimental group. In particular, it was confirmed that the death rate of lung cancer organoids in the drug-treated group was just about 5%, making it impossible to accurately determine the efficacy of the drug.

In addition, when lung cancer organoids and TILs were co-cultured at a ratio of 1:3, it was confirmed that the death rate of lung cancer organoids in the drug-treated group was just about 5%, making it impossible to accurately determine the efficacy of the drug.

On the other hand, when lung cancer organoids and TILs were co-cultured at a ratio of 1:1.5, anticancer effects of atezolizumab were shown by inhibiting the growth and increasing death of lung cancer organoids. In particular, the death rate of lung cancer organoids in the drug-treated group was about 20%, and it was confirmed that atezolizumab exhibited a high level of lung cancer organoid death rate compared to other mixture ratios.

Figure 14A:
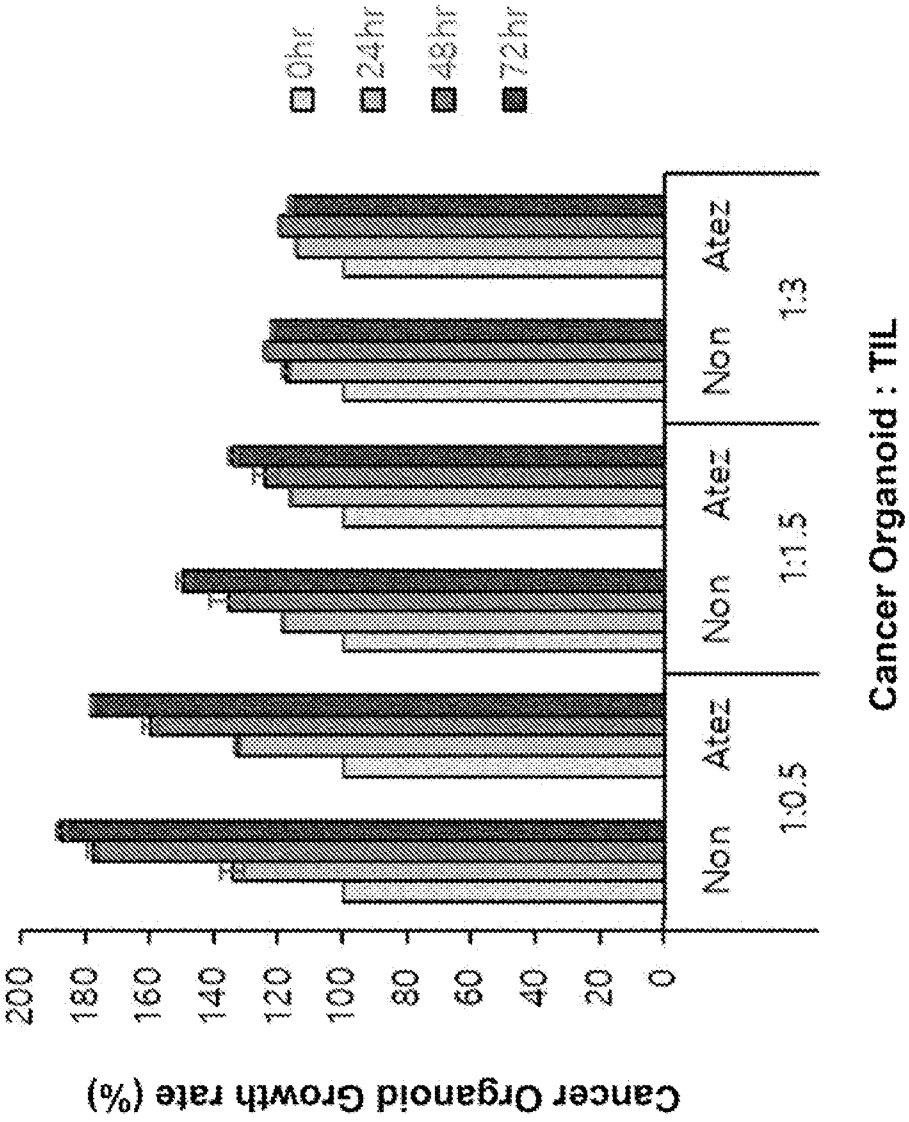
FIG. 14*a* is a graph showing the growth rate of colorectal cancer organoids according to the co-culture ratio of colorectal cancer organoids and TILs. 'Non' refers to a drug-untreated group, and 'Atez' refers to a drug-treated group treated with an atezolizumab as an exemplary drug. Growth rates were measured immediately after drug treatment (0 h), after 24 hours (24 h), after 48 hours (48 h), and after 72 hours (72 h), respectively.
Figure 14B:
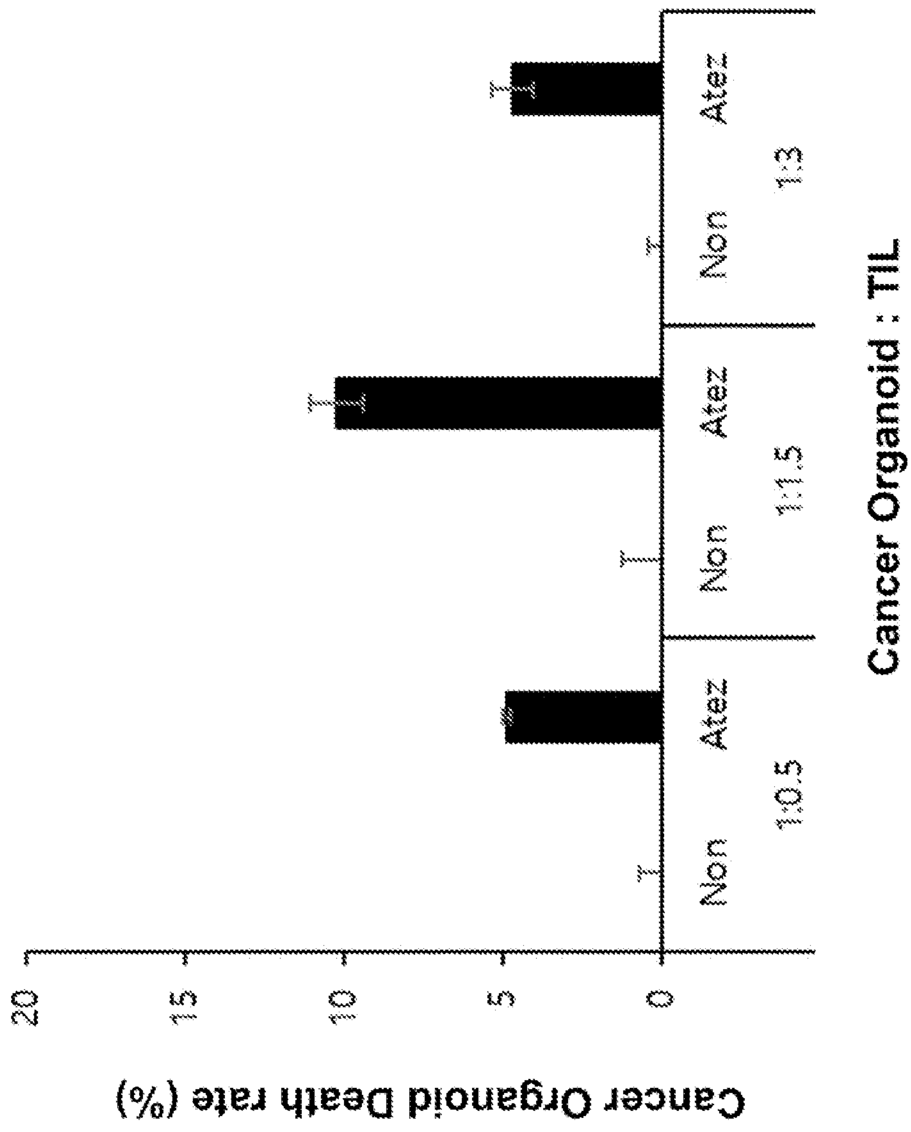
FIG. 14*b* is a graph showing the death rate of colorectal cancer organoids according to the co-culture ratio of colorectal cancer organoids and TILs. 'Non' refers to a drug-untreated group, and 'Atez' refers to a drug-treated group treated with an atezolizumab as an exemplary drug. The death rate was analyzed based on the results of measuring the growth rate immediately after drug treatment (0 h), 24 hours later (24 h), 48 hours later (48 h), and 72 hours later (72 h).

In addition, as shown in FIGS. 14*a* and 14*b*, when colorectal cancer organoids and TILs were co-cultured at a ratio of 1:0.5, the colorectal cancer organoids did not respond to the drug, and accordingly the growth rate and death rate of colorectal cancer organoids were similar in the control group and the experimental group. In particular, it was confirmed that the death rate of colorectal cancer organoids in the drug-treated group was just about 5%, making it impossible to accurately determine the efficacy of the drug.

In addition, when colorectal cancer organoids and TILs were co-cultured at a ratio of 1:3, it was confirmed that the death rate of colorectal cancer organoids in the drug-treated group was just about 5%, making it impossible to accurately determine the efficacy of the drug.

On the other hand, when colorectal cancer organoids and TILs were co-cultured at a ratio of 1:1.5, anticancer effects of atezolizumab were shown by inhibiting the growth and increasing death of colorectal cancer organoids. In particular, the death rate of colorectal cancer organoids in the drug-treated group was about 10%, and it was confirmed that atezolizumab exhibited a high level of colorectal cancer organoid death rate compared to other mixture ratios.

The above results suggest that setting the co-culture ratio of cancer organoids and TILs to 1:1.5 is the most optimal ratio for an anticancer drug efficacy evaluation or screening system.

Example 4. Anticancer Drug Efficacy Evaluation and Screening System Comprising Cancer Organoids, Cytotoxic T Cells and Regulatory T Cells The inventors have established an in vitro efficacy evaluation and screening system that can accurately predict the efficacy of a drug when administered to a subject, by similarly reproducing the environment in which cancer exists in the body.

Specifically, in order to establish a co-culture system in which cancer organoids, cytotoxic T cells (hereinafter referred to as 'CD8+ T cells') and regulatory T cells (hereinafter referred to as 'Treg') coexist, the inventors set a mixing ratio satisfying co-culture conditions under which (1) cancer organoids grow properly and (2) drug efficacy is well observed.

As shown in Table 6 below, the ratio for cancer organoids was fixed to 1, and the ratio for CD8+ T cells and Treg was set to 0 to 3. Herein, the number of organoids or cells was set to 1 for $5.0\times10^3$.

TABLE 6

| Group | Cancer Organoid | CD8+ T cell | Treg |
|---|---|---|---|
| 1 | 1 | 3 | 0 |
| 2 | | 0 | 3 |
| 3 | | 1 | 0.5 |
| 4 | | | 1 |
| 5 | | | 3 |
| 6 | | 3 | 0.5 |
| 7 | | | 1 |
| 8 | | | 3 |

Cancer organoids were prepared using stem cells isolated from tumor tissue of colorectal cancer or lung cancer patients. The isolated stem cells were mixed with ECM (extracellular matrix) to grow into a 3D structure to make a dome, and then organoids were formed and used through culture. CD8+ T cells and Tregs were obtained from blood obtained from colorectal cancer or lung cancer patients. Immune cells present in the blood were differentiated, and CD8+ and Treg cells were isolated from the differentiated immune cells using a MACS (magnetic activated cell sorting) method.

Example 4.1. Conditions for Proper Growth of Cancer Organoids

A mixing ratio of cancer organoids, CD8+ T cells and Tregs, which allows cancer organoids to grow properly even when co-cultured with immune cells (CD8+ T cells and Tregs), was drawn.

Specifically, after co-culturing at the mixing ratio according to Table 6 above, the area of cancer organoids was measured immediately after the start of the co-culture (0 h), after 24 hours (24 h), after 48 hours (48 h) and after 72 hours (72 h), respectively, and the growth rate was analyzed by the following formula.

$$^{*}\text{Growth rate of cancer organoids (\%)} = \left(\text{cancer organoid area after co-culture for 24, 48, or 72 hours}\right)/\left(\text{cancer organoid area immediately after the start of the co-culture}\right)\times 100$$

Figure 15:
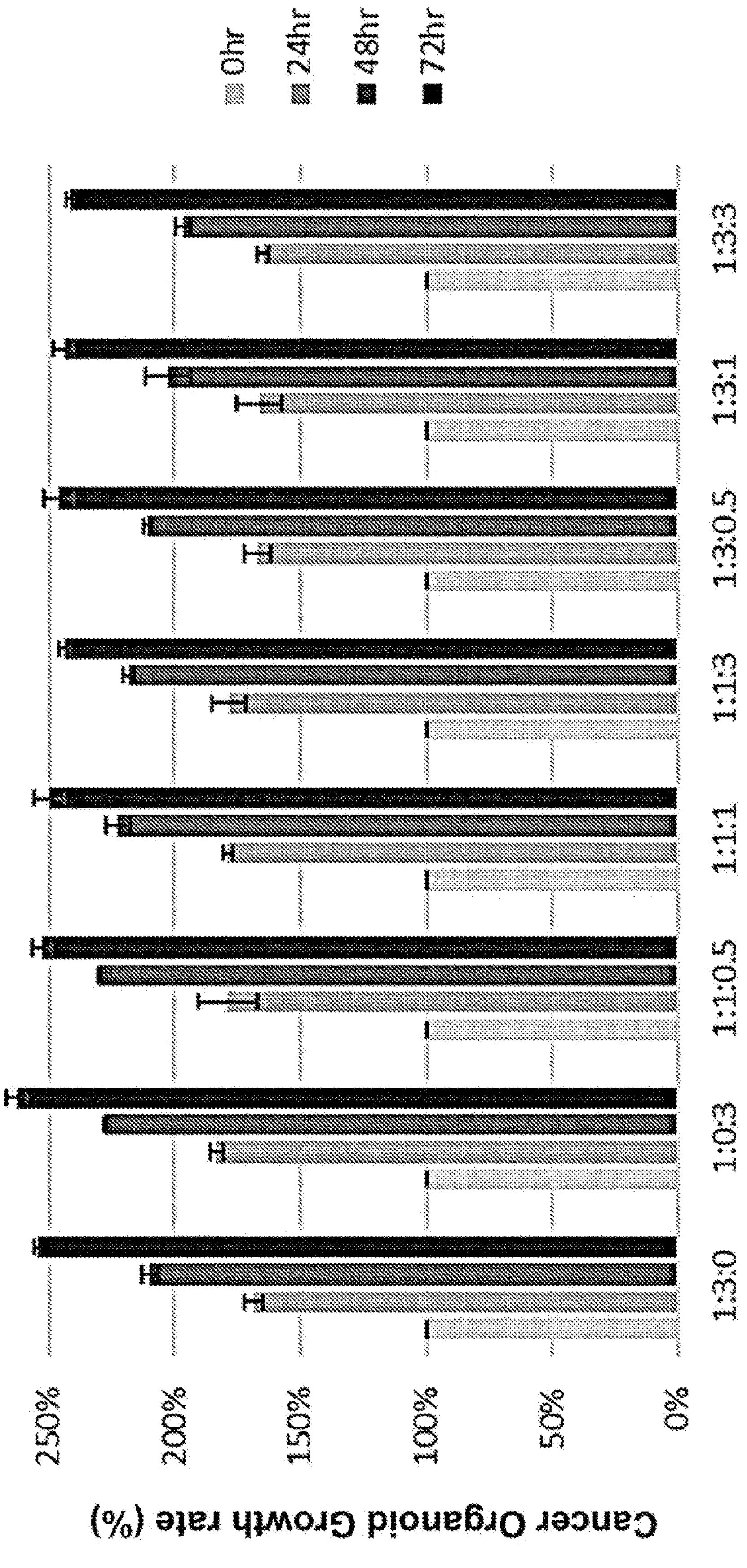
FIG. 15 is a graph showing the growth rate of colorectal cancer organoids according to each co-culture ratio of colorectal cancer organoids, CD8+ T cells and regulatory T cells (hereinafter referred to as 'Treg'). As a representative example, "1:3:0" described in the figure means that colorectal cancer organoids, CD8+ T cells and Tregs are mixed in a cell number ratio of 1:3:0. The growth rate was analyzed immediately after the start of the co-culture (0 h), after 24 hours (24 h), after 48 hours (48 h), and after 72 hours (72 h), respectively.
Figure 16:
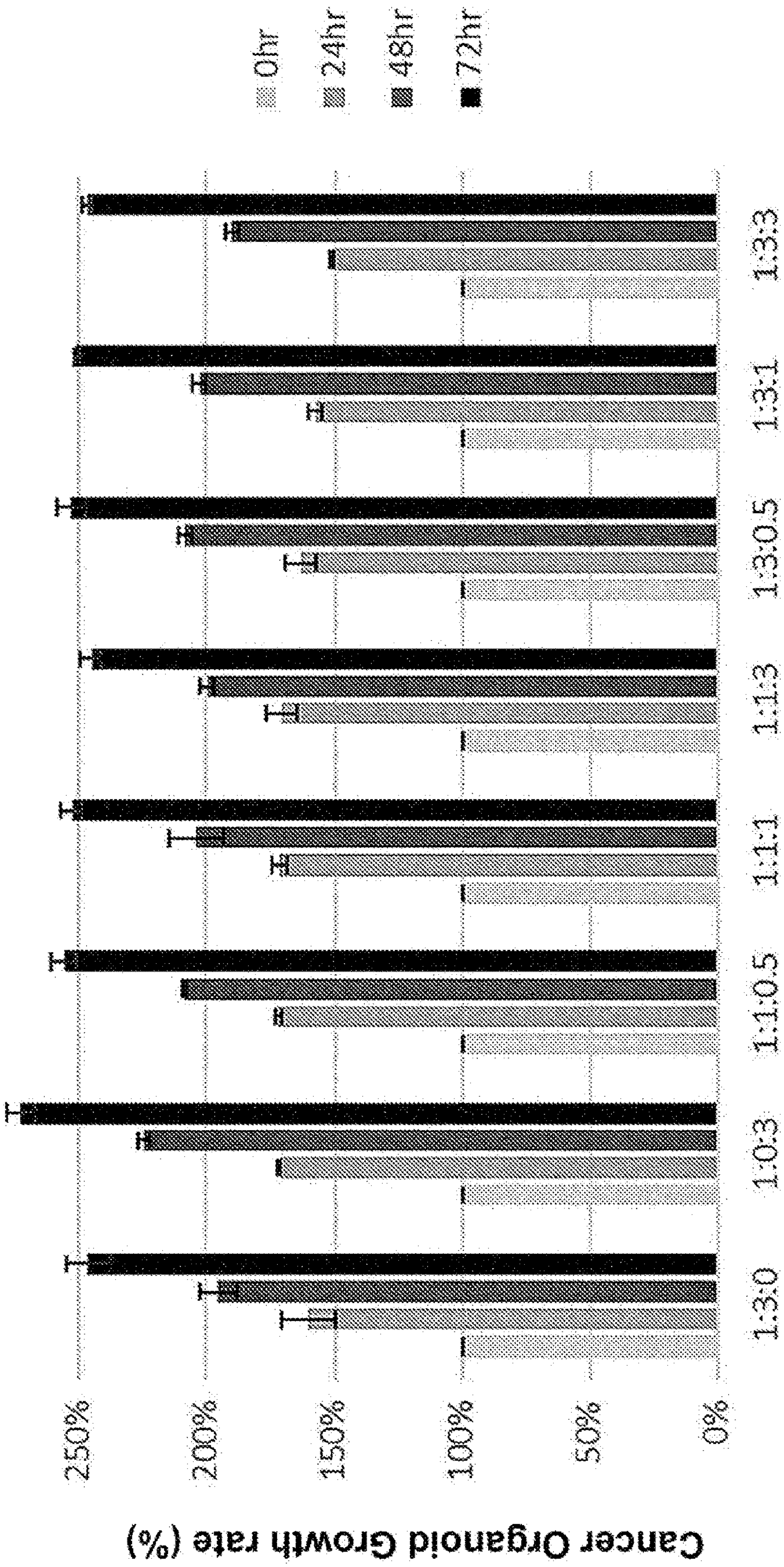
FIG. 16 is a graph showing the growth rate of lung cancer organoids according to each co-culture ratio of lung cancer organoids, CD8+ T cells and Tregs. As a representative example, "1:3:0" described in the figure means that lung cancer organoids, CD8+ T cells and Tregs are mixed in a cell number ratio of 1:3:0. The growth rate was analyzed immediately after the start of the co-culture (0 h), after 24 hours (24 h), after 48 hours (48 h), and after 72 hours (72 h), respectively.

As a result, as shown in FIGS. 15 and 16, the growth of colorectal cancer or lung cancer organoids was not inhibited and grew appropriately in all mixing ratios, and no significant difference was found between each mixing ratio.

Example 4.2. Conditions in which Drug Efficacy is High

A mixture ratio of cancer organoids, CD8+ T cells and Tregs, which allows the efficacy of anticancer drugs targeting CD8+ T cells and anticancer drugs targeting Tregs to be high, was drawn.

Specifically, for the co-cultures of cancer organoids, CD8+ T cells and Tregs according to the mixing ratio in Table 6 above, those not treated with the drug were set as the control group (hereinafter referred to as 'drug-untreated group'), and those treated with an atezolizumab targeting CD8+ T cells or an anti-TIGIT antibody targeting CD8+ T cells or Tregs as an exemplary drug were set as the experimental group (hereinafter referred to as 'drug-treated group'). After co-culturing them for 72 hours, the growth rate was measured after 72 hours of drug treatment (72 h), and the death rate was analyzed by the following method through the measured growth rate.

$$\text{Cancer organoid death rate (\%)} = [1 - (\text{growth rate of cancer organoids in the drug-treated group}^{*})/(\text{growth rate of cancer organoids in the drug-untreated group}^{**})]\times 100$$

$$\text{Growth rate of cancer organoids in the drug-treated group (\%)} = (\text{cancer organoid area after 72 hours of drug treatment})/(\text{cancer organoid area immediately after the start of the co-culture (0 h)}\times 100$$

$$\text{Growth rate of cancer organoids in the drug-untreated group (\%)} = (\text{cancer organoid area after 72 hours without drug treatment})/(\text{cancer organoid area immediately after the start of the co-culture (0 h)}\times 100$$

Figure 17:
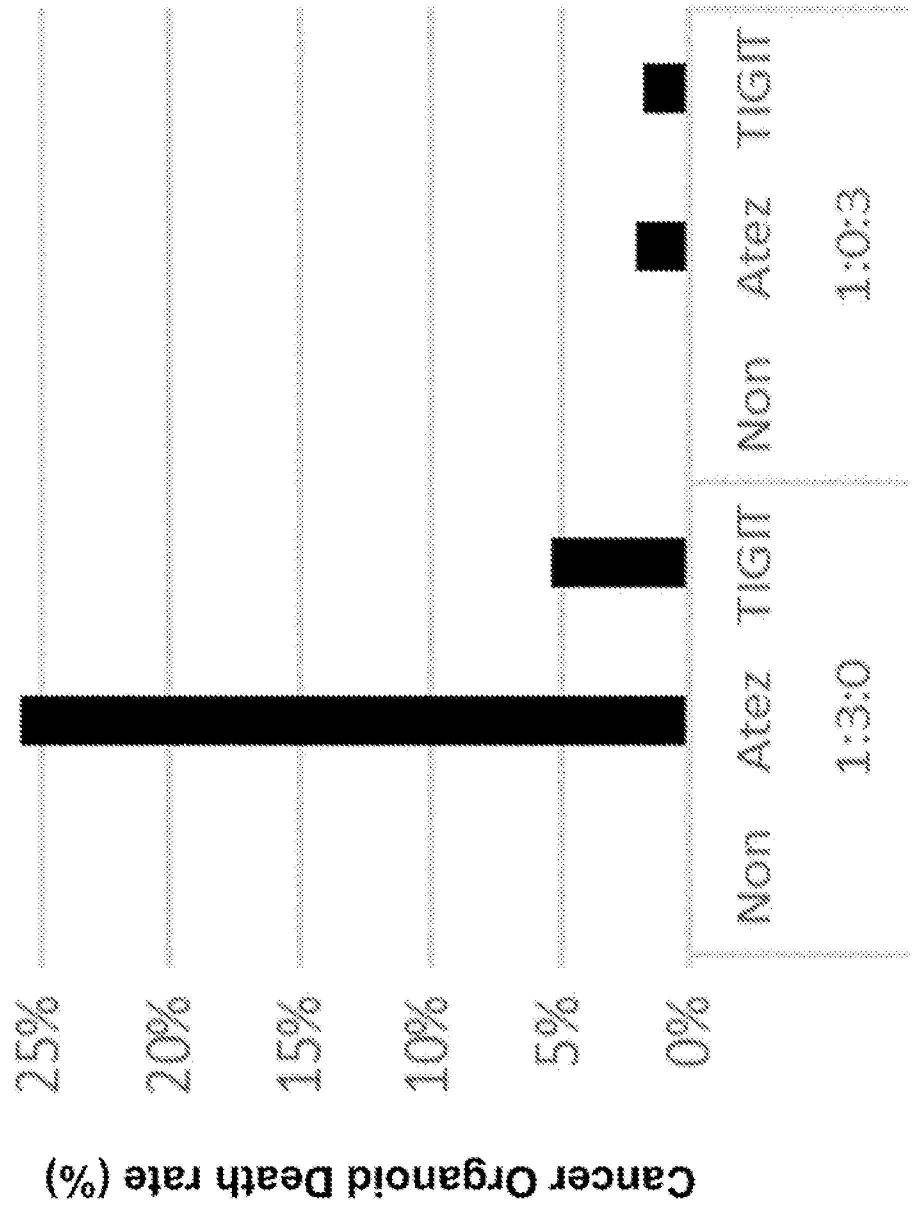
FIG. 17 is a graph showing the growth rate of colorectal cancer organoids according to each co-culture ratio of colorectal cancer organoids, CD8+ T cells and Tregs, and it relates to the result of co-culture under the conditions without Treg ("1:3:0") or without CD8+ T cell ("1:0:3"). 'Non' refers to a drug-untreated group, 'Atez' refers to a drug-treated group treated with an atezolizumab as an exemplary drug, and 'TIGIT' refers to a drug-treated group treated with an anti-TIGIT antibody as an example. The death rate was analyzed based on the results of measuring the growth rate after 72 hours (72 h) of drug treatment.

As a result, as shown in FIG. 17, when only the colorectal cancer organoids and CD8+ T cells were co-cultured at a mixing ratio of 1:3, except for Tregs among the cancer organoids, CD8+ T cells and Tregs, the death rate of cancer organoids by atezolizumab is as high as about 26%, but the death rate of cancer organoids by anti-TIGIT antibody is just about 5%, making it impossible to accurately determine the efficacy of the drug. In addition, when only the colorectal cancer organoids and Tregs were co-cultured at a mixing ratio of 1:3 except for CD8+ T cells among the cancer organoids, CD8+ T cells and Tregs, the death rate of cancer organoids by atezolizumab and anti-TIGIT antibody was remarkably low as about 2%, confirming that the efficacy of the drug could not be accurately determined.

Figure 18:
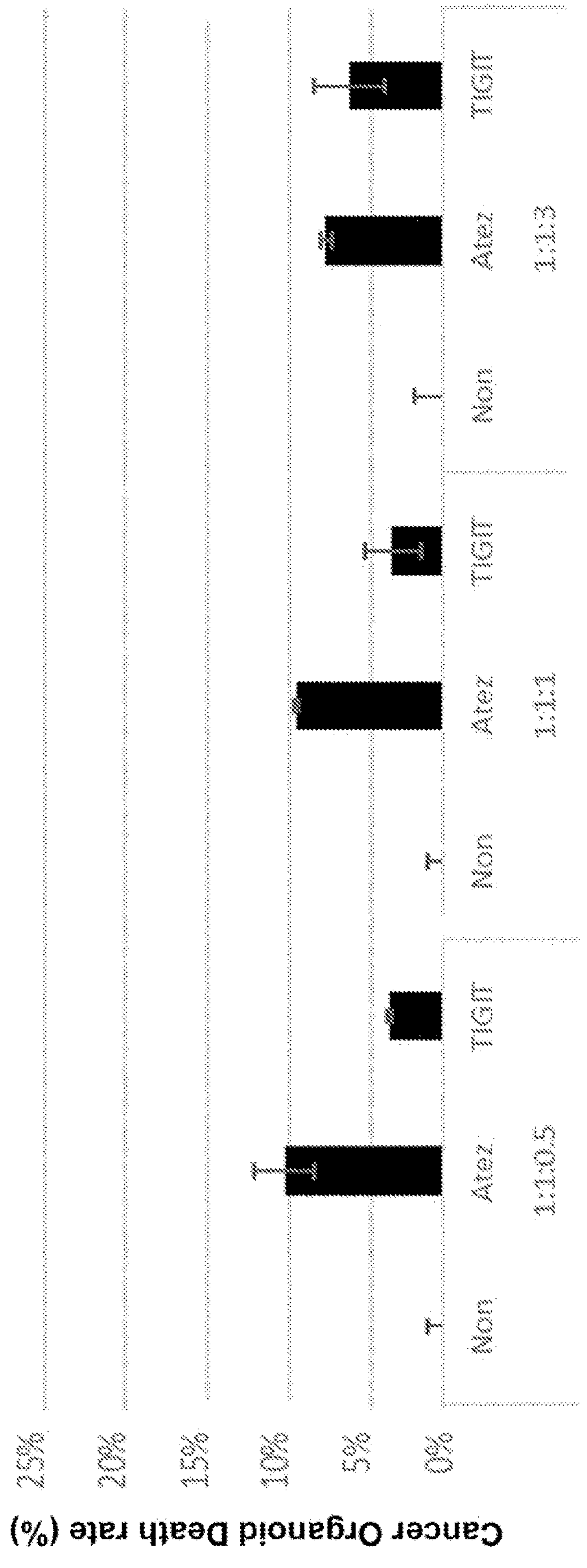
FIG. 18 is a graph showing the death rate of colorectal cancer organoids according to each co-culture ratio of colorectal cancer organoids, CD8+ T cells and Tregs, and it relates to the result of co-culture in the mixed condition in which colorectal cancer organoids and CD8+ T cells were fixed in the cell number ratio of 1:1. 'Non' refers to a drug-untreated group, 'Atez' refers to a drug-treated group treated with an atezolizumab as an exemplary drug, and 'TIGIT' refers to a drug-treated group treated with an anti-TIGIT antibody as an exemplary drug. The death rate was analyzed based on the results of measuring the growth rate after 72 hours (72 h) of drug treatment.

In addition, as shown in FIG. 18, when colorectal cancer organoids and CD8+ T cells were co-cultured at a mixing ratio of 1:1, the death rate of cancer organoids by the anti-TIGIT antibody increased as the Treg ratio increased, but the maximum level was just about 6%, and the death rate of cancer organoids by atezolizumab was just about 10% at maximum, confirming that the efficacy of the drug could not be accurately determined.

Figure 19:
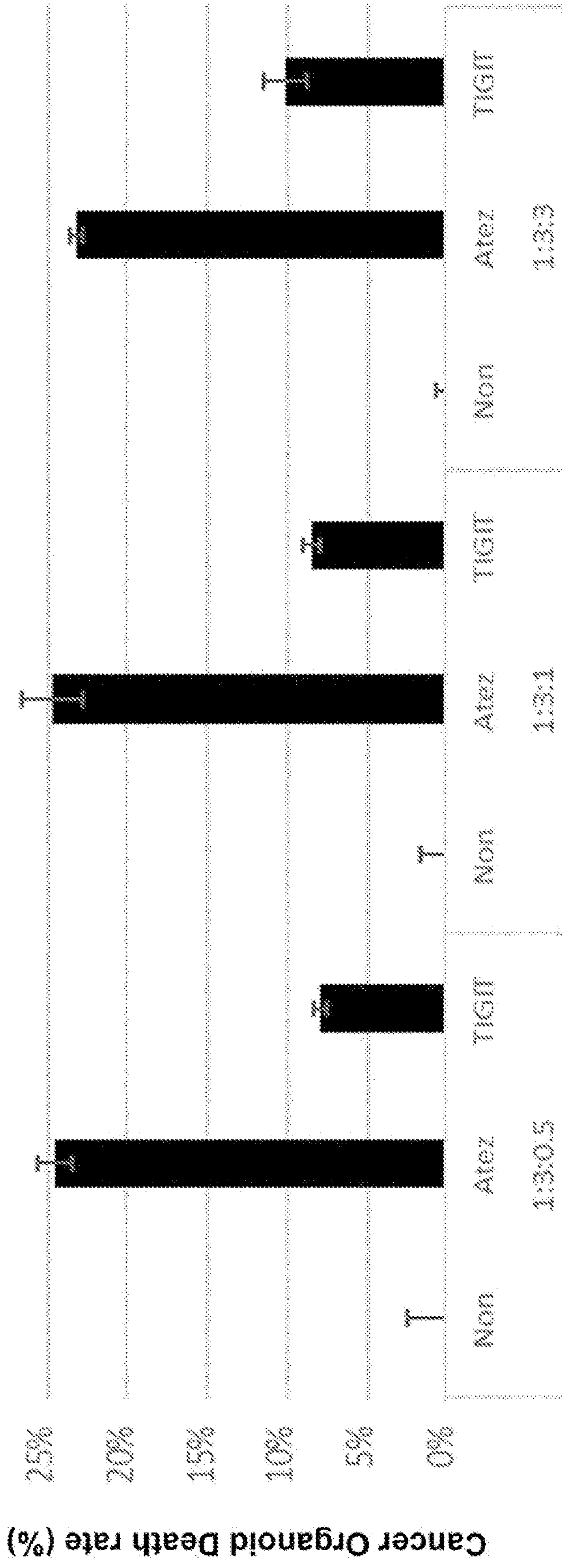
FIG. 19 is a graph showing the death rate of colorectal cancer organoids according to each co-culture ratio of colorectal cancer organoids, CD8+ T cells and Tregs, and it relates to the result of co-culture in the mixed condition in which colorectal cancer organoids and CD8+ T cells were fixed in the cell number ratio of 1:3. 'Non' refers to a drug-untreated group, 'Atez' refers to a drug-treated group treated with an atezolizumab as an exemplary drug, and 'TIGIT' refers to a drug-treated group treated with an anti-TIGIT antibody as an exemplary drug. The death rate was analyzed based on the results of measuring the growth rate after 72 hours (72 h) of drug treatment.

On the other hand, as shown in FIG. 19, when colorectal cancer organoids and CD8+ T cells was co-cultured at a mixing ratio of 1:3, the death rate of colorectal cancer organoids by the anti-TIGIT antibody increased as the Tregs ratio increased, with a maximum level of about 10%, and the death rate of cancer organoids by atezolizumab was also high as about 25%. That is, it was confirmed that the efficacy of all drugs such as atezolizumab and the anti-TIGIT antibody was higher in the above mixing ratio than in other mixing ratios, and the efficacy increased by two times or more.

Figure 20:
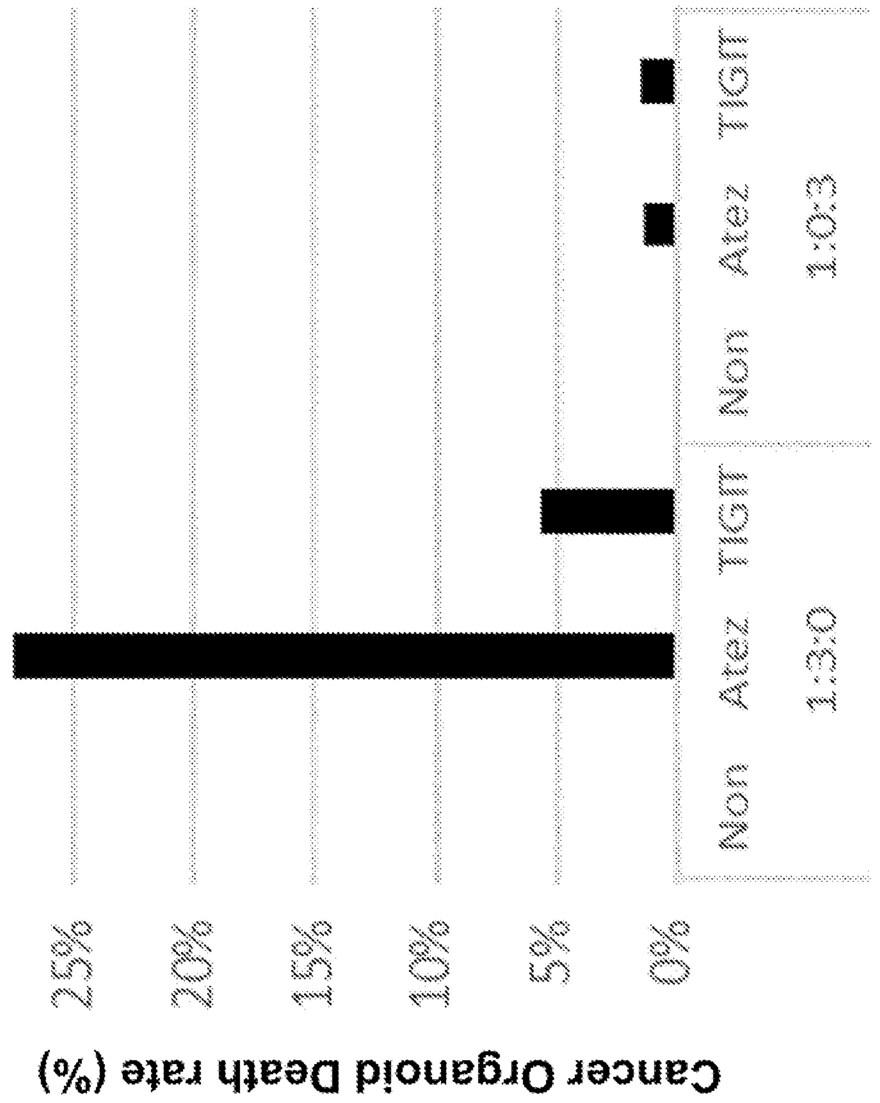
FIG. 20 is a graph showing the growth rate of lung cancer organoids according to each co-culture ratio of lung cancer organoids, CD8+ T cells and Tregs, and it relates to the result of co-culture under the conditions without Treg ("1:3:0") or without CD8+ T cell ("1:0:3"). 'Non' refers to a drug-untreated group, and 'Atez' refers to a drug-treated group treated with an atezolizumab as an exemplary drug, and 'TIGIT' refers to a drug-treated group treated with an anti-TIGIT antibody as an exemplary drug. The death rate was analyzed based on the results of measuring the growth rate after 72 hours (72 h) of drug treatment.

In addition, as shown in FIG. 20, when only the lung cancer organoids and CD8+ T cells were co-cultured at a mixing ratio of 1:3 except for Tregs among the cancer organoids, CD8+ T cells and Tregs, the death rate of cancer organoids by atezolizumab is as high as about 27%, but the death rate of cancer organoids by anti-TIGIT antibody is only about 6%, confirming that the efficacy of the drug could not be accurately determined. In addition, when only the lung cancer organoids and Tregs were co-cultured at a mixing ratio of 1:3 except for CD8+ T cells among the lung cancer organoids, CD8+ T cells and Tregs, the death rate of cancer organoids by atezolizumab and anti-TIGIT antibody was remarkably low at about 1%, confirming that the efficacy of the drug could not be accurately determined.

Figure 21:
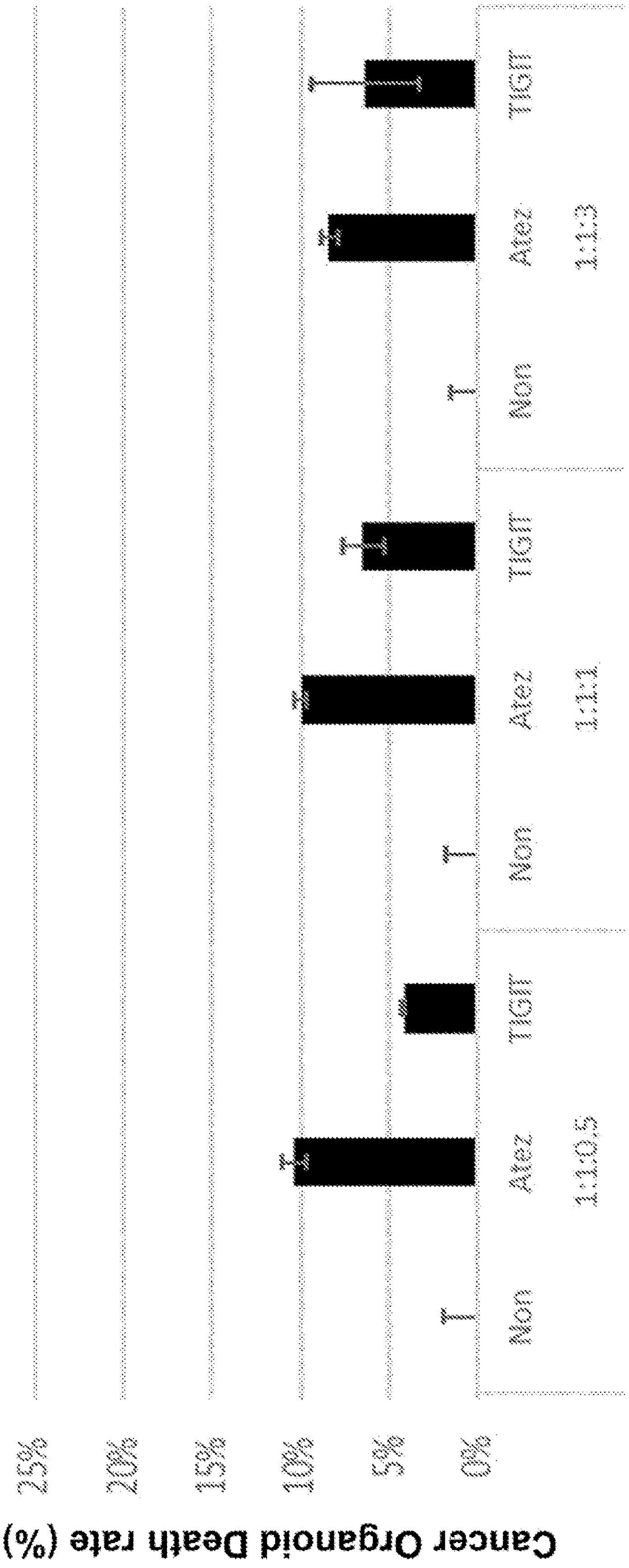
FIG. 21 is a graph showing the death rate of lung cancer organoids according to each co-culture ratio of lung cancer organoids, CD8+ T cells and Tregs, and it relates to the result of co-culture in the mixed condition in which colorectal cancer organoids and CD8+ T cells were fixed in the cell number ratio of 1:1. 'Non' refers to a drug-untreated group, 'Atez' refers to a drug-treated group treated with an atezolizumab as an exemplary drug, and 'TIGIT' refers to a drug-treated group treated with an anti-TIGIT antibody as an exemplary drug. The death rate was analyzed based on the results of measuring the growth rate after 72 hours (72 h) of drug treatment.

In addition, as shown in FIG. 21, when lung cancer organoids and CD8+ T cells were co-cultured at a ratio of 1:1, the death rate of cancer organoids by the anti-TIGIT antibody increased as the Treg mixing ratio increased, but the maximum level is just about 6%, and the death rate of cancer organoids by atezolizumab was just about 10% at maximum, confirming that the efficacy of the drug could not be accurately determined.

Figure 22:
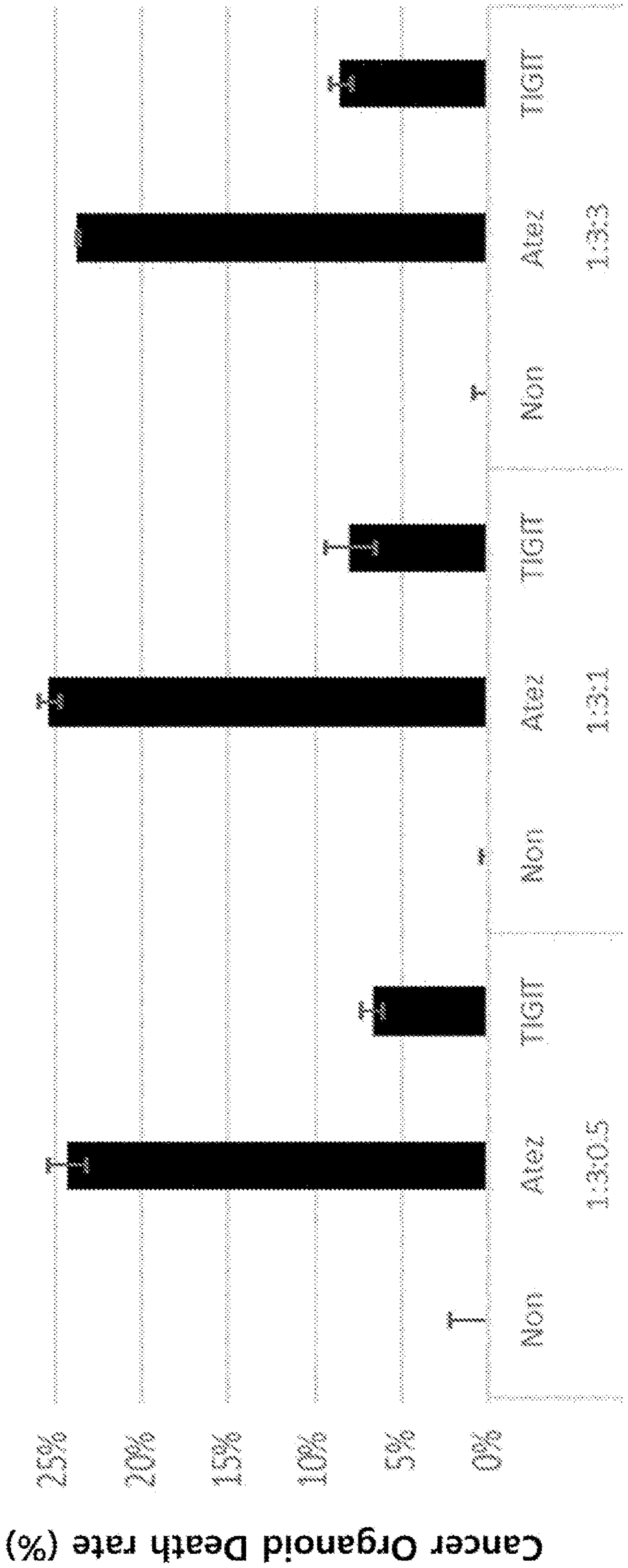
FIG. 22 is a graph showing the death rate of lung cancer organoids according to each co-culture ratio of lung cancer organoids, CD8+ T cells and Tregs, and it relates to the result of co-culture in the mixed condition in which colorectal cancer organoids and CD8+ T cells were fixed in the cell number ratio of 1:3. 'Non' refers to a drug-untreated group, 'Atez' refers to a drug-treated group treated with an atezolizumab as an exemplary drug, and 'TIGIT' refers to a drug-treated group treated with an anti-TIGIT antibody as an exemplary drug. The death rate was analyzed based on the results of measuring the growth rate after 72 hours (72 h) of drug treatment.

On the other hand, as shown in FIG. 22, when lung cancer organoids and CD8+ T cells was co-cultured at a mixing ratio of 1:3, the death rate of colorectal cancer organoids by the anti-TIGIT antibody increased as the Tregs mixing ratio increased, with a maximum level of about 10%, and the death rate of cancer organoids by atezolizumab was also high at about 25%. That is, it was confirmed that the efficacy of all drugs such as atezolizumab and the anti-TIGIT antibody was higher in the above mixing ratio than in other mixing ratios, and the efficacy increased by two times or more.

The above results suggest that setting the co-culture ratio of cancer organoids, CD8+ T cells and Treg to 1:3:0.5 to 3 is the most optimal ratio for an anticancer drug efficacy evaluation or screening system.

Example 5. Anticancer Drug Efficacy Evaluation and Screening System Comprising Cancer Organoids, Cytotoxic T Cells and Dendritic Cells The inventors have established an in vitro efficacy evaluation and screening system that can accurately predict the efficacy of a drug when administered to a subject, by similarly reproducing the environment in which cancer exists in the body.

Specifically, in order to establish a co-culture system in which cancer organoids, cytotoxic T cells (hereinafter referred to as 'CD8+ T cells') and dendritic cells (hereinafter referred to as 'DC') coexist, the inventors set a mixing ratio satisfying co-culture conditions under which (1) cancer organoids grow properly and (2) drug efficacy is well observed. As shown in Table 7 below, the ratio for cancer organoids was fixed to 1, the ratio for CD8+ T cells was set to 0 to 3 and the ratio for DC was set to 0.5 to 5. Herein, the number of organoids or cells was set to 1 for $5.0\times10^3$.

TABLE 7

| Group | Cancer Organoid | CD8+ T cell | DC |
|---|---|---|---|
| 1 | 1 | 0.5 | 0.5 |
| 2 | | | 1 |
| 3 | | | 5 |
| 4 | | 1 | 0.5 |
| 5 | | | 1 |
| 6 | | | 5 |
| 7 | | 3 | 0.5 |
| 8 | | | 1 |
| 9 | | | 5 |

Cancer organoids were prepared to have a 3D structure by isolating colorectal cancer or lung cancer tissues obtained from patients into single cells and culturing them together with ECM (extracellular matrix). The formed cancer organoids were confirmed to be tumors through pathological analysis, and used after being isolated into single cells using Tryp-LE.

CD8+ T cells isolated from PBMCs were used. PBMCs were isolated from blood obtained from donors by using Ficoll, and CD8+ T cells were isolated through MACS after a T cell activation process.

DCs differentiated from iPSCs were used, and DCs were differentiated from the H9 cell line using a general method known in the art.

Example 5.1. Co-Culture Ratio of Cancer Organoids, CD8+ T Cells and DCs

Specifically, for the co-cultures of cancer organoids, CD8+ T cells and DCs according to the mixing ratio in Table 7 above, those not treated with the drug were set as the control group (hereinafter referred to as 'drug-untreated group'), and those treated with an atezolizumab targeting CD8+ T cells as an exemplary drug were set as the experimental group (hereinafter referred to as 'drug-treated group'). Drugs were treated immediately after the start of co-culture, and the growth rate of cancer organoids was measured immediately after the start of the co-culture (0 h), after 24 hours (24 h), after 48 hours (48 h) and after 72 hours (72 h), respectively. The death rate was analyzed by the following method through the measured growth rate.

Cancer organoid death rate (%) = [1 − (growth rate of cancer organoids in the drug−treated group*)/(growth rate of cancer organoids in the drug−untreated group**)] × 100

Growth rate of cancer organoids in the drug−treated group (%) = (cancer organoid area after 24, 48 or 72 hours of drug treatment)/(cancer organoid area immediately after the start of the co−culture (0 h) × 100

Growth rate of cancer organoids in the drug−untreated group (%) = (cancer organoid area after 24, 48 or 72 hours without drug treatment)/(cancer organoid area immediately after the start of the co−culture (0 h) × 100

Figure 23:
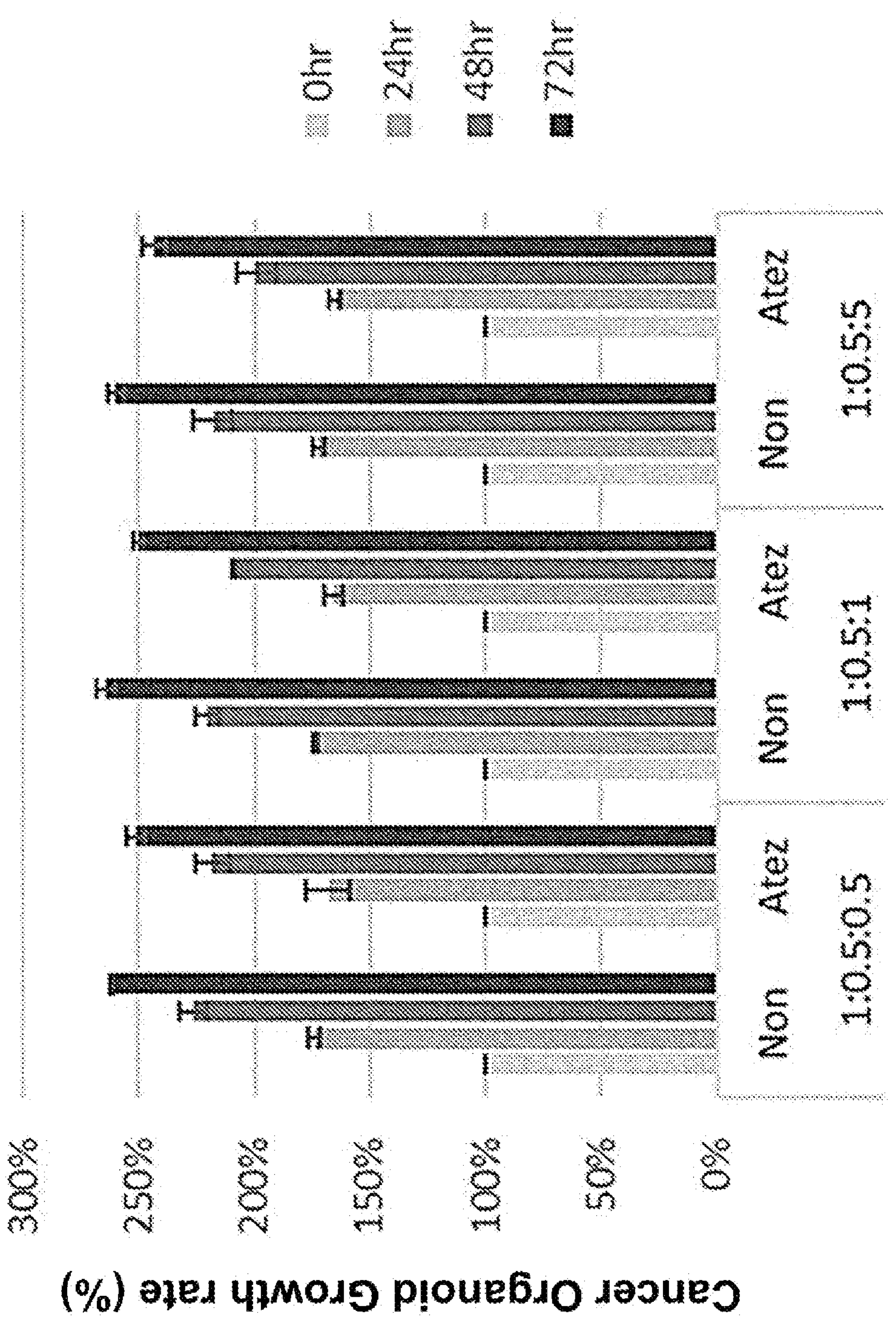
FIG. 23 is a graph showing the growth rate of colorectal cancer organoids according to each co-culture ratio of colorectal cancer organoids, CD8+ T cells and dendritic cells (hereinafter referred to as 'DC'), and it relates to the result of co-culture in the mixed condition in which colorectal cancer organoids and CD8+ T cells were fixed in the cell number ratio of 1:0.5. As a representative example, "1:0.5:0.5" described in the figure means that colorectal cancer organoids, CD8+ T cells and DCs are mixed in a cell number ratio of 1:0.5:0.5. The growth rate was analyzed immediately after the start of the co-culture (0 h), after 24 hours (24 h), after 48 hours (48 h), and after 72 hours (72 h), respectively. 'Non' refers to a drug-untreated group, and 'Atez' refers to a drug-treated group treated with an atezolizumab as an exemplary drug.
Figure 24:
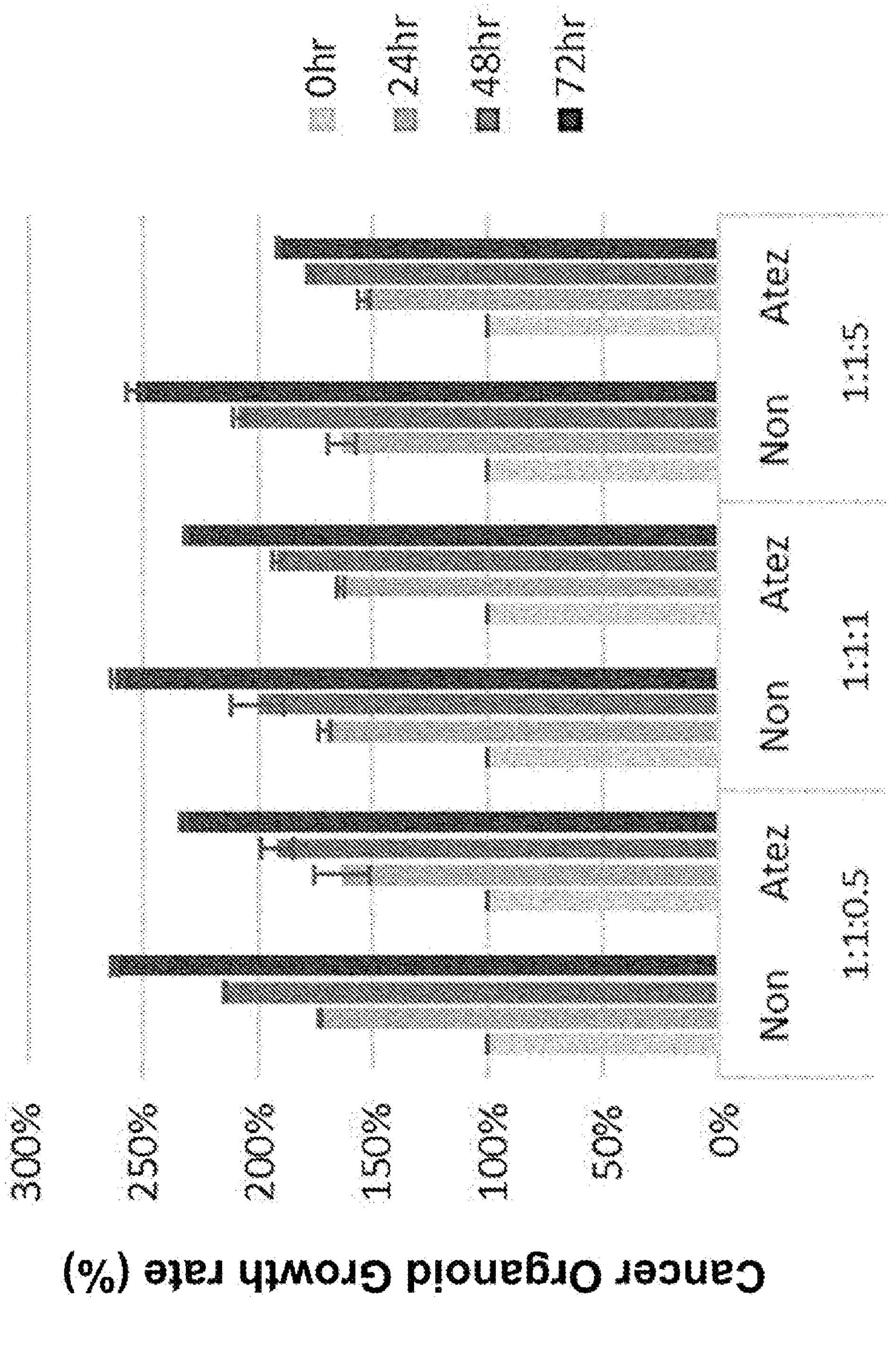
FIG. 24 is a graph showing the growth rate of colorectal cancer organoids according to each co-culture ratio of colorectal cancer organoids, CD8+ T cells and DCs, and it relates to the result of co-culture in the mixed condition in which colorectal cancer organoids and CD8+ T cells were fixed in the cell number ratio of 1:1. As a representative example, "1:1:0.5" described in the figure means that colorectal cancer organoids, CD8+ T cells and DCs are mixed in a cell number ratio of 1:1:0.5. The growth rate was analyzed immediately after the start of the co-culture (0 h), after 24 hours (24 h), after 48 hours (48 h), and after 72 hours (72 h), respectively. 'Non' refers to a drug-untreated group, and 'Atez' refers to a drug-treated group treated with an atezolizumab as an exemplary drug.
Figure 25:
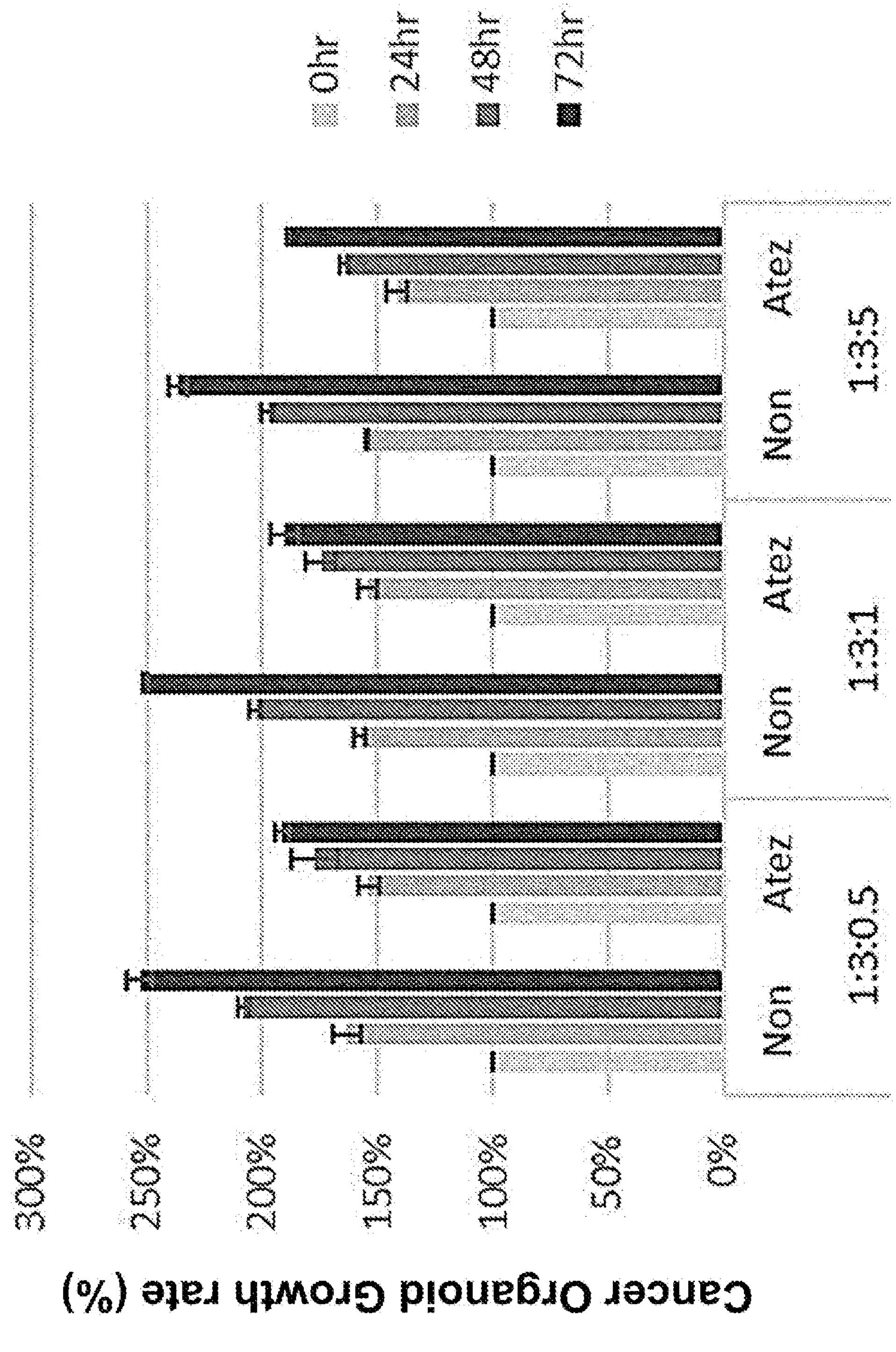
FIG. 25 is a graph showing the growth rate of colorectal cancer organoids according to each co-culture ratio of colorectal cancer organoids, CD8+ T cells and DCs, and it relates to the result of co-culture in the mixed condition in which colorectal cancer organoids and CD8+ T cells were fixed in the cell number ratio of 1:3. As a representative example, "1:3:0.5" described in the figure means that colorectal cancer organoids, CD8+ T cells and DCs are mixed in a cell number ratio of 1:3:0.5. The growth rate was analyzed immediately after the start of the co-culture (0 h), after 24 hours (24 h), after 48 hours (48 h), and after 72 hours (72 h), respectively. 'Non' refers to a drug-untreated group, and 'Atez' refers to a drug-treated group treated with an atezolizumab as an exemplary drug.

As a result, as shown in FIGS. 23 to 25, the growth of colorectal cancer organoids was not inhibited and grew appropriately in all mixing ratios when the drug was not treated, and no significant difference was found between each mixing ratio.

The drug did not significantly inhibit the growth of cancer organoids when co-culturing colorectal cancer organoids, CD8+ T cells and DCs at a mixing ratio of 1:0.5:0.5 to 5 (see FIG. 23), but the drug inhibited the growth of cancer organoids when co-culturing colorectal cancer organoids, CD8+ T cells and DCs at a mixing ratio of 1:1 to 3:0.5 to 5 (see FIGS. 24 and 25).

Figure 26:
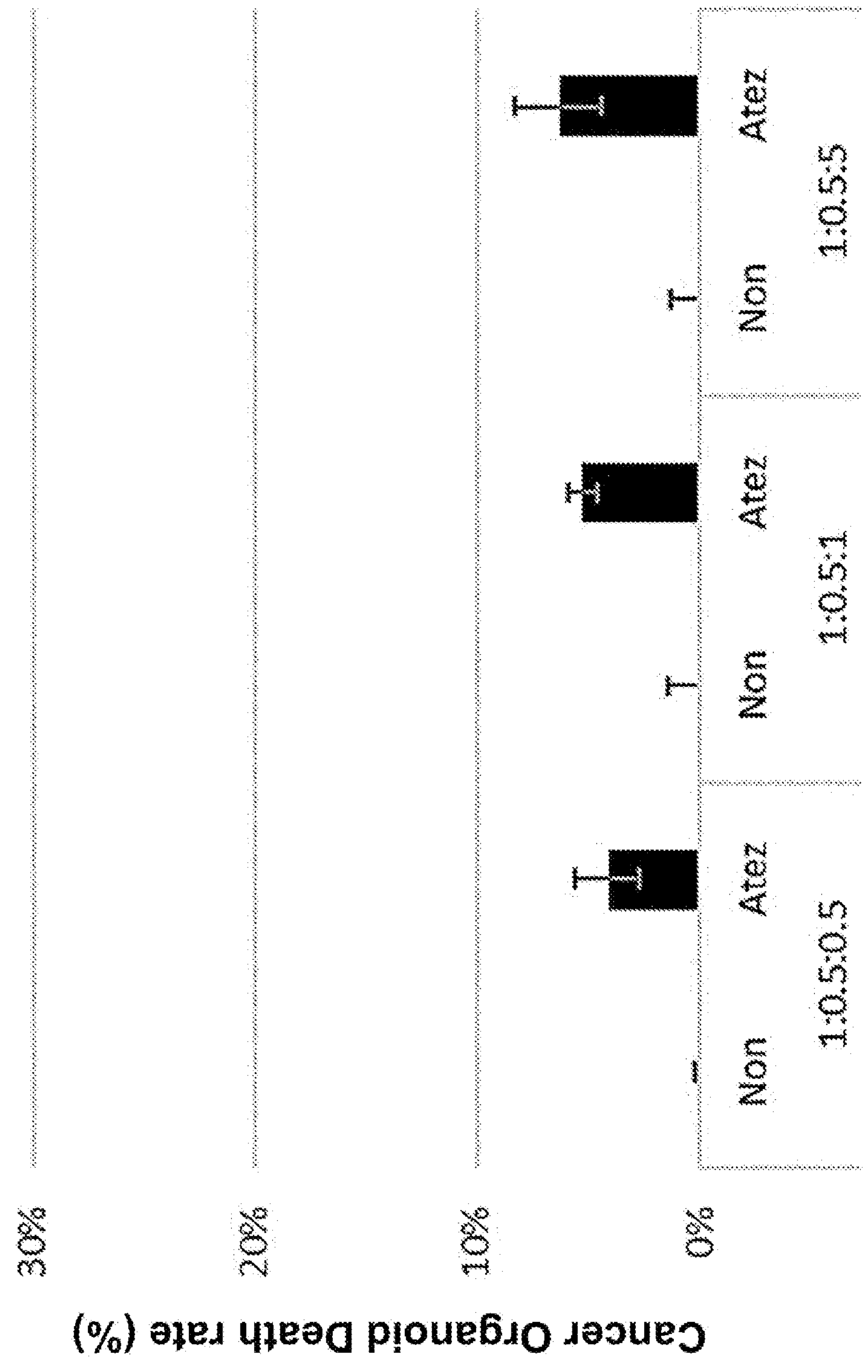
FIG. 26 is a graph showing the death rate of colorectal cancer organoids according to each co-culture ratio of colorectal cancer organoids, CD8+ T cells and DCs, and it relates to the result of co-culture in the mixed condition in which colorectal cancer organoids and CD8+ T cells were fixed in the cell number ratio of 1:0.5. 'Non' refers to a drug-untreated group, and 'Atez' refers to a drug-treated group treated with an atezolizumab as an exemplary drug.

In particular, as shown in FIG. 26, when colorectal cancer organoids and CD8+ T cells were co-cultured at a mixing ratio of 1:0.5, the death rate of cancer organoids by atezolizumab increased as the DC mixing ratio increased. However, the maximum level was just about 5%, and it was confirmed that the efficacy of the drug could not be accurately determined.

In addition, as shown in FIG. 27, when colorectal cancer organoids and CD8+ T cells are co-cultured at a mixing ratio of 1:1, the maximum death rate of cancer organoids by atezolizumab is just about 10%, confirming that the efficacy of the drug could not be accurately determined.

On the other hand, as shown in FIG. 28, when colorectal cancer organoids and CD8+ T cells are co-cultured at a mixing ratio of 1:3, the death rate of cancer organoids by atezolizumab was as high as about 20% to 25% regardless of the mixing ratio of DCs. That is, it was confirmed that the efficacy of the drug was higher in the mixing ratio than in other mixing ratios, and the efficacy increased by 2.5 to 5 times or more.

In addition, as shown in FIGS. 29 to 31, the growth of lung cancer organoids was not inhibited and grew appropriately at all mixing ratios when the drug was not treated, and no significant difference was found between each mixing ratio.

The drug did not significantly inhibit the growth of cancer organoids when co-culturing lung cancer organoids, CD8+ T cells and DCs at a mixing ratio of 1:0.5:0.5 to 5 or 1:1:0.5 to 1 (see FIGS. 29 and 30), but the drug inhibited the growth of cancer organoids when co-culturing lung cancer organoids, CD8+ T cells and DCs at a mixing ratio of 1:1:5 or 1:3:0.5 to 5 (see FIGS. 30 and 31).

In particular, as shown in FIG. 32, when lung cancer organoids and CD8+ T cells were co-cultured at a mixing ratio of 1:0.5, the death rate of cancer organoids by atezolizumab increased as the DC mixing ratio increased. However, the maximum level was just about 5%, and it was confirmed that the efficacy of the drug could not be accurately determined.

In addition, as shown in FIG. 33, when lung cancer organoids and CD8+ T cells are co-cultured at a mixing ratio of 1:1, the maximum death rate of cancer organoids by atezolizumab is just about 10%, confirming that the efficacy of the drug could not be accurately determined.

On the other hand, as shown in FIG. 34, when lung cancer organoids and CD8+ T cells was co-cultured at a mixing ratio of 1:3, the death rate of cancer organoids by atezolizumab was as high as about 28% to 40% regardless of the mixing ratio of DCs. That is, it was confirmed that the efficacy of the drug was higher in the mixing ratio than in other mixing ratios, and the efficacy increased by 5 to 8 times or more.

The above results suggest that setting the co-culture ratio of cancer organoids, CD8+ T cells and DCs to 1:3:0.5 to 5 is the most optimal ratio for an anticancer drug efficacy evaluation or screening system.

What is claimed is:

1. A method for evaluating an efficacy of an anticancer drug candidate, comprising:

(a) mixing cancer organoids and immune cells in a ratio of 1:0.5 to 5 and co-culturing the mixture;

(b) treating an anticancer drug candidate to the mixture of step (a); and (c) determining that the efficacy of the anticancer drug candidate is excellent when a growth inhibition or death of cancer organoid is increased in the mixture treated with the anticancer drug candidate of step (b) compared to a positive control group or a control group not treated with the anticancer drug candidate wherein when the immune cells are cytotoxic T cells and M1 macrophages, the co-culture of step (a) is performed by mixing cancer organoids, cytotoxic T cells and M1 macrophages in a cell number ratio of 1:0.5:0.5 to 3, wherein when the immune cells are M1 macrophages and M2 macrophages, the co-culture of step (a) is performed by mixing cancer organoids, M1 macrophages and M2 macrophages in a cell number ratio of 1:1 to 3:0.5 to 5.

wherein when the immune cells are TILs, the co-culture of step (a) is performed by mixing cancer organoids and TILs in a cell number ratio of 1:1 to 2, wherein when the immune cells are cytotoxic T cells and regulatory T cells, the co-culture of step (a) is performed by mixing cancer organoids, cytotoxic T cells and regulatory T cells in a cell number ratio of 1:3:0.5 to 3, and wherein when the immune cells are cytotoxic T cells and dendritic cells, the co-culture of step (a) is performed by mixing cancer organoids, cytotoxic T cells and dendritic cells in a cell number ratio of 1:3:0.5 to 5.

2. The method according to claim 1, wherein the immune cells are at least one selected from the group consisting of cytotoxic T cells, M1 macrophages, M2 macrophages, TILs, regulatory T cells and dendritic cells.

3. The method according to claim 1, wherein the anticancer drug is at least one selected from the group consisting of a compound, a peptide, a peptide mimetic, a fusion protein, an antibody, an aptamer, an antibody-drug conjugate (ADC), an antisense nucleic acid, a siRNA, a shRNA, a miRNA and a ribozyme that binds in a complementary manner to a DNA or a mRNA.

4. The method according to claim 1, wherein the cancer is at least one selected from the group consisting of biliary tract cancer, stomach cancer, lung cancer, liver cancer, colorectal cancer, colon cancer, small intestine cancer, pancreatic cancer, brain cancer, osteosarcoma, melanoma, breast cancer, sclerosing adenosis, uterine cancer, cervical cancer, head and neck cancer, esophageal cancer, thyroid cancer, parathyroid cancer, renal cancer, sarcoma, prostate cancer, urethral cancer, bladder cancer, hematologic malignancy, lymphoma, and fibroadenoma.

5. The method according to claim 1, wherein the growth inhibition or death of cancer organoids is confirmed by the increase or decrease of the area of the cancer organoids.

6. An anticancer drug efficacy evaluation system using the method according to claim 1, comprising cancer organoids and immune cells.

7. An anticancer drug screening system using the method according to claim 1, comprising cancer organoids and immune cells.

* * * * *